US009649170B2

(12) United States Patent
Park et al.

(10) Patent No.: US 9,649,170 B2
(45) Date of Patent: May 16, 2017

(54) ARTHROPLASTY SYSTEM AND RELATED METHODS

(71) Applicant: Howmedica Osteonics Corporation, Mahwah, NJ (US)

(72) Inventors: Ilwhan Park, Walnut Creek, CA (US); Charlie W. Chi, San Francisco, CA (US); Stephen M. Howell, Elk Grove, CA (US)

(73) Assignee: Howmedica Osteonics Corporation, Mahwah, NJ (US)

(*) Notice: Subject to any disclaimer, the term of this patent is extended or adjusted under 35 U.S.C. 154(b) by 658 days.

(21) Appl. No.: 14/011,998

(22) Filed: Aug. 28, 2013

(65) Prior Publication Data

US 2013/0345845 A1 Dec. 26, 2013

Related U.S. Application Data

(60) Division of application No. 12/563,809, filed on Sep. 21, 2009, now Pat. No. 8,545,509, and a (Continued)

(51) Int. Cl.
*A61B 34/10* (2016.01)
*A61B 5/055* (2006.01)
(Continued)

(52) U.S. Cl.
CPC .............. *A61B 34/10* (2016.02); *A61B 5/055* (2013.01); *A61B 17/15* (2013.01);
(Continued)

(58) Field of Classification Search
CPC ........ A61B 2034/101; A61B 2034/102; A61B 2034/104; A61B 2034/105
See application file for complete search history.

(56) References Cited

U.S. PATENT DOCUMENTS 3,195,411 A 7/1965 MacDonald et al.
3,825,151 A 7/1974 Arnaud
(Continued)

FOREIGN PATENT DOCUMENTS

DE 3305237 A1 8/1983
DE 4341367 C1 6/1995
(Continued)

OTHER PUBLICATIONS

U.S. Appl. No. 14/476,500, filed Sep. 3, 2014, Park.
(Continued)

*Primary Examiner* — David Bates
(74) *Attorney, Agent, or Firm* — Polsinelli PC

(57) ABSTRACT

A method of manufacturing an arthroplasty jig is disclosed herein. The method may include the following: generate a bone model, wherein the bone model includes a three dimensional computer model of at least a portion of a joint surface of a bone of a patient joint to undergo an arthroplasty procedure; generate an implant model, wherein the implant model includes a three dimensional computer model of at least a portion of a joint surface of an arthroplasty implant to be used in the arthroplasty procedure; assess a characteristic associated with the patient joint; generate a modified joint surface of the implant model by modifying at least a portion of a joint surface of the implant model according to the characteristic; and shape match the modified joint surface of the implant model and a corresponding joint surface of the bone model.

29 Claims, 56 Drawing Sheets

Related U.S. Application Data continuation-in-part of application No. 11/959,344, filed on Dec. 18, 2007, now Pat. No. 8,221,430, and a continuation-in-part of application No. 12/111,924, filed on Apr. 29, 2008, now Pat. No. 8,480,679, and a continuation-in-part of application No. 12/505,056, filed on Jul. 17, 2009, now Pat. No. 8,777,875.

(60) Provisional application No. 61/102,692, filed on Oct. 3, 2008, provisional application No. 61/083,053, filed on Jul. 23, 2008.

(51) Int. Cl.
*A61B 17/15* (2006.01)
*A61B 17/17* (2006.01)
*A61B 5/00* (2006.01)
*A61B 6/03* (2006.01)

(52) U.S. Cl.
CPC ...... *A61B 17/1703* (2013.01); *A61B 17/1725* (2013.01); *A61B 5/4504* (2013.01); *A61B 5/4514* (2013.01); *A61B 5/4533* (2013.01); *A61B 6/03* (2013.01); *A61B 17/155* (2013.01); *A61B 17/157* (2013.01); *A61B 17/1739* (2013.01); *A61B 17/1742* (2013.01); *A61B 17/1764* (2013.01); *A61B 2034/108* (2016.02)

(56) References Cited

U.S. PATENT DOCUMENTS

| | | |
|---|---|---|
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,517,969 A | 5/1985 | Halcomb et al. |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,035,699 A | 7/1991 | Coates |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,098,436 A | 3/1992 | Ferrante et al. |
| 5,099,846 A | 3/1992 | Hardy |
| 5,122,144 A | 6/1992 | Bert et al. |
| 5,123,927 A | 6/1992 | Duncan et al. |
| 5,133,758 A | 7/1992 | Hollister |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,282,803 A | 2/1994 | Lackey |
| 5,298,115 A | 3/1994 | Leonard |
| 5,298,254 A | 3/1994 | Prewett et al. |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| 5,514,140 A | 5/1996 | Lackey |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,755,803 A | 5/1998 | Haines et al. |
| 5,768,134 A | 6/1998 | Swaelens et al. |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia, III et al. |
| 5,908,424 A | 6/1999 | Bertin et al. |
| 5,911,724 A | 6/1999 | Wehrli |
| 5,916,221 A | 6/1999 | Hodorek et al. |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |

(56) References Cited

U.S. PATENT DOCUMENTS

| | | |
|---|---|---|
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Robie et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,955,345 B2 | 10/2005 | Kato |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini |
| D532,515 S | 11/2006 | Buttler et al. |
| 7,141,053 B2 | 11/2006 | Rose et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,177,386 B2 | 2/2007 | Mostafavi et al. |
| 7,184,814 B2 | 2/2007 | Lang et al. |
| 7,203,628 B1 | 4/2007 | St. Ville |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,373,286 B2 | 5/2008 | Nikolskiy et al. |
| 7,383,164 B2 | 6/2008 | Aram et al. |
| 7,388,972 B2 | 6/2008 | Kitson |
| 7,392,076 B2 | 6/2008 | de La Barrera |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,517,365 B2 | 4/2009 | Carignan et al. |
| 7,534,263 B2 | 5/2009 | Burdulis, Jr. et al. |
| 7,542,791 B2 | 6/2009 | Mire et al. |
| 7,547,307 B2 | 6/2009 | Carson et al. |
| 7,548,638 B2 | 6/2009 | Graessner |
| 7,584,080 B2 | 9/2009 | Taylor et al. |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,621,744 B2 | 11/2009 | Massoud |
| 7,621,920 B2 | 11/2009 | Claypool et al. |
| 7,630,750 B2 | 12/2009 | Liang et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,641,663 B2 | 1/2010 | Hodorek |
| 7,643,862 B2 | 1/2010 | Schoenefeld |
| 7,658,741 B2 | 2/2010 | Claypool et al. |
| 7,660,623 B2 | 2/2010 | Hunter et al. |
| 7,682,398 B2 | 3/2010 | Croxton et al. |
| 7,693,321 B2 | 4/2010 | Lehtonen-Krause |
| 7,695,520 B2 | 4/2010 | Metzger et al. |
| 7,699,847 B2 | 4/2010 | Sheldon et al. |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| 7,747,305 B2 | 6/2010 | Dean et al. |
| D619,718 S | 7/2010 | Gannoe et al. |
| D622,854 S | 8/2010 | Otto et al. |
| 7,769,429 B2 | 8/2010 | Hu |
| 7,780,672 B2 | 8/2010 | Metzger et al. |
| 7,780,681 B2 | 8/2010 | Sarin et al. |
| 7,787,932 B2 | 8/2010 | Vilsmeier et al. |
| 7,794,467 B2 | 9/2010 | McGinley et al. |
| 7,796,791 B2 | 9/2010 | Tsougarakis et al. |
| 7,799,077 B2 | 9/2010 | Lang et al. |
| D626,234 S | 10/2010 | Otto et al. |
| 7,806,838 B2 | 10/2010 | Tsai et al. |
| 7,806,896 B1 | 10/2010 | Bonutti |
| 7,815,645 B2 | 10/2010 | Haines |
| 7,824,181 B2 | 11/2010 | Sers |
| 7,842,039 B2 | 11/2010 | Hodorek et al. |
| 7,842,092 B2 | 11/2010 | Otto et al. |
| 7,881,768 B2 | 2/2011 | Lang et al. |
| 7,894,650 B2 | 2/2011 | Weng et al. |
| 7,927,335 B2 | 4/2011 | Deffenbaugh et al. |
| 7,935,150 B2 | 5/2011 | Carignan et al. |
| 7,940,974 B2 | 5/2011 | Skinner et al. |
| 7,950,924 B2 | 5/2011 | Brajnovic |
| 7,963,968 B2 | 6/2011 | Dees, Jr. |
| 7,967,868 B2 | 6/2011 | White et al. |
| D642,263 S | 7/2011 | Park |
| 7,974,677 B2 | 7/2011 | Mire et al. |
| 7,981,158 B2 | 7/2011 | Fitz et al. |
| 8,007,448 B2 | 8/2011 | Moctezuma de La Barrera |
| 8,021,368 B2 | 9/2011 | Haines |
| 8,036,729 B2 | 10/2011 | Lang et al. |
| 8,052,623 B2 | 11/2011 | Haimerl et al. |
| 8,059,878 B2 | 11/2011 | Feilkas et al. |
| 8,062,302 B2 | 11/2011 | Lang et al. |
| 8,066,708 B2 | 11/2011 | Lang et al. |
| 8,073,521 B2 | 12/2011 | Liew et al. |
| 8,077,950 B2 | 12/2011 | Tsougarakis et al. |
| 8,083,745 B2 | 12/2011 | Lang et al. |
| 8,086,336 B2 | 12/2011 | Christensen |
| 8,092,465 B2 | 1/2012 | Metzger et al. |
| 8,105,330 B2 | 1/2012 | Fitz et al. |
| 8,112,142 B2 | 2/2012 | Alexander et al. |
| 8,115,485 B1 | 2/2012 | Maier et al. |
| 8,122,582 B2 | 2/2012 | Burdulis, Jr. et al. |
| 8,126,533 B2 | 2/2012 | Lavallee |
| RE43,282 E | 3/2012 | Alexander et al. |
| 8,133,234 B2 | 3/2012 | Meridew et al. |
| 8,142,189 B2 | 3/2012 | Brajnovic |
| 8,160,345 B2 | 4/2012 | Pavlovskaia et al. |
| 8,165,657 B2 | 4/2012 | Krueger |
| 8,167,888 B2 | 5/2012 | Steffensmeier |
| 8,170,716 B2 | 5/2012 | Coste-Maniere et al. |
| 8,175,683 B2 | 5/2012 | Roose |
| 8,177,850 B2 | 5/2012 | Rudan et al. |

(56) References Cited

U.S. PATENT DOCUMENTS

| | | |
|---|---|---|
| 8,202,324 B2 | 6/2012 | Meulink et al. |
| 8,206,153 B2 | 6/2012 | Berckmans, III et al. |
| 8,214,016 B2 | 7/2012 | Lavallee et al. |
| 8,221,430 B2 | 7/2012 | Park et al. |
| 8,224,127 B2 | 7/2012 | Woodard et al. |
| 8,231,634 B2 | 7/2012 | Mahfouz et al. |
| 8,234,097 B2 | 7/2012 | Steines et al. |
| 8,241,293 B2 | 8/2012 | Stone et al. |
| 8,265,730 B2 | 9/2012 | Alexander et al. |
| 8,265,949 B2 | 9/2012 | Haddad |
| 8,282,646 B2 | 10/2012 | Schoenefeld et al. |
| 8,290,564 B2 | 10/2012 | Lang et al. |
| 8,306,601 B2 | 11/2012 | Lang et al. |
| 8,311,306 B2 | 11/2012 | Pavlovskaia et al. |
| 8,323,288 B2 | 12/2012 | Zajac |
| 8,331,634 B2 | 12/2012 | Barth et al. |
| 8,337,501 B2 | 12/2012 | Fitz et al. |
| 8,377,066 B2 | 2/2013 | Katrana et al. |
| 8,398,646 B2 | 3/2013 | Metzger et al. |
| 8,407,067 B2 | 3/2013 | Uthgenannt et al. |
| 8,460,302 B2 | 6/2013 | Park et al. |
| 8,460,303 B2 | 6/2013 | Park |
| D691,719 S | 10/2013 | Park |
| 8,545,509 B2 | 10/2013 | Park et al. |
| 8,617,171 B2 | 12/2013 | Park et al. |
| 8,702,712 B2 | 4/2014 | Jordan et al. |
| 8,737,700 B2 | 5/2014 | Park et al. |
| 8,777,955 B2 | 7/2014 | Park |
| 8,801,719 B2 | 8/2014 | Park et al. |
| 8,801,720 B2 | 8/2014 | Park et al. |
| 8,828,011 B2 | 9/2014 | Park et al. |
| 9,265,509 B2 | 2/2016 | Park et al. |
| 2002/0160337 A1 | 10/2002 | Klein et al. |
| 2002/0183760 A1 | 12/2002 | McGovern |
| 2003/0009167 A1 | 1/2003 | Wozencroft |
| 2003/0055502 A1 | 3/2003 | Lang et al. |
| 2004/0102792 A1 | 5/2004 | Sarin et al. |
| 2004/0102866 A1 | 5/2004 | Harris et al. |
| 2004/0133276 A1 | 7/2004 | Lang et al. |
| 2004/0147927 A1 | 7/2004 | Tsougarakis et al. |
| 2004/0153066 A1 | 8/2004 | Coon et al. |
| 2004/0153087 A1 | 8/2004 | Sanford et al. |
| 2004/0204760 A1 | 10/2004 | Fitz et al. |
| 2004/0220583 A1 | 11/2004 | Pieczynski, II et al. |
| 2004/0243148 A1 | 12/2004 | Wasielewski |
| 2004/0243481 A1 | 12/2004 | Bradbury et al. |
| 2005/0054914 A1 | 3/2005 | Duerk et al. |
| 2005/0059978 A1 | 3/2005 | Sherry et al. |
| 2005/0065617 A1 | 3/2005 | de la Barrera et al. |
| 2005/0080426 A1 | 4/2005 | Qian |
| 2005/0149091 A1 | 7/2005 | Tanamal et al. |
| 2005/0192588 A1 | 9/2005 | Garcia |
| 2005/0245934 A1 | 11/2005 | Tuke et al. |
| 2005/0245936 A1 | 11/2005 | Tuke et al. |
| 2005/0256389 A1 | 11/2005 | Koga et al. |
| 2005/0267584 A1 | 12/2005 | Burdulis, Jr. et al. |
| 2005/0272998 A1 | 12/2005 | Diehl et al. |
| 2006/0015018 A1 | 1/2006 | Jutras et al. |
| 2006/0015030 A1 | 1/2006 | Poulin et al. |
| 2006/0015188 A1 | 1/2006 | Grimes |
| 2006/0079755 A1 | 4/2006 | Stazzone et al. |
| 2006/0110017 A1 | 5/2006 | Tsai et al. |
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0161167 A1 | 7/2006 | Myers |
| 2006/0195113 A1 | 8/2006 | Masini |
| 2006/0244448 A1 | 11/2006 | Ballon et al. |
| 2006/0271058 A1 | 11/2006 | Ashton et al. |
| 2007/0010732 A1 | 1/2007 | DeYoe et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0083266 A1 | 4/2007 | Lang |
| 2007/0100338 A1 | 5/2007 | Deffenbaugh et al. |
| 2007/0100462 A1 | 5/2007 | Lang et al. |
| 2007/0114370 A1 | 5/2007 | Smith et al. |
| 2007/0118055 A1 | 5/2007 | McCombs |
| 2007/0118243 A1 | 5/2007 | Schroeder et al. |
| 2007/0123856 A1 | 5/2007 | Deffenbaugh et al. |
| 2007/0123857 A1 | 5/2007 | Deffenbaugh et al. |
| 2007/0123912 A1 | 5/2007 | Carson |
| 2007/0162039 A1 | 7/2007 | Wozencroft |
| 2007/0167833 A1 | 7/2007 | Redel et al. |
| 2007/0173853 A1 | 7/2007 | MacMillan |
| 2007/0173858 A1 | 7/2007 | Engh et al. |
| 2007/0191741 A1 | 8/2007 | Tsai et al. |
| 2007/0213738 A1 | 9/2007 | Martin et al. |
| 2007/0226986 A1 | 10/2007 | Park et al. |
| 2007/0232959 A1 | 10/2007 | Couture et al. |
| 2007/0233136 A1 | 10/2007 | Wozencroft |
| 2007/0233141 A1 | 10/2007 | Park et al. |
| 2007/0233269 A1 | 10/2007 | Steines et al. |
| 2007/0237372 A1 | 10/2007 | Chen et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2008/0004701 A1 | 1/2008 | Axelson et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson |
| 2008/0015606 A1 | 1/2008 | D'Alessio et al. |
| 2008/0015607 A1 | 1/2008 | D'Alessio et al. |
| 2008/0021299 A1 | 1/2008 | Meulink |
| 2008/0033442 A1 | 2/2008 | Amiot et al. |
| 2008/0058613 A1 | 3/2008 | Lang et al. |
| 2008/0088761 A1 | 4/2008 | Lin et al. |
| 2008/0089591 A1 | 4/2008 | Zhou et al. |
| 2008/0114370 A1 | 5/2008 | Schoenefeld |
| 2008/0147072 A1 | 6/2008 | Park et al. |
| 2008/0153067 A1 | 6/2008 | Berckmans et al. |
| 2008/0195108 A1 | 8/2008 | Bhatnagar et al. |
| 2008/0208081 A1 | 8/2008 | Murphy |
| 2008/0232661 A1 | 9/2008 | Habets |
| 2008/0234685 A1 | 9/2008 | Gjerde |
| 2008/0257363 A1 | 10/2008 | Schoenefeld et al. |
| 2008/0275452 A1 | 11/2008 | Lang et al. |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0125114 A1 | 5/2009 | May et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0151736 A1 | 6/2009 | Belcher et al. |
| 2009/0163923 A1 | 6/2009 | Flett et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0306676 A1 | 12/2009 | Lang et al. |

(56) References Cited

U.S. PATENT DOCUMENTS

| | | |
|---|---|---|
| 2009/0312805 A1 | 12/2009 | Lang et al. |
| 2010/0023015 A1 | 1/2010 | Park |
| 2010/0036252 A1 | 2/2010 | Chalana et al. |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0145344 A1 | 6/2010 | Jordan et al. |
| 2010/0152741 A1 | 6/2010 | Park et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0191242 A1 | 7/2010 | Massoud |
| 2010/0198351 A1 | 8/2010 | Meulink |
| 2010/0209868 A1 | 8/2010 | De Clerck |
| 2010/0228257 A1 | 9/2010 | Bonutti |
| 2010/0256479 A1 | 10/2010 | Park et al. |
| 2010/0274534 A1 | 10/2010 | Steines et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0029093 A1 | 2/2011 | Bojarski et al. |
| 2011/0046735 A1 | 2/2011 | Metzger et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092978 A1 | 4/2011 | McCombs |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190775 A1 | 8/2011 | Ure |
| 2011/0190899 A1 | 8/2011 | Pierce et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0143197 A1 | 6/2012 | Lang et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165821 A1 | 6/2012 | Carignan et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |
| 2012/0310400 A1 | 12/2012 | Park |
| 2013/0115474 A1 | 5/2013 | Park |
| 2013/0116697 A1 | 5/2013 | Park et al. |
| 2013/0123789 A1 | 5/2013 | Park |
| 2013/0190767 A1 | 7/2013 | Park et al. |
| 2013/0197526 A1 | 8/2013 | Park et al. |
| 2014/0005997 A1 | 1/2014 | Park |
| 2014/0078139 A1 | 3/2014 | Park et al. |
| 2014/0081277 A1 | 3/2014 | Park et al. |
| 2014/0128875 A1 | 5/2014 | Park et al. |
| 2014/0324205 A1 | 10/2014 | Park et al. |
| 2014/0330278 A1 | 11/2014 | Park et al. |
| 2014/0330279 A1 | 11/2014 | Park et al. |
| 2016/0015466 A1 | 1/2016 | Park et al. |
| 2016/0095609 A1 | 4/2016 | Park et al. |

FOREIGN PATENT DOCUMENTS

| | | |
|---|---|---|
| DE | 102005023028 A1 | 11/2006 |
| EP | 0097001 | 12/1983 |
| EP | 0574098 A | 12/1993 |
| EP | 0622052 A | 11/1994 |
| EP | 0709061 A1 | 5/1996 |
| EP | 0908836 A2 | 4/1999 |
| EP | 0908836 A3 | 12/1999 |
| EP | 1059153 A2 | 12/2000 |
| EP | 1486900 A1 | 12/2004 |
| EP | 1532939 A1 | 5/2005 |
| EP | 1669033 A1 | 6/2006 |
| FR | 2478462 A1 | 9/1981 |
| GB | 2215610 A1 | 9/1989 |
| GB | 2420717 A | 6/2006 |
| GB | 2447702 A | 9/2008 |
| JP | 10-94538 | 4/1998 |
| JP | 2001-092950 | 4/2001 |
| JP | P 2005-287813 | 10/2005 |
| WO | WO 93/25157 A1 | 12/1993 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 98/32384 | 7/1998 |
| WO | WO 00/35346 | 6/2000 |
| WO | WO 01/00096 A1 | 1/2001 |
| WO | WO 01/70142 A1 | 9/2001 |
| WO | WO 01/85040 A1 | 11/2001 |
| WO | WO 02/096268 A2 | 12/2002 |
| WO | WO 2004/032806 A1 | 4/2004 |
| WO | WO 2004/049981 A2 | 6/2004 |
| WO | WO 2005/051240 A1 | 6/2005 |
| WO | WO 2005/087125 A2 | 9/2005 |
| WO | WO 2006/058057 A2 | 6/2006 |
| WO | WO 2006/060795 A1 | 6/2006 |
| WO | WO 2006/092600 A1 | 9/2006 |
| WO | WO 2006/127486 A2 | 11/2006 |
| WO | WO 2006/134345 A1 | 12/2006 |
| WO | WO 2007/014164 A2 | 2/2007 |
| WO | WO 2007/058632 A1 | 5/2007 |
| WO | WO 2007/092841 A2 | 8/2007 |
| WO | WO 2007/097853 A2 | 8/2007 |
| WO | WO 2007/097854 A2 | 8/2007 |

(56) References Cited

FOREIGN PATENT DOCUMENTS

| WO | WO 2007/137327 A1 | 12/2007 |
|----|-------------------|---------|
| WO | WO 2008/014618 A1 | 2/2008  |
| WO | WO 2008/091358 A1 | 7/2008  |

OTHER PUBLICATIONS

Advisory Action and Interview Summary, U.S. Appl. No. 12/390,667, mailed Apr. 27, 2012, 23 pages.
Advisory Action, U.S. Appl. No. 11/642,385, dated Oct. 29, 2010, 3 pages.
Amendment and Response to Ex Parte Quayle Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Non-Final Office Action, U.S. Appl. No. 11/959,344, dated Jul. 15, 2011, 13 pages.
Amendment and Response to Office Action and Petition to Revive, U.S. Appl. No. 10/146,862, filed Jan. 18, 2006, 29 pages.
Amendment and Response to Office Action, U.S. Appl. No. 11/656,323, filed Jun. 25, 2010, 7 pages.
Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.
Amendment and Response, U.S. Appl. No. 11/642,385, filed May 28, 2010, 11 pages.
Amendment Under 37 C.F.R. 1.312, U.S. Appl. No. 12/386,105, filed Oct. 1, 2012, 6 pages.
Appeal Brief, U.S. Appl. No. 12/390,667, filed Jul. 12, 2012, 32 pages.
Appeal Brief, U.S. Appl. No. 12/391,008, filed Oct. 16, 2012, 24 pages.
European Search Report, 10192631.9-2310, dated Mar. 17, 2011, 5 pages.
Ex Parte Quayle Action, U.S. Appl. No. 29/296,687, mailed Jan. 24, 2011, 11 pages.
Examiner's Answer in appeal, U.S. Appl. No. 12/391,008, mailed Dec. 13, 2012, 27 pages.
Final Office Action and PTO-892, U.S. Appl. No. 11/641,382, mailed Aug. 5, 2010, 13 pages.
Final Office Action and PTO-892, U.S. Appl. No. 11/656,323, mailed Sep. 3, 2010, 11 pages.
Final Office Action, U.S. Appl. No. 11/641,569, mailed May 10, 2010, 9 pages.
Final Office Action, U.S. Appl. No. 11/959,344, mailed Oct. 27, 2011, 12 pages.
Final Office Action, U.S. Appl. No. 12/390,667, mailed Jan. 13, 2012, 27 pages.
Final Office Action, U.S. Appl. No. 11/641,382, mailed Jul. 25, 2012, 12 pages.
Final Office Action, U.S. Appl. No. 11/641,569, mailed Mar. 1, 2012, 12 pages.
Final Office Action, U.S. Appl. No. 11/924,425, mailed Jul. 6, 2012, 14 pages.
Final Office Action, U.S. Appl. No. 11/946,002, mailed May 9, 2012, 24 pages.
Final Office Action, U.S. Appl. No. 12/391,008, mailed May 17, 2012, 28 pages.
Final Office Action, U.S. Appl. No. 12/563,809, mailed Mar. 7, 2013, 14 pages.
International Search Report and Written Opinion, International Application No. PCT/US2009/034983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
International Search Report and Written Opinion, International Application No. PCT/US2009/040629, mailed Aug. 6, 2009, 9 pages.
International Search Report and Written Opinion, International Application No. PCT/US2009/051109, mailed Nov. 6, 2009, 13 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
International Search Report and Written Opinion, PCT/US2007/001624, dated Dec. 12, 2007, 14 pages.
International Search Report and Written Opinion, PCT/US2007/001622, dated Jun. 11, 2007, 14 pages.
International Search Report and Written Opinion, PCT/US2008/083125, dated Mar. 9, 2009, 13 pages.
International Search Report and Written Opinion, PCT/US2011/032342, dated Jul. 1, 2011, 8 pages.
Invitation to Pay Additional Fees mailed on Jul. 31, 2007, for PCT Application No. PCT/US2007/001624 filed on Jan. 19, 2007, 5 pages.
Non-Final Office Action and PTO-892, U.S. Appl. No. 11/641,382, mailed Jan. 20, 2010, 12 pages.
Non-Final Office Action and PTO-892, U.S. Appl. No. 11/642,385, mailed Mar. 2, 2010, 11 pages.
Non-Final Office Action and PTO-892, U.S. Appl. No. 11/656,323, mailed Mar. 30, 2010, 10 pages.
Non-Final Office Action, U.S. Appl. No. 11/641,569, dated Aug. 3, 2011, 14 pages.
Non-Final Office Action, U.S. Appl. No. 11/924,425, mailed Jan. 25, 2012, 35 pages.
Non-Final Office Action, U.S. Appl. No. 12/390,667, dated Aug. 24, 2011, 49 pages.
Non-Final Office Action, U.S. Appl. No. 11/641,382, mailed Mar. 29, 2012, 24 pages.
NonFinal Office Action, U.S. Appl. No. 11/641,569, mailed Nov. 12, 2009, 9 pages.
Non-Final Office Action, U.S. Appl. No. 11/946,002, dated Nov. 25, 2011, 44 pages.
Nonfinal Office Action, U.S. Appl. No. 11/959,344, dated Feb. 15, 2011, 29 pages.
Non-Final Office Action, U.S. Appl. No. 12/111,924, mailed Jun. 29, 2012, 35 pages.
Non-Final Office Action, U.S. Appl. No. 12/386,105, dated Feb. 9, 2012, 30 pages.
Non-Final Office Action, U.S. Appl. No. 12/390,667, mailed Sep. 26, 2012, 21 pages.
Non-Final Office Action, U.S. Appl. No. 12/391,008, mailed Oct. 31, 2011, 44 pages.
Non-Final Office Action, U.S. Appl. No. 12/546,545, mailed Jul. 19, 2012, 28 pages.
Non-Final Office Action, U.S. Appl. No. 12/563,809, mailed Sep. 21, 2012, 32 pages.
Non-Final Office Action, U.S. Appl. No. 12/636,939, mailed Jul. 20, 2012, 25 pages.
Non-Final Office Action, U.S. Appl. No. 13/374,960, mailed Aug. 1, 2012, 6 pages.
Notice of Allowance, U.S. Appl. No. 13/066,568, mailed Oct. 26, 2011, 28 pages.
Notice of Allowance, U.S. Appl. No. 11/641,382, mailed Oct. 9, 2012, 9 pages.

(56) References Cited

OTHER PUBLICATIONS

Notice of Allowance, U.S. Appl. No. 11/924,425, mailed Sep. 25, 2012, 18 pages.
Notice of Allowance, U.S. Appl. No. 11/959,344, mailed Mar. 5, 2012, 13 pages.
Notice of Allowance, U.S. Appl. No. 12/386,105, mailed Jul. 5, 2012, 11 pages.
Notice of Allowance, U.S. Appl. No. 12/563,809, mailed May 28, 2013, 11 pages.
Notice of Allowance, U.S. Appl. No. 13/374,960, mailed Nov. 2, 2012, 24 pages.
Notice of Allowance, U.S. Appl. No. 29/296,687, mailed Mar. 31, 2011, 18 pages.
Notice of Non-Compliant Amendment, U.S. Appl. No. 11/641,569, mailed Aug. 7, 2009, 3 pages.
Office Action (Restriction Requirement), U.S. Appl. No. 12/563,809, dated Feb. 2, 2012, 7 pages.
Office Action, U.S. Appl. No. 10/146,862, mailed Jan. 13, 2005, 10 pages.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
RCE/Amendment, U.S. Appl. No. 11/641,569, filed Aug. 9, 2010, 18 pages.
RCE/Amendment, U.S. Appl. No. 11/642,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
RCE/Amendment, U.S. Appl. No. 11/946,002, filed Sep. 6, 2012, 38 pages.
Response to Final Office Action, U.S. Appl. No. 11/641,569, filed Jun. 28, 2012, 10 pages.
Response to Final Office Action, U.S. Appl. No. 11/641,382, filed Sep. 24, 2012, 11 pages.
Response to Final Office Action, U.S. Appl. No. 11/959,344, filed Dec. 27, 2011, 16 pages.
Response to Final Office Action, U.S. Appl. No. 11/924,425, filed Sep. 5, 2012, 9 pages.
Response to Final Office Action, U.S. Appl. No. 12/390,667, filed Mar. 12, 2012, 19 pages.
Response to Final Office Action, U.S. Appl. No. 12/563,809, filed May 6, 2013, 15 pages.
Response to Non-Final Office Action, U.S. Appl. No. 12/563,809, filed Dec. 13, 2012, 15 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Non-Final Office Action, U.S. Appl. No. 11/924,425, filed Apr. 25, 2012, 8 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Response to Restriction Requirement, U.S. Appl. No. 11/959,344, filed Nov. 24, 2010, 13 pages.
Response to Restriction Requirement, U.S. Appl. No. 12/390,667, dated Jul. 27, 2011, 8 pages.
Response to Restriction Requirement, U.S. Appl. No. 12/391,008, filed Aug. 29, 2011, 9 pages.
Response to Restriction Requirement, U.S. Appl. No. 12/386,105, filed Dec. 21, 2011, 9 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/563,809, filed Aug. 6, 2012, 10 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Restriction Requirement, U.S. Appl. No. 11/641,382, mailed Sep. 3, 2009, 6 pages.
Restriction Requirement, U.S. Appl. No. 11/641,569, mailed Apr. 27, 2009, 7 pages.
Restriction Requirement, U.S. Appl. No. 11/642,385, mailed Oct. 27, 2009, 7 pages.
Restriction Requirement, U.S. Appl. No. 11/656,323, mailed Nov. 13, 2009, 10 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 11/959,344, dated Oct. 29, 2010, 6 pages.
Restriction Requirement, U.S. Appl. No. 12/111,924, mailed Mar. 19, 2012, 8 pages.
Restriction Requirement, U.S. Appl. No. 12/386,105, dated Oct. 24, 2011, 7 pages.
Restriction Requirement, U.S. Appl. No. 12/390,667, dated Jul. 14, 2011, 9 pages.
Restriction Requirement, U.S. Appl. No. 12/391,008, dated Aug. 18, 2011, 6 pages.
Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/563,809, mailed Jul. 6, 2012, 6 pages.
Restriction Requirement, U.S. Appl. No. 12/636,939, mailed Apr. 13, 2012, 6 pages.
Restriction Requirement, U.S. Appl. No. 29/296,687, mailed Sep. 21, 2010, 7 pages.
Advisory Action, U.S. Appl. No. 11/642,385, dated Aug. 1, 2014.
Amendment and Response After Final Office Action, U.S. Appl. No. 11/656,323, dated Aug. 25, 2014.
Amendment Under 37 C.F.R. 1.312, U.S. Appl. No. 13/374,960, filed May 7, 2013, 6 pages.
Appeal Brief, U.S. Appl. No. 11/642,385, dated Oct. 7, 2014.
Canadian Office Action, Appl. No. 2708393, dated Jul. 29, 2014.
European Search Report, EP 09835583.7, dated May 9, 2014.
European Search Report, EP09739422.5, dated Mar. 28, 2013, 9 pages.
European Search Report, EP09823986.6, dated Sep. 23, 2014.
European search Report, European Appl. No. 08863202.1, dated May 16, 2014.
Extended European Search Report, European Appl. No. 13188389.4, dated Jan. 8, 2014.

(56) References Cited

OTHER PUBLICATIONS

Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Final Office Action, U.S. Appl. No. 11/641,569, dated Nov. 29, 2013, 20 pages.
Final Office Action, U.S. Appl. No. 11/642,385, dated Apr. 25, 2014.
Final Office Action, U.S. Appl. No. 11/656,323, dated Apr. 3, 2014.
Final Office Action, U.S. Appl. No. 11/946,002, dated Sep. 17, 2014.
Final Office Action, U.S. Appl. No. 12/390,667, dated Oct. 25, 2013, 17 pages.
Final Office Action, U.S. Appl. No. 12/505,056, dated Dec. 30, 2013, 48 pages.
Final Office Action, U.S. Appl. No. 12/546,545, dated Oct. 7, 2013, 24 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.
International Search Report and Written Opinion, PCT/US2014/030496, dated Aug. 6, 2014.
Japanese Office Action, JP Application No. 2011-507530, dated Dec. 17, 2013, 8 pages.
Non-Final Office Action, U.S. Appl. No. 11/641,569, dated Jan. 3, 2013, 12 pages.
Non-Final Office Action, U.S. Appl. No. 13/086,275, mailed Feb. 7, 2013, 36 pages.
Non-Final Office Action, U.S. Appl. No. 11/641,569, mailed Jul. 12, 2013, 21 pages.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 11/656,323, dated Sep. 18, 2014.
Non-Final Office Action, U.S. Appl. No. 11/946,002, dated Oct. 2, 2013, 39 pages.
Non-Final Office Action, U.S. Appl. No. 11/946,002, dated Feb. 6, 2014, 46 pages.
Non-Final Office Action, U.S. Appl. No. 12/390,667, mailed May 8, 2013, 20 pages.
Non-Final Office Action, U.S. Appl. No. 12/505,056, mailed Jun. 28, 2013, 7 pages.
Non-Final Office Action, U.S. Appl. No. 12/546,545, mailed Mar. 13, 2013, 10 pages.
Non-Final Office Action, U.S. Appl. No. 12/636,939, mailed Apr. 25, 2013, 16 pages.
Non-Final Office Action, U.S. Appl. No. 12/760,388, mailed Jun. 20, 2013, 54 pages.
Non-Final Office Action, U.S. Appl. No. 13/488,505, dated Jul. 17, 2014.
Non-Final Office Action, U.S. Appl. No. 13/723,904, mailed Aug. 9, 2013, 6 pages.
Non-Final Office Action, U.S. Appl. No. 13/730,467, dated Jan. 15, 2014, 8 pages.
Non-Final Office Action, U.S. Appl. No. 13/730,585, mailed Jun. 11, 2013, 10 pages.
Non-Final Office Action, U.S. Appl. No. 13/730,608, dated Oct. 7, 2013, 10 pages.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 12/111,924, dated Dec. 24, 2012, 10 pages.
Notice of Allowance, U.S. Appl. No. 29/394,882, mailed Feb. 4, 2013, 32 pages.
Notice of Allowance, Design U.S. Appl. No. 29/394,882, mailed May 24, 2013, 16 pages.
Notice of Allowance, U.S. Appl. No. 11/641,569, dated Feb. 5, 2014, 11 pages.
Notice of Allowance, U.S. Appl. No. 12/111,924, mailed Mar. 11, 2013, 14 pages.
Notice of Allowance, U.S. Appl. No. 12/390,667, dated Jan. 17, 2014, 9 pages.
Notice of Allowance, U.S. Appl. No. 12/505,056, dated Mar. 6, 2014, 10 pages.
Notice of Allowance, U.S. Appl. No. 12/546,545, dated Dec. 26, 2013, 9 pages.
Notice of Allowance, U.S. Appl. No. 12/636,939, dated Oct. 7, 2013, 28 pages.
Notice of Allowance, U.S. Appl. No. 12/760,388, dated Jan. 22, 2014, 13 pages.
Notice of Allowance, U.S. Appl. No. 13/086,275, mailed Aug. 27, 2013, 31 pages.
Notice of Allowance, U.S. Appl. No. 13/374,960, mailed May 6, 2013, 20 pages.
Notice of Allowance, U.S. Appl. No. 13/573,662, mailed Mar. 19, 2013, 34 pages.
Notice of Allowance, U.S. Appl. No. 13/723,904, dated Mar. 7, 2014, 8 pages.
Notice of Allowance, U.S. Appl. No. 13/730,467, dated May 5, 2014.
Notice of Allowance, U.S. Appl. No. 13/730,585, dated Mar. 18, 2014, 10 pages.
Notice of Allowance, U.S. Appl. No. 13/730,608, dated Apr. 18, 2014.
Notice of Allowance, U.S. Appl. No. 13/731,850, dated Jun. 6, 2014.
Preliminary Amendment, U.S. Appl. No. 13/731,697, filed May 10, 2013, 6 pages.
Preliminary Amendment, U.S. Appl. No. 13/731,850, filed Apr. 11, 2014, 8 pages.
Response to Final Office Action, U.S. Appl. No. 12/546,545, filed Feb. 20, 2013, 13 pages.
Response to Final Office Action, U.S. Appl. No. 11/641,569, dated Jan. 29, 2014, 10 pages.
Response to Final Office Action, U.S. Appl. No. 11/642,385, dated Jul. 22, 2014.
Response to Final Office Action, U.S. Appl. No. 12/390,667, dated Dec. 23, 2013, 5 pages.
Response to Final Office Action, U.S. Appl. No. 12/546,545, dated Dec. 9, 2013, 8 pages.
Response to Final Office Action, U.S. Appl. No. 12/505,056, dated Feb. 26, 2014, 19 pages.
Response to Final Office Action, U.S. Appl. No. 12/636,939, filed Apr. 8, 2013, 10 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Non-Final Office Action, U.S. Appl. No. 12/390,667, filed Feb. 26, 2013, 36 pages.
Response to Non-Final Office Action, U.S. Appl. No. 11/641,569, filed Apr. 3, 2013, 9 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.

(56) References Cited

OTHER PUBLICATIONS

Response to Non-Final Office Action, U.S. Appl. No. 13/723,904, filed Nov. 6, 2013, 8 pages.
Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Response to Non-Final Office Action, U.S. Appl. No. 13/730,467, dated Apr. 11, 2014, 8 pages.
Response to Non-Final Office Action, U.S. Appl. No. 11/946,002, dated Jul. 7, 2014.
Response to Restriction Requirement, U.S. Appl. No. 12/760,388, filed Apr. 5, 2013, 7 pages.
Response to Restriction, U.S. Appl. No. 13/749,095, dated Nov. 13, 2014.
Response to Restriction, U.S. Appl. No. 13/488,505, dated May 5, 2014, 7 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.
Restriction Requirement, U.S. Appl. No. 12/760,388, mailed Mar. 6, 2013, 7 pages.
Restriction Requirement, U.S. Appl. No. 13/488,505, dated Mar. 4, 2014, 5 pages.
Restriction Requirement, U.S. Appl. No. 13/749,095, dated Sep. 25, 2014.
Supplementary European Search Report and Opinion, EP 09739474.6, dated Feb. 27, 2014, 7 pages.
Audette et al. "An algorithmic overview of surface registration techniques for medical imaging." Medical Image Analysis, vol. 4, No. 3, Sep. 1, 2000, pp. 201-217.
Banks et al. "Accurate Measurement of Three-Dimensional Knee Replacement Kinematics Using Single-Plane Fluoroscopy." *IEEE Transactions on Biomedical Engineering*, vol. 43, No. 6, Jun. 1996.
Delp et al. "An Interactive Graphics-Based Model of the lower Extremity to Study Orthopaedic Surgical Procedures." *IEEE Transactions on Biomedical Engineering*, vol. 37, No. 8, Aug. 1990.
Garg, A. et al.. "Prediction of Total Knee Motion Using a Three-Dimensional Computer-Graphics Model." *J. Biomechanics*, vol. 23, No. 1, pp. 45-58, 1990.
Ibáñez et al., The ITK Software Guide, Second Edition, Updated for ITK version 2.4, Nov. 21, 2005, pp. 114, 396-411, and 426.
Richolt et al. "Planning and Evaluation of Reorienting Osteotomies of the Proximal Femur in Cases of SCFE Using Virtual Three-Dimensional Models." *Lecture Notes in Computer Science*, vol. 1496, 1998, pp. 1-8.
Siemens MAGNETOM Sonata 1.5T Technical Specifications, pp. 1-4, accessed online Jan. 28, 2014.
Walker, P. S. et al. "Range of Motion in Total Knee Arthroplasty: A Computer Analysis." *Clinical Orthopaedics and Related Research*, No. 262, Jan. 1991.
Xie et al. "Segmentation by surface-to-image registration." proceedings of SPIE, vol. 6144, Mar. 2, 2006, pp. 614405-1-614405-7.
Calvo et al., "High Resolution MRI Detects Cartilage Swelling at the Early Stages of Experimental Osteoarthritis," OARSI, 2001, pp. 463-472.
Taylor et al., "Computer-integrated revision total hip replacement surgery: concept and preliminary results," Medical Image Analysis (1999) vol. 3, No. 3, pp. 301-319.
Amendment Under 37 CFR 1.312, U.S. Appl. No. 14/824,731, dated Dec. 28, 2015.
Australian Patent Examination Report No. 1, AU 2013200861, dated Mar. 3, 2015.
Canadian Office Action, Appl. No. 2642616, dated Apr. 22, 2015.
Canadian Office Action, CA2642616, dated Feb. 26, 2016.
Canadian Office Action, CA2708393, dated Mar. 11, 2016.
Canadian Office Action, CA2708393, dated May 7, 2015.
Canadian Office Action, CA2721735, dated Jul. 7, 2015.
Canadian Office Action, CA2721762, dated Nov. 10, 2015.
Decision on Appeal, U.S. Appl. No. 12/391,008, dated Dec. 11, 2015.
EP Communication pursuant to Article 94(3) EPC, EP10192631.9, dated Feb. 12, 2016.
EP Search Report and Opinion, EP09800841.0, dated Mar. 22, 2016.
European Examination Report, EP10192631.9, dated Feb. 11, 2015.
European Patent Office, Summons to Attend Oral Proceedings, EP07749030.8, dated Sep. 10, 2015.
European Search Report, EP09718014.5, dated May 13, 2015.
European Search Report, EP09718041.8, dated May 12, 2015.
Final Office Action, U.S. Appl. No. 11/946,002, dated Nov. 30, 2015.
Final Rejection, U.S. Appl. No. 13/749,095, dated Dec. 24, 2015.
Final Rejection, U.S. Appl. No. 14/476,500, dated Feb. 1, 2016.
Japanese Office Action, JP2014-147908, dated Jun. 9, 2015.
Non-Final Office Action, U.S. Appl. No. 13/731,697, dated Jan. 29, 2015.
Non-Final Office Action, U.S. Appl. No. 13/749,095, dated Jan. 27, 2015.
Non-Final Office Action, U.S. Appl. No. 11/946,002, dated May 18, 2016.
Non-Final Office Action, U.S. Appl. No. 11/946,002, dated Jun. 29, 2015.
Non-Final Office Action, U.S. Appl. No. 13/749,095, dated Sep. 10, 2015.
Non-Final Office Action, U.S. Appl. No. 13/923,093, dated Dec. 2, 2015.
Non-Final Office Action, U.S. Appl. No. 13/960,498, dated Feb. 9, 2016.
Non-Final Office Action, U.S. Appl. No. 14/084,255, dated Feb. 25, 2016.
Non-Final Office Action, U.S. Appl. No. 14/476,500, dated Jun. 18, 2015.
Non-Final Office Action, U.S. Appl. No. 14/869,762, dated Mar. 31, 2016.
Notice of Allowance, U.S. Appl. No. 11/656,323, dated Feb. 3, 2015.
Notice of Allowance, U.S. Appl. No. 12/391,008, dated Dec. 22, 2015.
Notice of Allowance, U.S. Appl. No. 13/731,697, dated Jul. 29, 2015.
Notice of Allowance, U.S. Appl. No. 13/749,095, dated Apr. 7, 2016.
Notice of Allowance, U.S. Appl. No. 14/476,500, dated May 19, 2016.
Notice of Allowance, U.S. Appl. No. 14/824,731, dated Oct. 20, 2015.
Reply Brief, U.S. Appl. No. 11/642,385, dated Jan. 23, 2015.
Response to Final Office Action, U.S. Appl. No. 11/946,002, dated Mar. 29, 2016.
Response to Final Office Action, U.S. Appl. No. 13/749,095, dated Feb. 17, 2016.
Response to Non-Final Office Action, U.S. Appl. No. 13/731,697, dated May 26, 2015.
Response to Non-Final Office Action, U.S. Appl. No. 13/749,095, dated Apr. 20, 2015.
Response to Non-Final Office Action, U.S. Appl. No. 11/946,002, dated Sep. 29, 2015.
Response to Non-Final Office Action, U.S. Appl. No. 13/923,093, dated May 2, 2016.
Response to Non-Final Office Action, U.S. Appl. No. 14/476,500, dated Oct. 16, 2015.
Response to Restriction, U.S. Appl. No. 14/476,500, dated Mar. 17, 2015.
Response to Restriction, U.S. Appl. No. 13/960,498, dated Nov. 19, 2015.
Restriction Requirement, U.S. Appl. No. 14/476,500, dated Feb. 25, 2015.

(56) References Cited

OTHER PUBLICATIONS

Restriction Requirement, U.S. Appl. No. 13/960,498, dated Sep. 23, 2015.
Extended European Search Report, European Appl. No. 14765072.5, dated Sep. 22, 2016.
Non-Final Office Action, U.S. Appl. No. 14/086,849, dated Nov. 2, 2016.

bML ≥ iML + ε, WHERE -2mm < ε < 5mm
bAP ≥ iAP + σ, WHERE -4mm < σ < 4mm cML ≥ jML + ω, WHERE -2mm < ω < 4mm
cAP ≥ jAP + θ, WHERE -2mm < θ < 4mm

```
┌─────────────────────────────────────────────────────────────┐
│ OBTAIN AN ASYMPTOTIC LINE-cd BY AN EXPONENTIAL FUNCTION     │
│ FROM THE ANTERIOR-DISTAL FEMUR ALONG THE ANTERIOR SIDE OF   │
│                    THE FEMORAL SHAFT.                        │
│                       [BLOCK 1050]                           │
└─────────────────────────────────────────────────────────────┘
                              ↓
┌─────────────────────────────────────────────────────────────┐
│     OBTAIN THE TANGENT CONTACT SPOT REPRESENTING THE        │
│   POSTERIOR EXTREMITY OF THE LATERAL FEMORAL CONDYLE BY     │
│   FINDING LINE-ab, WHICH IS SUBSTANTIALLY PARALLEL TO LINE-cd. │
│                       [BLOCK 1055]                           │
└─────────────────────────────────────────────────────────────┘
                              ↓
┌─────────────────────────────────────────────────────────────┐
│   OBTAIN THE ASYMPTOTIC LINE-ah BY AN ASYMPTOTIC DISTRIBUTION │
│    ALONG THE CURVATURE OF THE LATERAL EPICONDYLE UP TO THE  │
│                LATERAL EDGE OF FEMORAL SHAFT.                │
│                       [BLOCK 1060]                           │
└─────────────────────────────────────────────────────────────┘
                              ↓
┌─────────────────────────────────────────────────────────────┐
│   OBTAIN THE ASYMPTOTIC LINE-bj BY AN ASYMPTOTIC DISTRIBUTION │
│     ALONG THE CURVATURE OF THE MEDIAL EPICONDYLE UP TO THE  │
│                 MEDIAL EDGE OF FEMORAL SHAFT.                │
│                       [BLOCK 1065]                           │
└─────────────────────────────────────────────────────────────┘
                              ↓
┌─────────────────────────────────────────────────────────────┐
│ DETERMINE THE FEMORAL ANATOMICAL AXIS BY: (1) LOCATING POINT │
│  k, WHICH REPRESENTS THE CENTER OF THE DISTAL FEMUR SHAFT   │
│ AND THE LOWERMOST POINT IN THE PATELLOFEMORAL SURFACE; (2)  │
│     LOCATING POINT i, WHICH IS APPROXIMATELY AT THE MIDPOINT │
│   BETWEEN POINT h AND POINT j; AND (3) MAKING LINE ik PARALLEL TO │
│                    LINE-ah AND LINE-bj.                      │
│                       [BLOCK 1070]                           │
└─────────────────────────────────────────────────────────────┘
                              ↓
┌─────────────────────────────────────────────────────────────┐
│     DETERMINE THE LOWEST EXTREMITY OF THE MEDIAL            │
│   EPICONDYLE BY IDENTIFYING A TANGENT CONTACT SPOT VIA A    │
│   LINE-ef EXTENDING ACROSS THE TANGENT CONTACT SPOT AS      │
│            LINE-ef IS PERPENDICULAR TO LINE-ik.              │
│                       [BLOCK 1075]                           │
└─────────────────────────────────────────────────────────────┘
                              ↓
┌─────────────────────────────────────────────────────────────┐
│  DETERMINE THE RELATIONSHIP OF LINE-hi TO LINE-ij, WHERIN LINE-hi │
│     IS EQUAL TO LINE-hi PLUS m, WHERE -3mm < m < 3mm.       │
│                       [BLOCK 1080]                           │
└─────────────────────────────────────────────────────────────┘
```

FIG.5C

DETERMINE THE POSTERIOR EXTREMITY OF THE LATERAL FEMORAL CONDYLE AND THE MEDIAL FEMORAL CONDYLE AT RESPECTIVE TANGENT SPOTS A, C, WHICH ARE INTERSECTED RESPECTIVELY BY LINE-AE AND LINE-CF, WHICH ARE BOTH PARALLEL TO LINE-ab OF FIG.5A OR PLANE OF FIG.5G.
[BLOCK 1085]

↓

DETERMINE THE LOWEST OR MOST DISTAL EXTREMITY OF THE LATERAL FEMORAL CONDYLE AND THE MEDIAL FEMORAL CONDYLE AT RESPECTIVE TANGENT SPOTS B, D, WHICH ARE INTERSECTED RESPECTIVELY BY LINE-EB AND LINE-DF, WHICH ARE BOTH PARALLEL TO LINE-ef OF FIG.5B OR PLANE p OF FIG.5G.
[BLOCK 1090]

↓

USE THE RESPECTIVE TANGENT CONTACT SPOTS A, B OF THE LINE-AE AND LINE-EB, WHICH ARE TANGENTIAL TO THE ELLIPTICAL CONTOUR LINE OF THE LATERAL CONDYLE TO DEFINE THE MAJOR AND MINOR AXES OF THE LATERAL ELLIPSE CONTOUR.
[BLOCK 1095]

↓

USE THE RESPECTIVE TANGENT CONTACT SPOTS C, D OF THE LINE-CF AND LINE-DF, WHICH ARE TANGENTIAL TO THE ELLIPTICAL CONTOUR LINE OF THE MEDIAL CONDYLE, TO DEFINE THE MAJOR AND MINOR AXES OF THE MEDIAL ELLIPSE CONTOUR.
[BLOCK 1100]

FIG.6C

DETERMINE MOST POSTERIOR POINT P AND THE MOST DISTAL POINT Q OF THE LATERAL OUTER CONDYLE SURFACE VIA, RESPECTIVELY, PLANE-PS, WHICH IS TANGENTIAL TO POINT P, AND PLANE-SQ, WHICH IS TANGENTIAL TO POINT Q.
[BLOCK 1105]

DETERMINE MOST POSTERIOR POINT R AND THE MOST DISTAL POINT U OF THE MEDIAL OUTER CONDYLE SURFACE VIA, RESPECTIVELY, PLANE-RT, WHICH IS TANGENTIAL TO POINT R, AND PLANE-UT, WHICH IS TANGENTIAL TO POINT U.
[BLOCK 1110]

DEFINE THE MAJOR AXES AND MINOR AXES OF THE RESPECTIVE ELLIPTICAL CONTOURS FOR THE FEMORAL IMPLANT CONDYLES.
[BLOCK 1115]

ALIGN THE FEMORAL MODEL CONDYLES TO THE PROXIMITY OF THE CORRESPONDING FEMORAL IMPLANT CONDYLES.
[BLOCK 1120]

FIG.7D

FROM POINT A TO B   $\theta = \tan^{-1}(td/L)$

```
┌─────────────────────────────────────────────────┐
│    MEASURE THE MINIMUM CARTILAGE THICKNESS FOR  │
│    THE UNDAMAGED AND DAMAGED FEMORAL CONDYLES.  │
│                   [BLOCK 1170]                  │
└─────────────────────────────────────────────────┘
                         │
                         ▼
┌─────────────────────────────────────────────────┐
│  USE THE CARTILAGE THICKNESS MEASURED FOR THE LEAST │
│     DAMAGED CONDYLE CARTILAGE AS THE CARTLIAGE  │
│           THICKNESS REFERENCE FOR POP.          │
│                   [BLOCK 1175]                  │
└─────────────────────────────────────────────────┘
```

FIG.14C

ARTHROPLASTY SYSTEM AND RELATED METHODS

CROSS REFERENCE TO RELATED APPLICATIONS

The present application is a divisional application of U.S. application Ser. No. 12/563,809 filed Sep. 21, 2009 ("the '809 application), which application claims priority to U.S. Patent Application 61/102,692 ("the '692 application") which was filed Oct. 3, 2008 and entitled Arthroplasty System and Related Methods. The '809 application is also continuation-in-part ("CIP") application of U.S. patent application Ser. No. 11/959,344, which was filed Dec. 18, 2007, now U.S. Pat. No. 8,221,430, and entitled System and Method for Manufacturing Arthroplasty Jigs. The '809 application is also a CIP application of U.S. patent application Ser. No. 12/111,924 ("the '924 application"), which was filed Apr. 29, 2008, now U.S. Pat. No. 8,480,679, and entitled Generation of a Computerized Bone Model Representative of a Pre-Degenerated State and Useable in the Design and Manufacture of Arthroplasty Devices. The '809 application is also a CIP application of U.S. patent application Ser. No. 12/505,056 ("the '056 application"), which was filed Jul. 17, 2009 and entitled System and Method for Manufacturing Arthroplasty Jigs Having Improved Mating Accuracy. The '056 application claims priority to U.S. Patent Application 61/083,053 filed Jul. 23, 2008 and entitled System and Method for Manufacturing Arthroplasty Jigs Having Improved Mating Accuracy. The present application claims priority to all of the above-mentioned applications and hereby incorporates by reference all of the above-mentioned applications in their entireties into the present application.

FIELD OF THE INVENTION

The present invention relates to systems and methods for manufacturing customized arthroplasty cutting jigs. More specifically, the present invention relates to automated systems and methods of manufacturing such jigs.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This "eyeballing" or manual manipulation of the bone modes on the computer screen is inefficient and unnecessarily raises the time, manpower and costs associated with producing the customized arthroplasty jigs. Furthermore, a less manual approach may improve the accuracy of the resulting jigs.

There is a need in the art for a system and method for reducing the labor associated with generating customized arthroplasty jigs. There is also a need in the art for a system and method for increasing the accuracy of customized arthroplasty jigs.

SUMMARY

Various embodiments of a method of manufacturing an arthroplasty jig are disclosed herein. In a first embodiment, the method may include the following: generate a bone model, wherein the bone model includes a three dimensional computer model of at least a portion of a joint surface of a bone of a patient joint to undergo an arthroplasty procedure; generate an implant model, wherein the implant model includes a three dimensional computer model of at least a portion of a joint surface of an arthroplasty implant to be used in the arthroplasty procedure; assess a characteristic associated with the patient joint; generate a modified joint surface of the implant model by modifying at least a portion of a joint surface of the implant model according to the characteristic; and shape match the modified joint surface of the implant model and a corresponding joint surface of the bone model.

In a second embodiment, the method may include the following: generate a restored bone model, wherein the bone model includes a three dimensional computer model of at least a portion of a joint surface of a bone of a patient joint to undergo an arthroplasty procedure, wherein the restored bone model is representative of the bone in a pre-degenerated state; generate an implant model, wherein the implant model includes a three dimensional computer model of at least a portion of a joint surface of an arthroplasty implant to be used in the arthroplasty procedure; and shape match an articular joint surface of the restored bone model and a corresponding articular joint surface of the implant model.

In a third embodiment, the method may include the following: generate a bone model, wherein the bone model includes a three dimensional computer model of at least a portion of a knee joint surface of a patient femur to undergo an arthroplasty procedure; identify at least one of a most distal point and a most posterior point of a condyle articular surface of the bone model; generate an implant model, wherein the implant model includes a three dimensional computer model of at least a portion of a joint surface of a femoral arthroplasty knee implant to be used in the arthroplasty procedure; identify at least one of a most distal point and a most posterior point of a condyle articular surface of the implant model; and move at least one of the bone model and the implant model so the at least one of the most distal point and the most posterior point of the condyle articular surface of the bone model generally positionally correspond with the at least one of the most distal point and the most posterior point of the condyle articular surface of the implant model. In a variation of the third embodiment, the method may further include the following: shape match the condyle articular surface of the bone model and the articular condyle surface of the implant model.

In a fourth embodiment, the method may include the following: generate two-dimensional images of a joint surface of a patient bone; generate first data from the two-dimensional images, wherein the first data is representative of the joint surface in a deteriorated state; generate second data from the two-dimensional images, wherein the second data is representative of the joint surface in a non-deteriorated state; generate third data and fourth data positionally referenced to the third data, wherein the third data is representative of a joint surface of an arthroplasty implant and the fourth data is representative of a surgical cut plane associated with the arthroplasty implant; generate fifth data from the first data, wherein the fifth data is representative of a surface of the arthroplasty jig that will matingly receive the joint surface; generate sixth data by matching the second data and the third data, the resulting sixth data including a position of the fourth data when the second and third data are matched; generate seventh data by merging the fifth data and the sixth data; and employ the seventh data in manufacturing the arthroplasty jig from a jig blank.

An arthroplasty jig is also disclosed herein. In one embodiment, the arthroplasty jig may be for performing an arthroplasty procedure on a joint surface of a bone of a patient joint to receive an arthroplasty joint implant. In one embodiment, the arthroplasty jig may include: a mating surface configured to matingly receive the joint surface; a first saw guide oriented relative to the mating surface to result in a resection that allows the arthroplasty joint implant to restore the patient joint to a pre-degenerated alignment; and a second saw guide oriented relative to the mating surface to result in a resection that allows the arthroplasty joint implant to cause the patient joint to have an alignment approaching a zero degree mechanical axis alignment.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 5C is a flow chart illustrating the process for determining the landmark references.

FIG. 6C is a flow chart illustrating the process of determining the elliptical contours of the condyles from the landmark reference lines depicted in FIG. 5B.

FIG. 7D is a flow chart illustrating the method of determining elliptical contours and aligning respective condyles.

FIG. 14C is a flow chart illustrating the method for determining cartilage thickness used to determine proper joint line.

DETAILED DESCRIPTION

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

A. Overview of System and Method for Manufacturing Customized Arthroplasty Cutting Jigs For an overview discussion of the systems 4 for, and methods of, producing the customized arthroplasty jigs 2, reference is made to FIGS. 1A-1E.

Figure 1A:
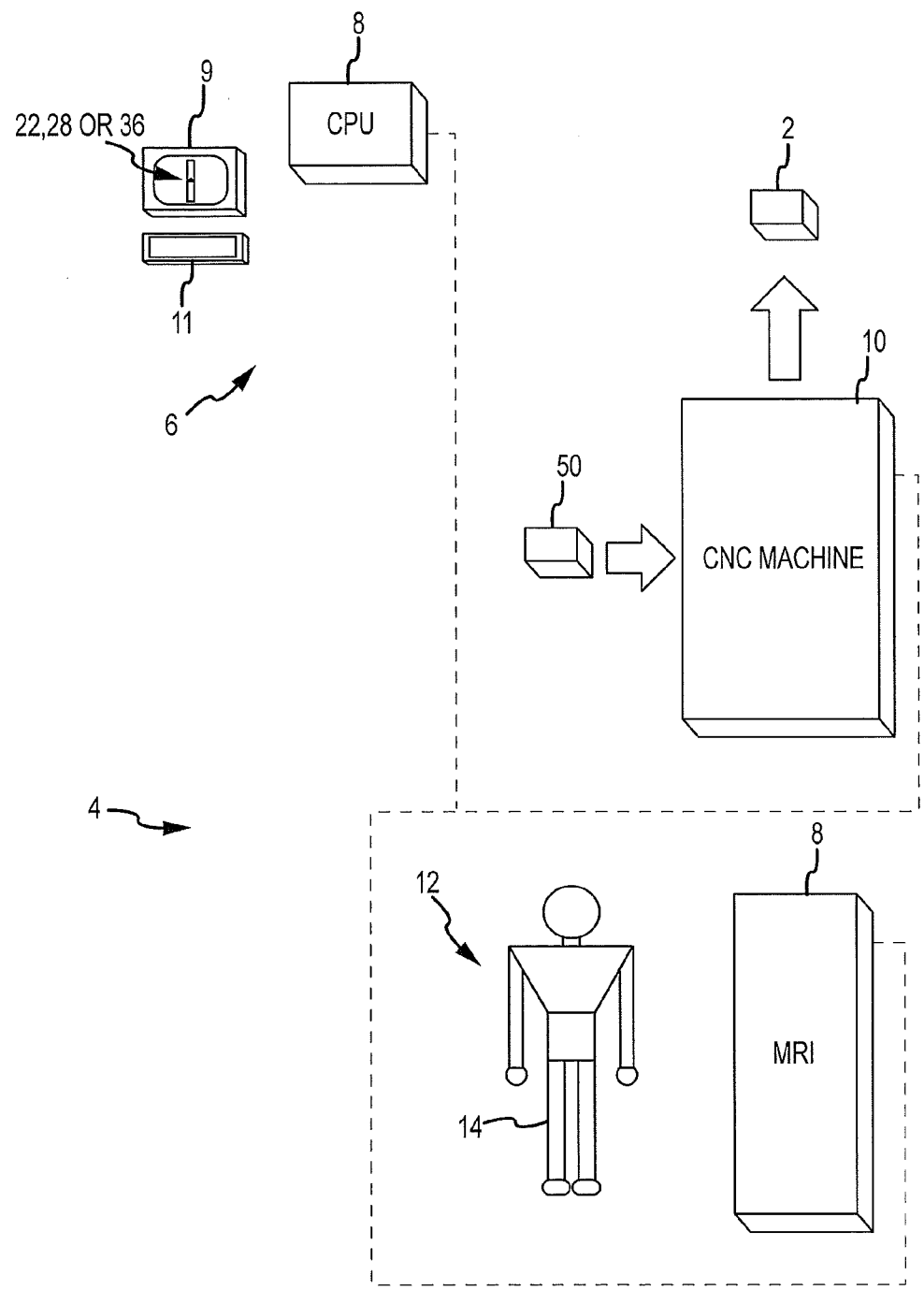
FIG. 1A is a schematic diagram of a system for employing the automated jig production method disclosed herein.

FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28. The resulting "saw cut and drill hole data" 44 is referenced to the restored bone models 28 to provide saw cuts and drill holes that will allow arthroplasty implants to restore the patient's joint to its pre-degenerated or natural alignment state.

The second section, which is discussed with respect to FIG. 1A and [blocks 100-105 and 130-145] of FIGS. 1B-1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

Figure 1B:
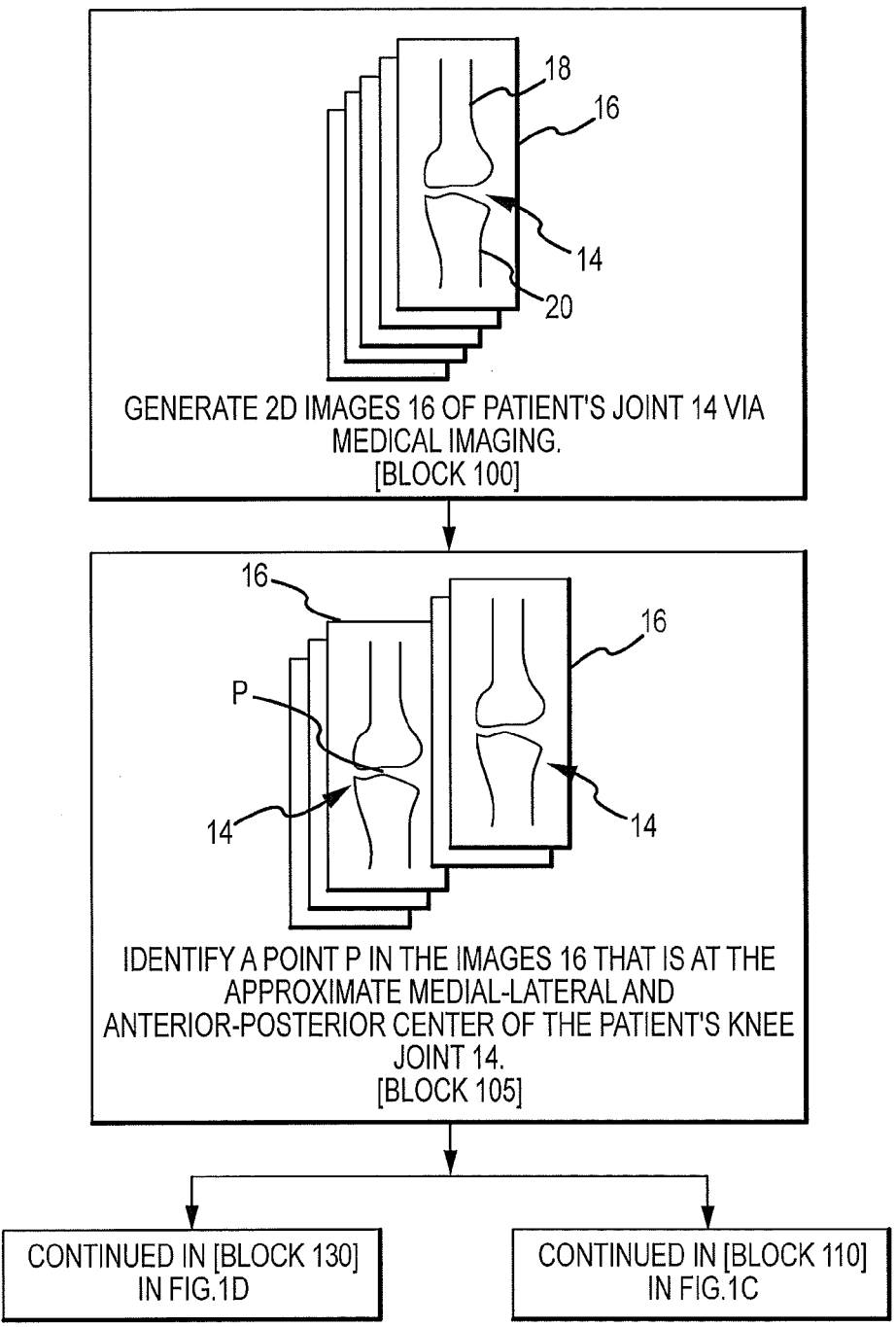
FIGS. 1B-1E are flow chart diagrams outlining the jig production method disclosed herein.
Figure 1C:
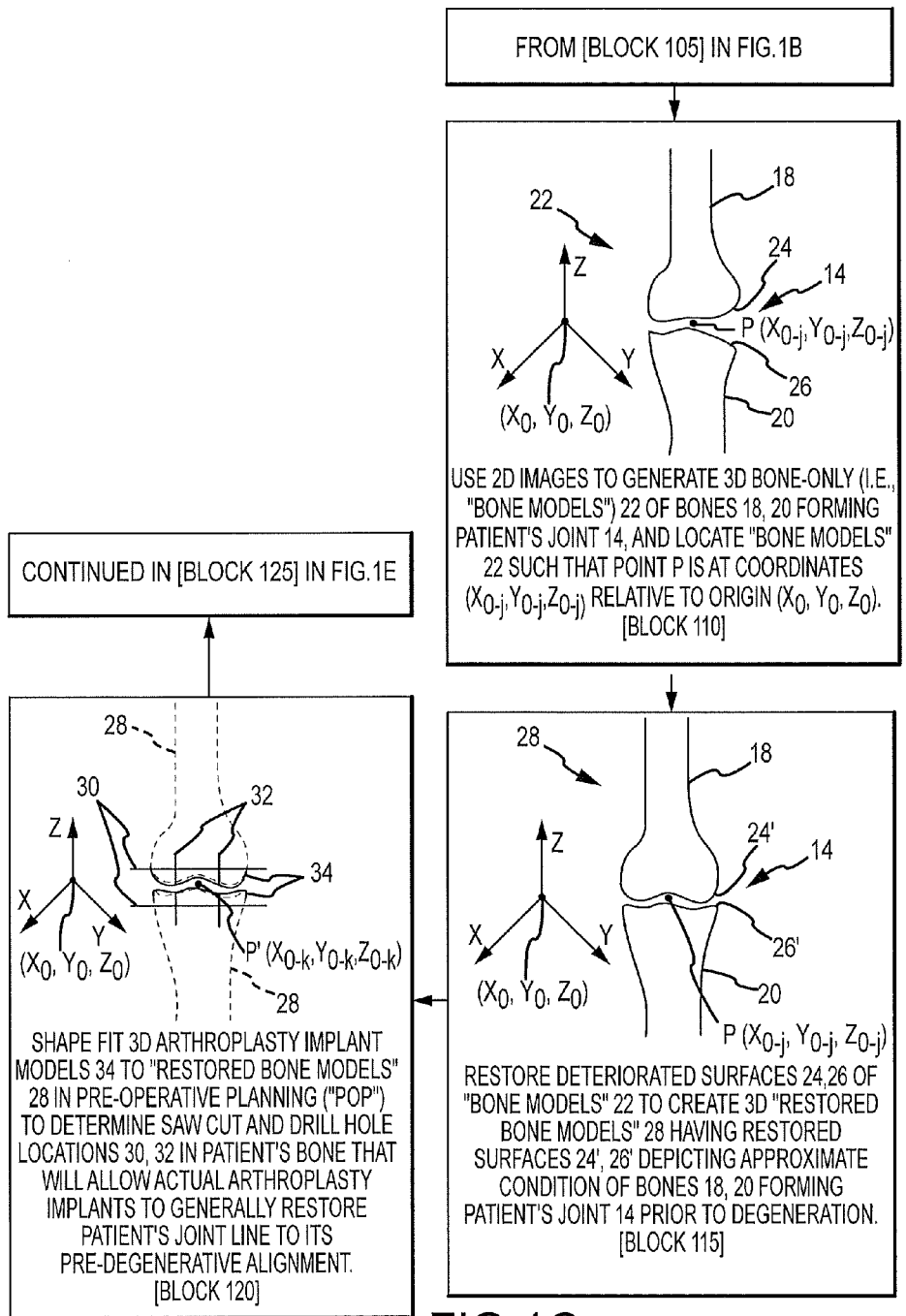
Figure 1D:
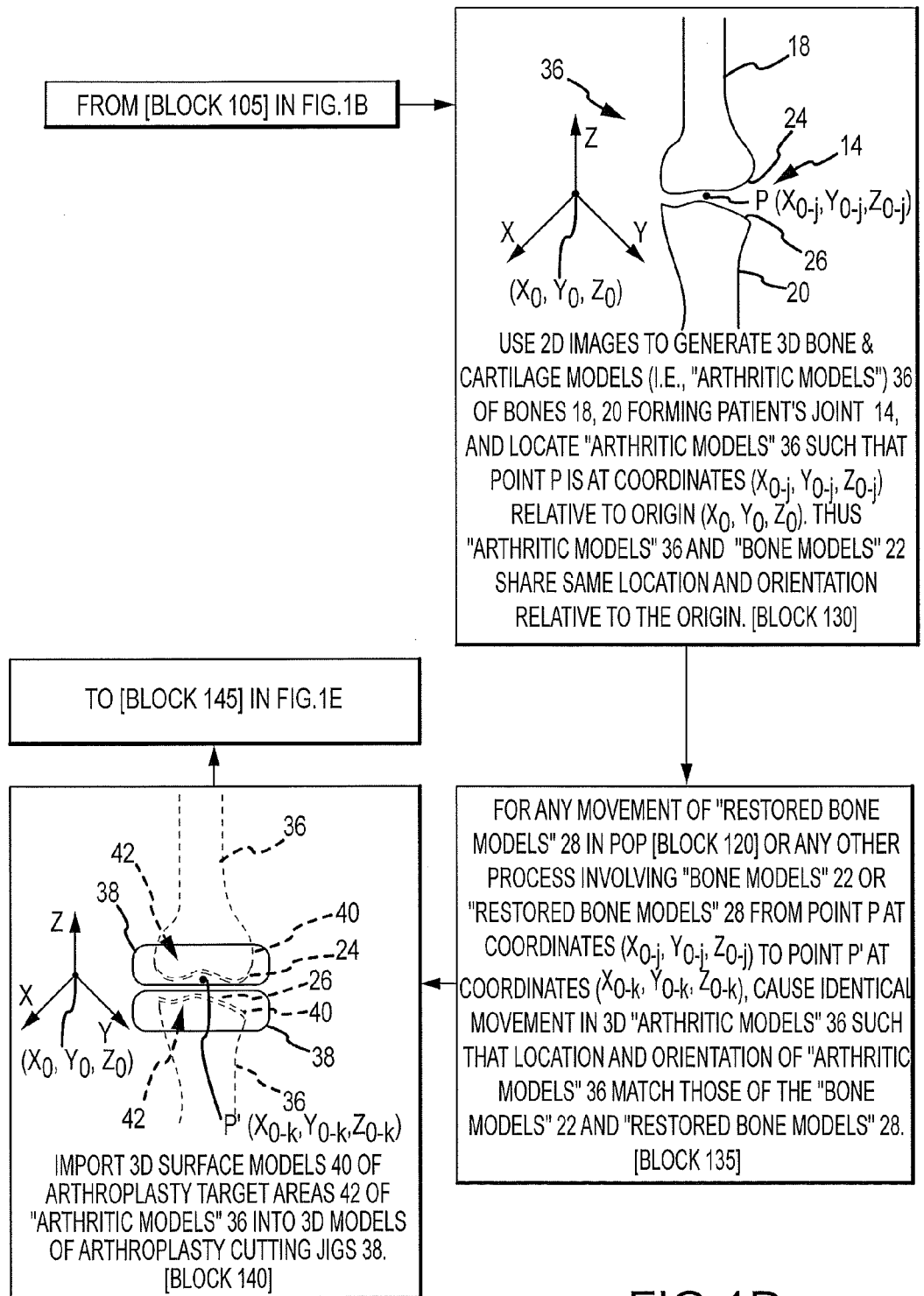
Figure 1E:
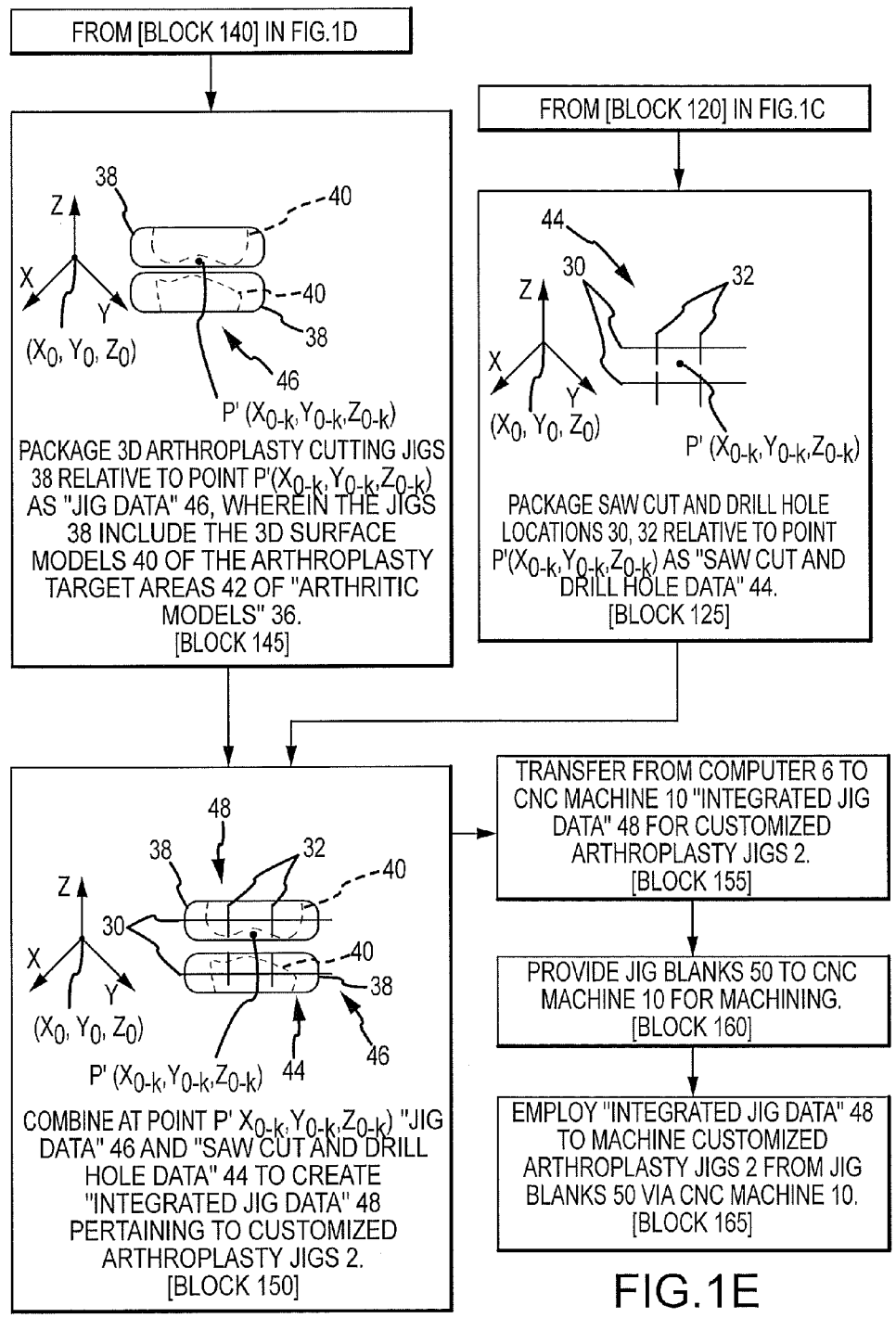

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 or other rapid production machine (e.g., a stereolithography apparatus ("SLA") machine) for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state or natural alignment state.

As shown in FIG. 1A, the system 4 includes a computer 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As shown in FIG. 1C, the 2D images 16 are employed to create computer generated 3D bone-only (i.e., "bone models") 22 of the bones 18, 20 forming the patient's joint 14 [block 110]. The bone models 22 are located such that point P is at coordinates ($X_{0-j}$, $Y_{0-j}$, $Z_{0-j}$) relative to an origin ($X_0$, $Y_0$, $Z_0$) of an X-Y-Z axis [block 110]. The bone models 22 depict the bones 18, 20 in the present deteriorated condition with their respective degenerated joint surfaces 24, 26, which may be a result of osteoarthritis, injury, a combination thereof, etc.

In one embodiment, the bone surface contour lines of the bones 18, 20 depicted in the image slices 16 may be auto segmented via a image segmentation process as disclosed in U.S. Patent Application 61/126,102, which was filed Apr. 30, 2008, is entitled System and Method for Image Segmentation in Generating Computer Models of a Joint to Undergo Arthroplasty, and is hereby incorporated by reference into the present application in its entirety.

Computer programs for creating the 3D computer generated bone models 22 from the 2D images 16 include:

Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

As indicated in FIG. 1C, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates ($X_{0-j}$, $Y_{0-j}$, $Z_{0-j}$) relative to the origin ($X_0$, $Y_0$, $Z_0$). Thus, the restored bone models 28 share the same orientation and positioning relative to the origin ($X_0$, $Y_0$, $Z_0$) as the bone models 22.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the above-described bone restoration process is generally or completely automated, as disclosed in U.S. patent application Ser. No. 12/111,924 to Park, which is entitled Generation of a Computerized Bone Model Representative of a Pre-Degenerated State and Usable in the Design and Manufacture of Arthroplasty Devices, was filed Apr. 29, 2008 and is incorporated by reference in its entirety into this Detailed Description. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state.

As depicted in FIG. 1C, the restored bone models 28 are employed in a pre-operative planning ("POP") procedure to determine saw cut locations 30 and drill hole locations 32 in the patient's bones that will allow the arthroplasty joint implants to generally restore the patient's joint line to its pre-degenerative alignment [block 120].

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. By superimposing the implant models 34 over the restored bone models 28, or vice versa, the joint surfaces of the implant models 34 can be aligned or caused to correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. For example, a computer program may manipulate computer generated 3D implant models 34 (e.g., femur and tibia implants in the context of the joint being a knee) and restored bone models or planning bone models 28 relative to each other to determine the saw cut and drill hole locations 30, 32 relative to the restored bone models 28. The implant models 34 may be superimposed over the restored bone models 28, or vice versa. In one embodiment, the implant models 34 are located at point P' ($X_{0-k}$, $Y_{0-k}$, $Z_{0-k}$) relative to the origin ($X_0$, $Y_0$, $Z_0$), and the restored bone models 28 are located at point P ($X_{0-j}$, $Y_{0-j}$, $Z_{0-j}$). To cause the joint surfaces of the models 28, 34 to correspond, the computer program may move the restored bone models 28 from point P ($X_{0-j}$, $Y_{0-j}$, $Z_{0-j}$) to point P' ($X_{0-k}$, $Y_{0-k}$, $Z_{0-k}$), or vice versa. Once the joint surfaces of the models 28, 34 are in close proximity, the joint surfaces of the implant models 34 may be shape-matched to align or correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28. A discussion of various embodiments of the automated POP process is provided later in this Detailed Description.

As indicated in FIG. 1E, in one embodiment, the data 44 regarding the saw cut and drill hole locations 30, 32 relative to point P' ($X_{0-k}$, $Y_{0-k}$, $Z_{0-k}$) is packaged or consolidated as the "saw cut and drill hole data" 44 [block 145]. The "saw cut and drill hole data" 44 is then used as discussed below with respect to [block 150] in FIG. 1E.

As can be understood from FIG. 1D, the 2D images 16 employed to generate the bone models 22 discussed above with respect to [block 110] of FIG. 1C are also used to create computer generated 3D bone and cartilage models (i.e., "arthritic models") 36 of the bones 18, 20 forming the patient's joint 14 [block 130]. Like the above-discussed bone models 22, the arthritic models 36 are located such that point P is at coordinates ($X_{0-j}$, $Y_{0-j}$, $Z_{0-j}$) relative to the origin ($X_0$, $Y_0$, $Z_0$) of the X-Y-Z axis [block 130]. Thus, the bone and arthritic models 22, 36 share the same location and orientation relative to the origin ($X_0$, $Y_0$, $Z_0$). This position/orientation relationship is generally maintained throughout the process discussed with respect to FIGS. 1B-1E. Accordingly, movements relative to the origin ($X_0$, $Y_0$, $Z_0$) of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Similar to the bone models 22, the arthritic models 36 depict the bones 18, in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 22, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{0-k}$, $Y_{0-k}$, $Z_{0-k}$) can also be imported into the jig models 38, resulting in jig models 38 positioned and oriented relative to point P' ($X_{0-k}$, $Y_{0-k}$, $Z_{0-k}$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_{0-k}$, $Y_{0-k}$, $Z_{0-k}$) into the jig models 38, resulting in the jig models 38 being indexed to matingly receive the arthroplasty target areas 42 of the arthritic models 36. The resulting jig models 38 are also positioned and oriented relative to point P' ($X_{0-k}$, $Y_{0-k}$, $Z_{0-k}$) to allow their integration with the bone cut and drill hole data 44 of [block 125].

In one embodiment, the arthritic models 36 may be 3D volumetric models as generated from the closed-loop process discussed in U.S. patent application Ser. No. 11/959,344 filed by Park. In other embodiments, the arthritic models 36 may be 3D surface models as generated from the open-loop process discussed in U.S. patent application Ser. No. 11/959,344 filed by Park.

In one embodiment, the models 40 of the arthroplasty target areas 42 of the arthritic models 36 may be generated via an overestimation process as disclosed in U.S. Provisional Patent Application 61/083,053, which is entitled System and Method for Manufacturing Arthroplasty Jigs Having Improved Mating Accuracy, was filed by Park Jul. 23, 2008, and is hereby incorporated by reference in its entirety into this Detailed Description.

As indicated in FIG. 1E, in one embodiment, the data regarding the jig models 38 and surface models 40 relative to point P' ($X_{0-k}$, $Y_{0-k}$, $Z_{0-k}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state or natural alignment state.

As can be understood from FIGS. 1A and 1E, the "integrated jig data" 48 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

Figure 1F:
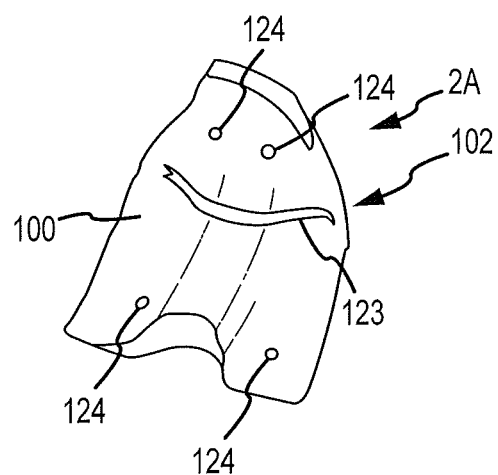
FIGS. 1F and 1G are, respectively, bottom and top perspective views of an example customized arthroplasty femur jig.
Figure 1G:
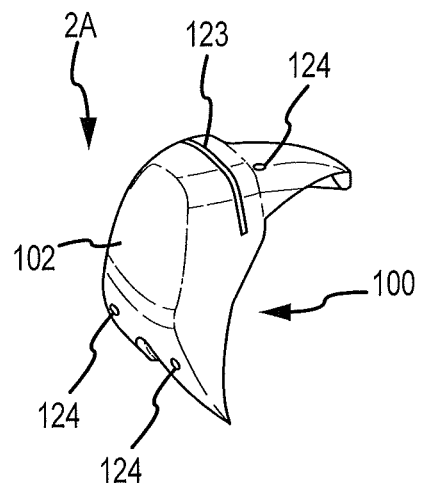
Figure 1H:
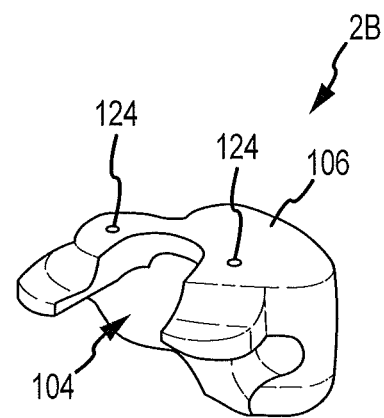
FIGS. 1H and 1I are, respectively, bottom and top perspective views of an example customized arthroplasty tibia jig.
Figure 1I:
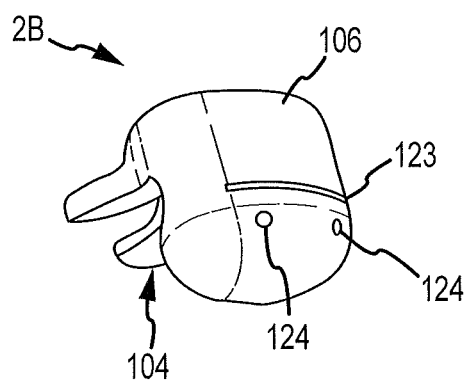

For a discussion of example customized arthroplasty cutting jigs 2 capable of being manufactured via the above-discussed process, reference is made to FIGS. 1F-1I. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 1F-1I are for total knee replacement ("TKR") or partial knee ("uni-knee") replacement procedures. Thus, FIGS. 1F and 1G are, respectively, bottom and top perspective views of an example customized arthroplasty femur jig 2A, and FIGS. 1H and 1I are, respectively, bottom and top perspective views of an example customized arthroplasty tibia jig 2B.

As indicated in FIGS. 1F and 1G, a femur arthroplasty jig 2A may include an interior side or portion 100 and an exterior side or portion 102. When the femur cutting jig 2A is used in a TKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 1H and 1I, a tibia arthroplasty jig 2B may include an interior side or portion 104 and an exterior side or portion 106. When the tibia cutting jig 2B is used in a TKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20.

While the discussion provided herein is given in the context of TKR and TKR jigs and the generation thereof. However, the disclosure provided herein is readily applicable to uni-compartmental or partial arthroplasty procedures in the knee or other joint contexts. Thus, the disclosure provided herein should be considered as encompassing jigs and the generation thereof for both total and uni-compartmental arthroplasty procedures.

The remainder of this Detailed Discussion will now focus on various embodiments for performing POP.

B. Overview of Preoperative Planning ("POP") Procedure

Figure 1J:
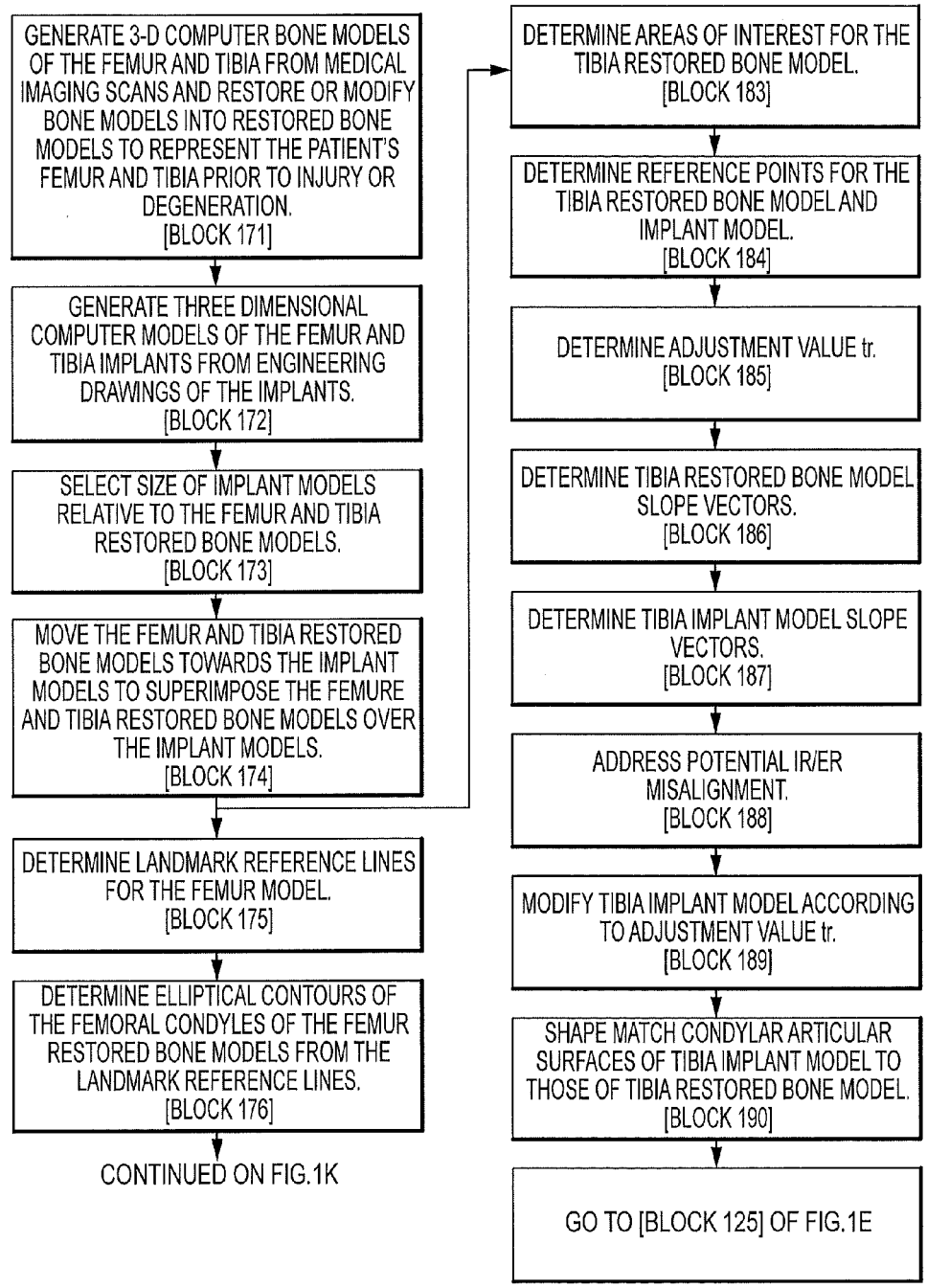
FIGS. 1J and 1K contain portions of a flow chart illustrating an overview of the POP system and method disclosed herein.
Figure 1K:
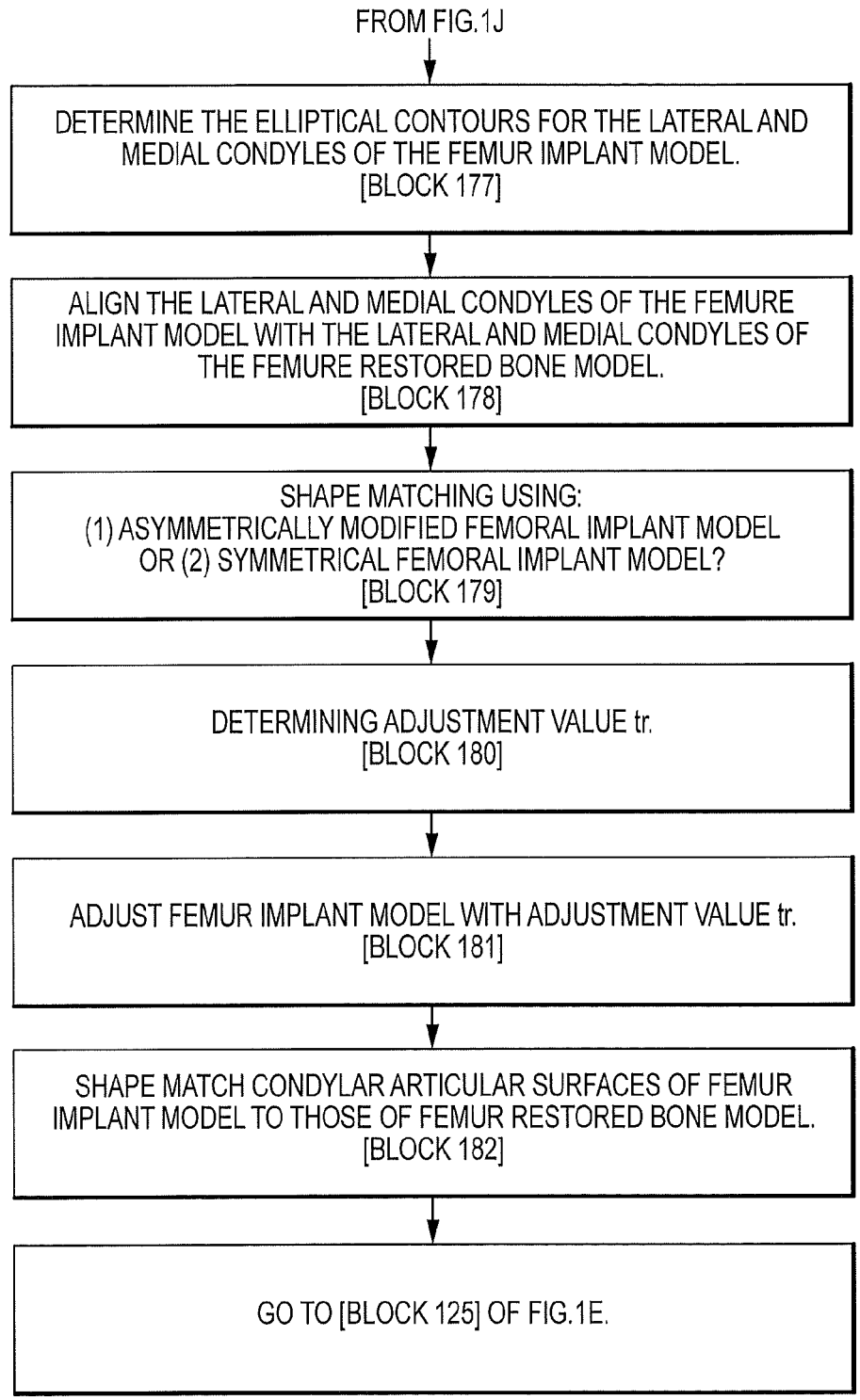

In one embodiment, as can be understood from [blocks 100-120] of FIGS. 1B-1C and from FIGS. 1J and 1K, which contain portions of a flow chart illustrating an overview of the POP system and method disclosed herein, medical images 16 of the femur and tibia 18, 20 are generated and formed into three dimensional ("3D") bone models 22, which are then restored or modified into restored bone models 28', 28" to represent the patient's femur and tibia 18, 20 prior to injury or degeneration [block 171]. Three dimensional computer models 34', 34" of the femur and tibia implants are generated from engineering drawings of the implants and may be generated via any of the above-referenced 3D modeling programs [block 172]. The sizes of the implant models 34', 34" are selected relative to the femur and tibia restored bone models 28', 28" [block 173]. The femur and tibia restored bone models 28', 28" are moved towards the implant models 34', 34" to superimpose the femur and tibia restored bone models 28', 28" over the implant models 34', 34" [block 174]. Landmark reference lines for the femur restored bone model 28' are determined [block 175]. The elliptical contours of the femoral condyles 430, 445 are determined from the landmark reference lines [block 125]. The elliptical contours 505, 510 for the lateral and medial condyles 515, 520 of the femur implant model 34' are determined [block 176]. The lateral and medial condyles 515, 520 of the femur implant model 34' are aligned with the lateral and medial condyles 430, 445 of the femur restored bone model 28' [block 177]. The superposing of the femur restored bone model 28' with the implant model 34' is refined by aligning the condyles of the of the femur restored bone model 28' with the condyles of the implant model 34' [block 178]. An asymmetrical or symmetrical femoral implant model 34' is selected for the shape matching process [block 179]. An adjustment value tr is determined to account for cartilage thickness or joint gap of a restored joint [block 180]. The implant model 34' is modified according to the adjustment value tr [block 181]. The shape matching process takes place where the articular condylar surfaces of the modified implant model 34' are shape matched to the articular condylar surfaces of the restored bone model 28'. The process then continues as indicated in [block 125] of FIG. 1E.

As indicated in FIG. 1J with respect to the tibia, areas of interest are identified for the tibia restored model [block 183]. Reference points are identified for the tibia restored bone model and the tibia implant model [block 184]. An adjustment value tr is determined for the tibia implant model [block 185]. Slope vectors are identified for the tibia restored bone model [block 186] and the tibia implant model [block 187]. Potential IR/ER misalignment is addressed [block 188]. The tibia implant model is modified according to the adjustment value tr [block 189]. The condylar articular surfaces of tibia implant model are shape matched to those of the tibia restored bone model [block 190].

This ends the overview of the POP process. The following discussions will address each of the aspects of the POP process in detail.

C. Computer Modeling Femur and Tibia

Figure 2A:
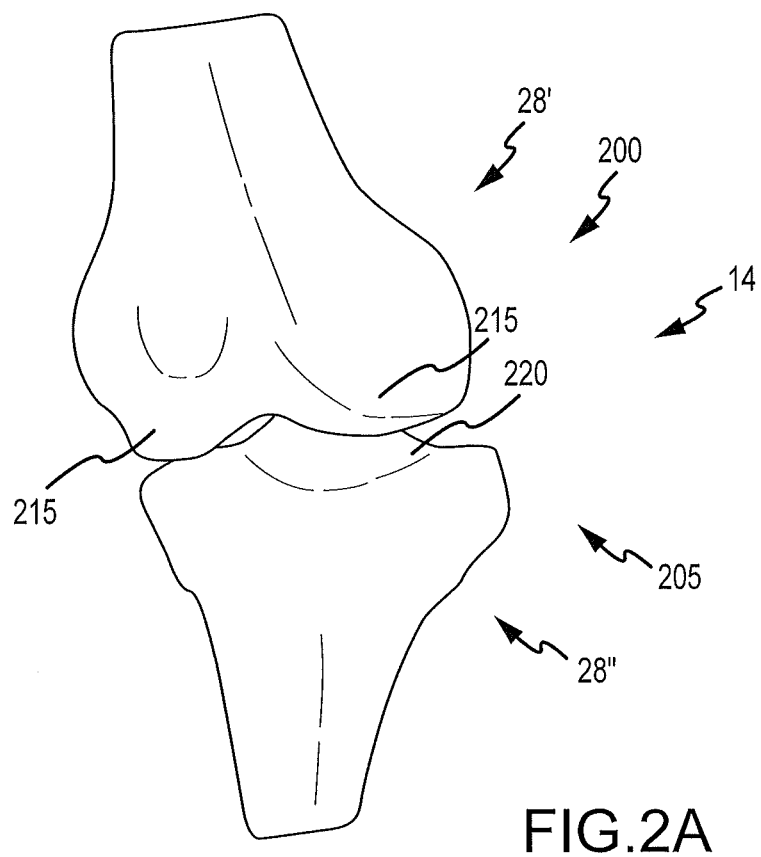
FIG. 2A is an isometric view of a 3D computer model of a femur lower end and a 3D computer model of a tibia upper end in position relative to each to form a knee joint and representative of the femur and tibia in a non-degenerated state.

FIG. 2A depicts 3D computer generated restored bone models 28', 28" of the femur and tibia 18, 20 generated from medical imaging scans 16 and representing the patient's femur 18 and tibia 20 prior to injury or degeneration [see block 171 of FIG. 1J]. More specifically, FIG. 2A is an isometric view of a 3D computer model 28' of a femur lower end 200 and a 3D computer model 28" of a tibia upper end 205 representative of the corresponding patient bones 18, 20 in a non-deteriorated state and in position relative to each to form a knee joint 14. The femur lower end 200 includes condyles 215, and the tibia upper end 205 includes a plateau 220. The models 28', 28" are positioned relative to each other such that the curved articular surfaces of the condyles 215, which would normally mate with complementary articular surfaces of the plateau 220, are instead not mating, but roughly positioned relative to each other to generally for the knee joint 14.

As generally discussed above with respect to FIGS. 1A-1C, the POP begins by using a medical imaging process, such as magnetic resonance imaging (MRI), computed tomography (CT), and/or another other medical imaging process, to generate imaging data of the patient's knee. The generated imaging data is sent to a preoperative planning computer program. Upon receipt of the data, the computer program converts the data (e.g., two-dimensional MRI images 16) into 3D anatomical computer bone models 22 of the knee joint 14 with the aid of a medical imaging conversion computer program, the bone models 22 being representative of the patient's bones 18, 20 in the current deteriorated state. For example, current commercially available MRI machines use 8 bit (255 grayscale) to show the human anatomy. Therefore, certain components of the knee, such as the cartilage, cortical bone, cancellous bone, meniscus, etc., can be uniquely viewed and recognized with 255 grayscale.

As provided in U.S. patent application Ser. No. 12/111,924 to Park, which is entitled Generation of a Computerized Bone Model Representative of a Pre-Degenerated State and Usable in the Design and Manufacture of Arthroplasty Devices, was filed Apr. 29, 2008 and is incorporated by reference in its entirety into this Detailed Description, specialized medical converging software recognizes the anatomy of the knee and shapes the bone models 22 using mathematical algorithms, such as sequences of $n^{th}$ order polynomials, where n is greater than or equal to 3. A technique such as surface-rendering is then used to construct 3D restored bone models 28', 28" of the knee joint 14 from the bone models 22. Examples of medical imaging computer programs that may be used here include Analyze (from AnalyzeDirect, Inc., Overland Park, Kans.), open-source software such as the Insight Toolkit (ITK, www.itk.org) and 3D Slicer (www.slicer.org), and Mimics (from Materialise, Ann Arbor, Mich.).

In one embodiment, the resulting 3D restored bone models 28', 28" of the femur portion 200 and tibia portion 205 forming the knee joint 14 include the cortical bone of the femur 18 and the tibia 20. Depending on the embodiment, the restored bone models 28', 28" may includes articular cartilage attached to the distal region of the femur 18 and the proximal region of the tibia 20. The computer program may automatically exclude the rest of the soft tissue, as well as the cancellous bone, from the 3D computer models 28', 28", although in some variations the computer program may not automatically exclude the rest of the soft tissue and/or the cancellous bone.

The 3D computer generated femur and tibia restored bone models 28', 28" are repaired versions of the patient's femur 18 and tibia 20 as these bones are believed to have existed before degenerating into their current existing date, the current state of the patient's femur 18 and tibia 20 being represented by the 3D bone models 22. In other words, the femur and tibia computer generated bone models 22 resulting from the MRI scans depict the femur 18 and tibia 20 in the current deteriorated state. These models 22 are then modified or restored into restored bone models 28', 28" to represent the femur 18 and tibia 20 as they likely appeared before beginning to degenerate. The resulting modified or restored models 28', 28" can then be used for planning purposes, as described later in this Detailed Description.

For greater detail regarding the methods and systems for computer modeling joint bones, such as the femur and tibia bones forming the knee, please see the following U.S. patent applications, which are all incorporated herein in their entireties: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; U.S. patent Ser. No. 11/642,385 to Park et al., titled "Arthroplasty Devices and Related Methods" and filed Dec. 19, 2006; and U.S. patent application Ser. No. 12/111,924 to Park, titled "Generation of a Computerized Bone Model Representative of a Pre-Degenerated State and Usable in the Design and Manufacture of Arthroplasty Devices" and filed Apr. 29, 2008.

Figure 2B:
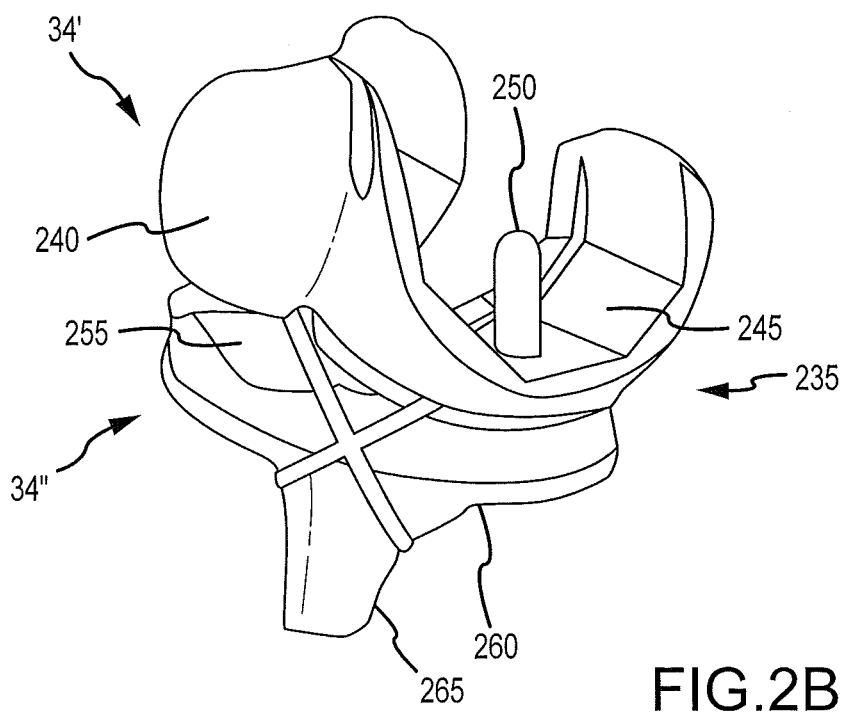
FIG. 2B is an isometric view of a 3D computer model of a femur implant and a 3D computer model of a tibia implant in position relative to each to form an artificial knee joint.

FIG. 2B is an isometric view of a computer model of a femur implant 34' and a computer model of a tibia implant 34" in position relative to each to form an artificial knee joint 14. The computer models 34', 34" may be formed, for example, via computer aided drafting or 3D modeling programs [see block 172 of FIG. 1J].

The femur implant model 34' will have a joint side 240 and a bone engaging side 245. The joint side 240 will have a condoyle-like surface for engaging a complementary surface of the tibia implant model 34". The bone engaging side 245 will have surfaces and engagement features 250 for engaging the prepared (i.e., sawed to shape) lower end of the femur 18.

The tibia implant model 34" will have a joint side 255 and a bone engaging side 260. The joint side 255 will have a plateau-like surface configured to engage the condoyle-like surface of the femur implant model 34'. The bone engaging side 260 will have an engagement feature 265 for engaging the prepared (i.e., sawed to shape) upper end of the tibia 20.

As discussed in the next subsection of this Detailed Description, the femur and tibia restored bone models 28', 28" may be used in conjunction with the implant models 34', 34" to select the appropriate sizing for the implants actually to be used for the patient.

D. Selecting the Sizes for the Femoral and Tibial Implants

Figures 3A, 3B:
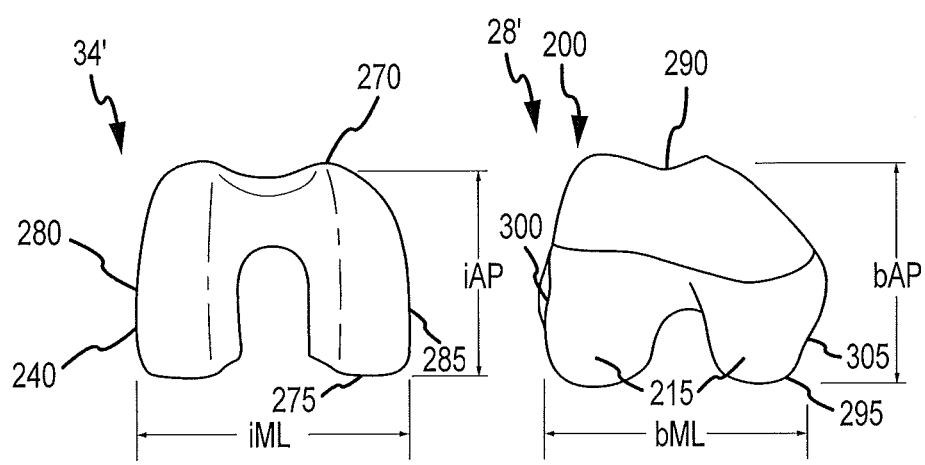
FIG. 3A is a plan view of the joint side of the 3D femur implant model depicted in FIG. 2B.
FIG. 3B is an axial end view of the lower end of the 3D computer model of the femur depicted in FIG. 2A and showing the condoyle surfaces.

FIG. 3A is a plan view of the joint side 240 of the femur implant model 34' depicted in FIG. 2B. FIG. 3B is an axial end view of the femur lower end 200 of the femur restored bone model 28' depicted in FIG. 2A and showing the condoyle surfaces 215. The views depicted in FIGS. 3A and 3B are used to select the proper size for the femoral implant model 34' [see block 173 of FIG. 1J].

As can be understood from FIG. 3A, each femoral implant available via the various implant manufactures may be represented by a specific femoral implant 3D computer model 34' having a size and dimensions specific to the actual femoral implant. Thus, the representative implant model 34' of FIG. 3A may have an associated size and associated dimensions in the form of, for example, an anterior-posterior extent iAP and medial-lateral extent iML. These implant extents iAP, iML may be compared to the dimensions of the femur restored bone model 28' that represents the patient's femur 18 as it may have existed prior to degeneration or injury. For example, the femur restored bone model 28' may have dimensions such as, for example, an anterior-posterior extent bAP and a medial-lateral extent bML, as shown in FIG. 3B. In FIG. 3A, the anterior-posterior extent iAP of the femoral implant model 34' is measured from the anterior edge 270 to the posterior edge 275 of the femoral implant model 34', and the medial-lateral extent iML is measured from the medial edge 280 to the lateral edge 285 of the femoral implant model 34'.

Each patient has femurs that are unique in size and configuration from the femurs of other patients. Accordingly, each femur restored bone model 28' will be unique in size and configuration to match the size and configuration of the femur medically imaged. As can be understood from FIG. 3B, the femoral anterior-posterior length bAP is measured from the anterior edge 290 of the patellofemoral groove to the posterior edge 295 of the femoral condyle, and the femoral medial-lateral length bML is measured from the medial edge 300 of the medial condyle to the lateral edge 305 of the lateral condyle.

Figure 3C:
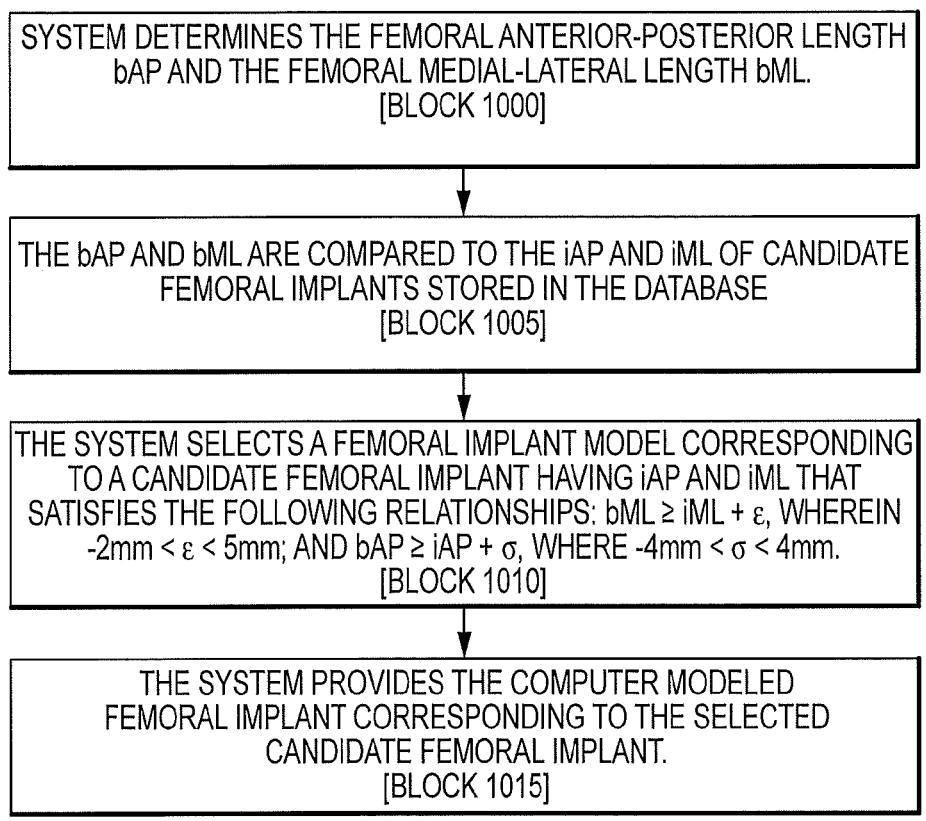
FIG. 3C is a flow chart depicting the process undertaken by the system when selecting the appropriate femur implant size.

As can be understood from FIG. 3C, which is a flow chart depicting the process undertaken by the system 4 when selecting the femur implant model 34' corresponding to the appropriate femur implant size to be used in the actual arthroplasty procedure, the system 4 determines the femoral anterior-posterior length bAP and the femoral medial-lateral length bML for, the femur restored bone model 28' [block 1000].

In one embodiment, there is a limited number of sizes of a candidate femoral implant. For example, one manufacturer may supply six sizes of femoral implants and another manufacturer may supply eight or another number of femoral implants. The iAP and iML dimensions of these candidate implants may be stored in a database. The bAP and bML are compared to the iAP and iML of candidate femoral implants stored in the database [block 1005]. The system 4 selects a femoral implant model 34' corresponding to a candidate femoral implant having iAP and iML that satisfies the following two relationships: bML≥iML+ϵ, wherein −2 mm<ϵ<5 mm; and bAP≥iAP+σ, where −4 mm<σ<4 mm [block 1010]. As an alternative to [block 1010], in one embodiment, instead of selecting from a limited number of candidate femoral implants, these two relationships are used to manufacture a custom sized femoral implant.

Still referring to FIG. 3C and continuing from [block 1010], the system 4 provides the computer modeled femoral implant 34' corresponding to the selected candidate femoral implant [block 1015]. This computer modeled femoral implant 34', which corresponds to the selected candidate femoral implant, is used with the computer modeled femur restored bone model 28' in computer modeling a femoral arthroplasty jig, as discussed later in this Detailed Description.

Figure 3E:
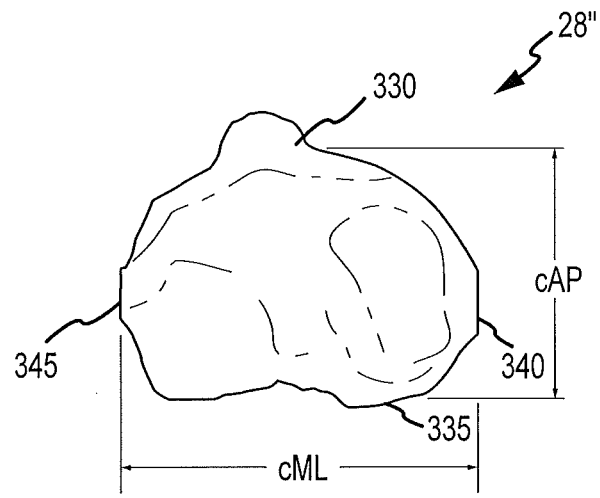
FIG. 3E is an axial end view of the upper end of the 3D computer model of the tibia depicted in FIG. 2A and showing the plateau.
Figure 3D:
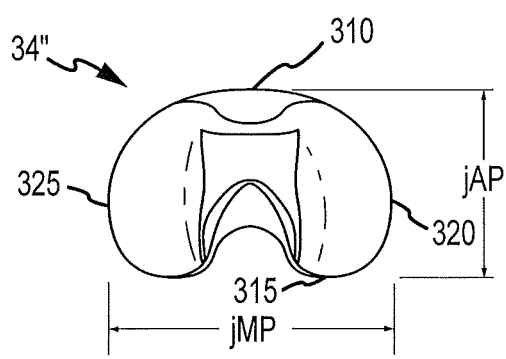
FIG. 3D is a plan view of the joint side of the 3D tibia implant model depicted in FIG. 2B.

FIG. 3D is a plan view of the joint side 255 of the tibia implant model 34" depicted in FIG. 2B. FIG. 3E is an axial end view of the tibia upper end 205 of the tibia restored bone model 28" of FIG. 2A and showing the plateau 220. The views depicted in FIGS. 3D and 3E are used to select the proper size for the tibial implant model 34".

As can be understood from FIG. 3D, each tibial implant available via the various implant manufactures may be represented by a specific tibia implant 3D computer model 34" having a size and dimensions specific to the actual tibia implant. Thus, the representative implant model 34" of FIG. 3D may have an associated size and associated dimensions in the form of, for example, anterior-posterior extent cAP and the medial-lateral extent cML of the tibia model 34", as shown in FIG. 3E. In FIG. 3D, the anterior-posterior extent jAP of the tibia implant model 34" is measured from the anterior edge 310 to the posterior edge 315 of the tibial implant model 34", and the medial-lateral extent jML is measured from the medial edge 320 to the lateral edge 325 of the tibial implant model 34".

Each patient has tibias that are unique in size and configuration from the tibias of other patients. Accordingly, each tibia restored bone model 28" will be unique in size and configuration to match the size and configuration of the tibia medically imaged. As can be understood from FIG. 3E, the tibial anterior-posterior length cAP is measured from the anterior edge 330 of the of the tibial restored bone model 28" to the posterior edge 335 of the tibial restored bone model 28", and the tibial medial-lateral length cML is measured from the medial edge 340 of the medial plateau of the tibia restored bone model 28" to the lateral edge 345 of the lateral plateau of the tibia restored bone model 28".

Figure 3F:
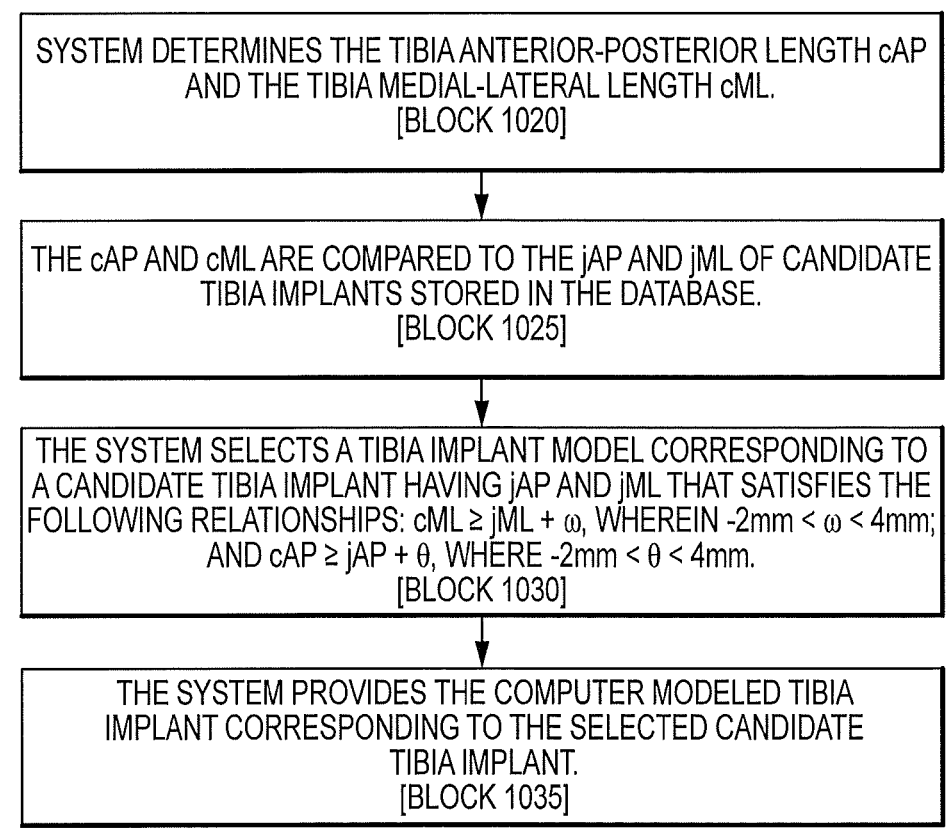
FIG. 3F is a flow chart depicting the process undertaken by the system when selecting the appropriate tibia implant size.

As can be understood from FIG. 3F, which is a flow chart depicting the process undertaken by the system 4 when selecting the tibia implant model 34" corresponding to the appropriate tibia implant size to be used in the actual arthroplasty procedure, the system 4 determines the tibial anterior-posterior length cAP and the tibial medial-lateral length cML [block 1020].

In one embodiment, there is a limited number of sizes of a candidate tibia implant. For example, one manufacturer may supply six sizes of tibia implants and another manufacturer may supply eight or another number of tibia implants. The jAP and jML dimensions of these candidate implants may be stored in a database. The cAP and cML are compared to the jAP and jML of candidate tibia implants stored in the database [block 1025]. The system 4 selects a tibia implant model 34" corresponding to a candidate tibia implant having jAP and jML that satisfies the following two relationships: cML≥jML+ω, wherein −2 mm<ω<4 mm; and cAP≥jAP+θ, where −2 mm<θ<4 mm [block 1030]. As an alternative to [block 1030], in one embodiment, instead of selecting from a limited number of candidate tibia implants, these two relationships are used to manufacture a custom sized tibia implant.

Still referring to FIG. 3F and continuing from [block 1030], the system 4 provides the computer modeled tibia implant 34" corresponding to the selected candidate tibia implant [block 1035]. This computer modeled tibia implant 34", which corresponds to the selected candidate tibia implant, is used with the computer modeled tibia restored bone model 28" in computer modeling a tibia arthroplasty jig, as discussed later in this Detailed Description.

Femoral and tibial implants represented by the implant models 34', 34", such as those depicted in FIG. 2B, are commercially available. Examples of commercially available implants include the Vanguard™ prosthetic femoral arthroplasty implants (manufactured by Biomet, Inc.), the Triathlon® Knee System (from Stryker® Orthopedics), and the P.F.C.® Sigma Knee System (from Depuy).

E. Moving Femur and Tibia Models Towards Corresponding Implant Models Such That Femur and Tibia Models are Superimposed Over the Implant Models.

As explained above with respect to [blocks 100-115] of FIGS. 1A-1C, the restored bone models 28', 28" can be reconstructed from bone models 22 generated from the plurality of MRI image slices 16, which are scanned around a live patient's knee 14. As can be understood from [blocks 100-115] of FIGS. 1A-1C, the image slices 16, bone models 22 and restored bone models 28 may be positioned at a coordinate point $P\ (X_{0\text{-}j},\ Y_{0\text{-}j},\ Z_{0\text{-}j})$ relative to an origin $X_0$, $Y_0$, $Z_0$ of an X-Y-Z axis throughout their respective generations and existences. Similarly, the implant models 34 may be positioned at a coordinate point $P\ (X_{0\text{-}k},\ Y_{0\text{-}k},\ Z_{0\text{-}k})$ relative to the origin $X_0$, $Y_0$, $Z_0$ of the X-Y-Z axis throughout their existence. Thus, as indicated in FIG. 4A, which is an isometric view of the restored bone models 28 and implant models 34, the restored bone models 28 may be positioned such that a point $P_{RBM}$ associated with the restored bone models 28 occupies coordinate point $P\ (X_{0\text{-}j},\ Y_{0\text{-}j},\ Z_{0\text{-}j})$ relative the origin $X_0$, $Y_0$, $Z_0$ of the X-Y-Z axis, and the implant models 34 may be positioned such that a point $P_{IM}$ associated with the implant models 34 occupies coordinate point $P\ (X_{0\text{-}k},\ Y_{0\text{-}k},\ Z_{0\text{-}k})$ relative the origin $X_0$, $Y_0$, $Z_0$ of the X-Y-Z axis.

Figure 4A:
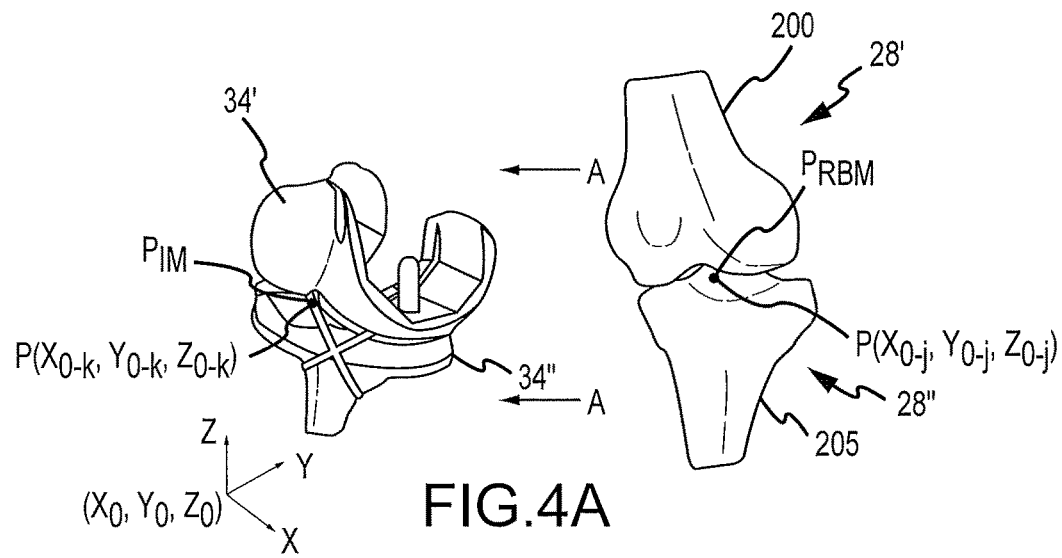
FIG. 4A shows the restored bone models depicted in FIG. 2A positioned away from the implant models depicted in FIG. 2B, but being moved towards the implant models.
Figure 4B:
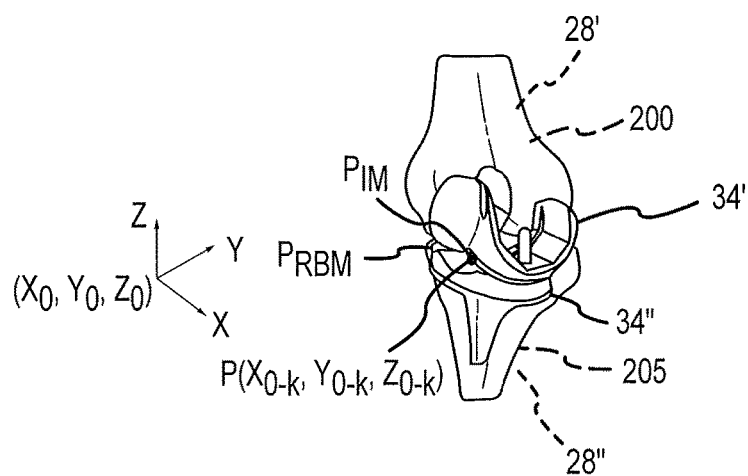
FIG. 4B is an isometric view of the femur and tibia restored bone models superimposed over the femur and tibia implant models.

As indicated by arrows A in FIG. 4A, the restored bone models 28 and implant models 34 may be moved together to superimpose one type of model over the other type of model. For example, in one embodiment, the implant models 34 are held stationary at coordinate point $P\ (X_{0\text{-}k},\ Y_{0\text{-}k},\ Z_{0\text{-}k})$ and, as indicated by arrows A, the restored bone models 28 are moved from coordinate point $P\ (X_{0\text{-}j},\ Y_{0\text{-}j},\ Z_{0\text{-}j})$ to coordinate point $(X_{0\text{-}k},\ Y_{0\text{-}k},\ Z_{0\text{-}k})$ such that point $P_{RBM}$ of the restored bone models 28 moves from coordinate point $P\ (X_{0\text{-}j},\ Y_{0\text{-}j},\ Z_{0\text{-}j})$ to coordinate point $(X_{0\text{-}k},\ Y_{0\text{-}k},\ Z_{0\text{-}k})$. As a result and as indicated in FIG. 4B, which is an isometric view of the restored bone models 28 superimposed over the implant models 34, points $P_{RBM}$ and $P_{IM}$ end up both being generally occupying coordinate point ($X_{0-k}$, $Y_{0-k}$, $Z_{0-k}$) such that the models 28, 34 are superimposed.

As mentioned above with respect to the discussion of [block 135] of FIG. 1D, movement of the restored bone models 28 during the POP or other process from coordinate point P ($X_{0-j}$, $Y_{0-j}$, $Z_{0-j}$) to another coordinate point, such as, coordinate point ($X_{0-k}$, $Y_{0-k}$, $Z_{0-k}$), is reflected or mimicked by the arthritic models 36 such that the location and orientation of the arthritic models 36 matches those of the restored bone models 28, thereby facilitating the combining of the data types 44, 46 into the integrated jig data 48, as discussed in [block 150] of FIG. 1E.

In one embodiment, the point $P_{IM}$ associated with the implant models 34 is located between the implant models 34', 34" close to their centers, near the intercondylar notch of the femur implant model 34', and the point $P_{RBM}$ associated with the restored bone models 28 is located between the restored bone models 28', 28" close to their centers, near the intercondylar notch of the femur restored bone model 28'. Of course, depending on the embodiment, the points $P_{IM}$, $P_{RBM}$ may be located at other locations relative to their respective models 34, 28 as long as the locations of the points $P_{IM}$, $P_{RBM}$ relative to their respective models 34, 28 are generally coordinated with each other. For example, points $P_{IM}$, $P_{RBM}$ could be positioned relative to their respective models 34, 28 such that the points $P_{IM}$, $P_{RBM}$ are generally centered at the most distal point of the medial articular condylar surface of each respective model 34, 28.

The preceding example is given in the context of holding the implant models 34 in place and moving the restored bone models 28 to the implant models 34 to superimpose the restored bone models 28 over the implant models 34. However, in other embodiments, the reverse situation may be the case, wherein the restored bone models 28 are held in place and the implant models 34 are moved to the restored bone models 28 to superimpose the implant models 34 over the restored bone models 28.

Figure 4C:
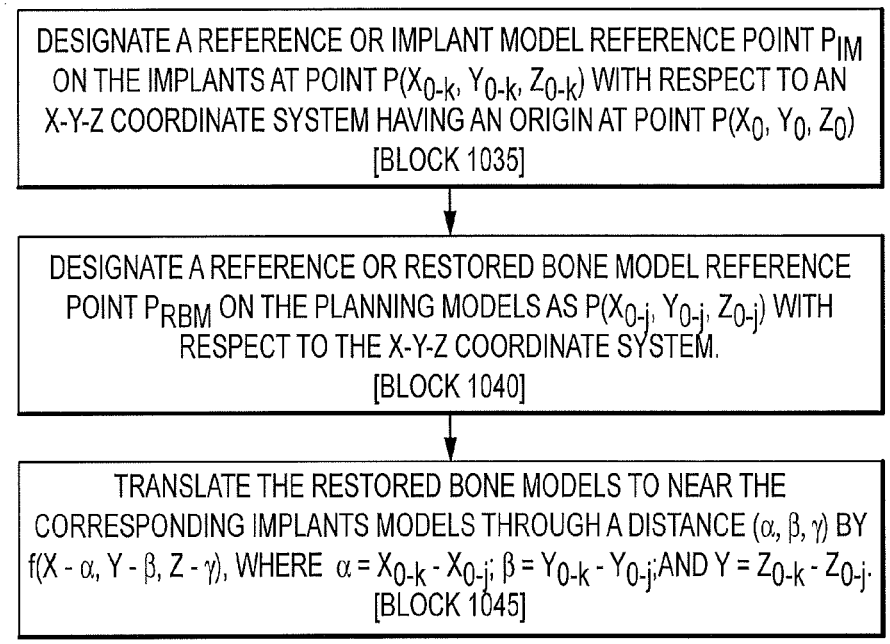
FIG. 4C is a flow chart depicting the process undertaken by the system when moving the femur and tibia restored bone models to be superimposed over the femur and tibia implant models.

In summary, as can be understood from FIGS. 4A-4B and FIG. 4C, which is a flow chart summarizing the process of superimposing the models 28, 34 over each other as mention in [block 174] of FIG. 1J, the implant reference point $P_{IM}$ is designated as coordinate point ($X_{0-k}$, $Y_{0-k}$, $Z_{0-k}$) with respect to an X-Y-Z coordinate system having an origin at coordinate point ($X_0$, $Y_0$, $Z_0$) [block 1035]. The implant reference point $P_{IM}$ may be located between the implants models 34', 34", close to their centers, near the intercondylar notch of the femur implant model 34'. The restored bone model reference point $P_{RBM}$ is designated as coordinate point ($X_{0-j}$, $Y_{0-j}$, $Z_{0-j}$) with respect to the X-Y-Z coordinate system having its origin at coordinate point ($X_0$, $Y_0$, $Z_0$) [block 1040]. The restored bone model reference point $P_{RBM}$ may be located between the restored bone models 28', 28", close to their centers, near the intercondylar notch of the femur restored bone model 28'.

In one embodiment, in the image analysis of the POP, the restored bone models 28', 28" may be translated to near the corresponding implants models 34', 34" through a distance ($\alpha$, $\beta$, $\gamma$) by f (x−$\alpha$, y−$\beta$, z−$\gamma$), where $\alpha = X_{0-k} - X_{0-j}$; $\beta = Y_{0-k} - Y_{0-j}$; and $\gamma = Z_{0-k} - Z_{0-j}$ [block 1045]. In other words, the restored bone models 28', 28" are moved to the implant models 34', 34" such that the two reference points $P_{RBM}$, $P_{IM}$ are generally in the same location. Therefore, the restored bone models 28', 28" and the implants models 34', 34" are closely superimposed to provide the starting reference points for translational and, rotational positioning of the femoral and tibial implants models 34', 34" with respect to the femur and tibia restored bone models 28', 28" for the shape matching process discussed in the following subsections of this Detailed Discussion. In other words, the above-described superimposing of the models 28, 34 may act as an initial rough positioning of the models in preparation for the following shape matching process.

F. Refining Positioning Between Bone and Implant Models

Once the bone and implant models 28, 34 are roughly positioned relative to each other via the above-described superimposing process, the positioning of the bone and implant models 28, 34 relative to each other is further refined prior to the shape matching process. The position refining process first entails the identification of landmark reference planes for the femur model, the utilization of the landmark reference planes to identify the elliptical contours of the femur restored bone model, and then the correlation of the femur elliptical contours to corresponding elliptical contours of the implant model in an approximate manner.

1. Determining Landmark Reference Planes for Femur Model.

The determination of the landmark reference planes for the femur model may be made via at least two methods. For example, a first method entails employing asymptotic lines to identify the landmark reference planes. In a second method, the landmark reference planes are identified via their relationship to a trochlear groove plane.

i. Landmark Reference Planes Identified Via Asymptotic Lines

Figure 5A:
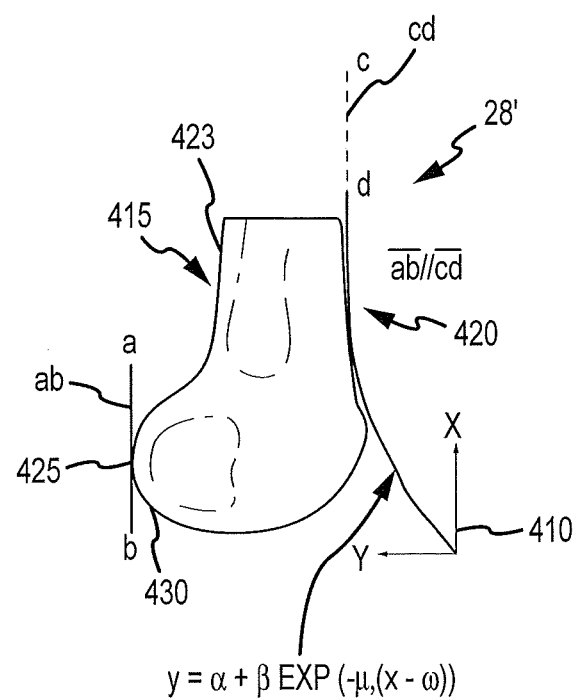
FIG. 5A is a view of the lateral side of the lower or distal portion of the femur restored bone model illustrating how to determine landmark reference lines for the posterior and anterior sides of the femur restored bone model.
Figure 5B:
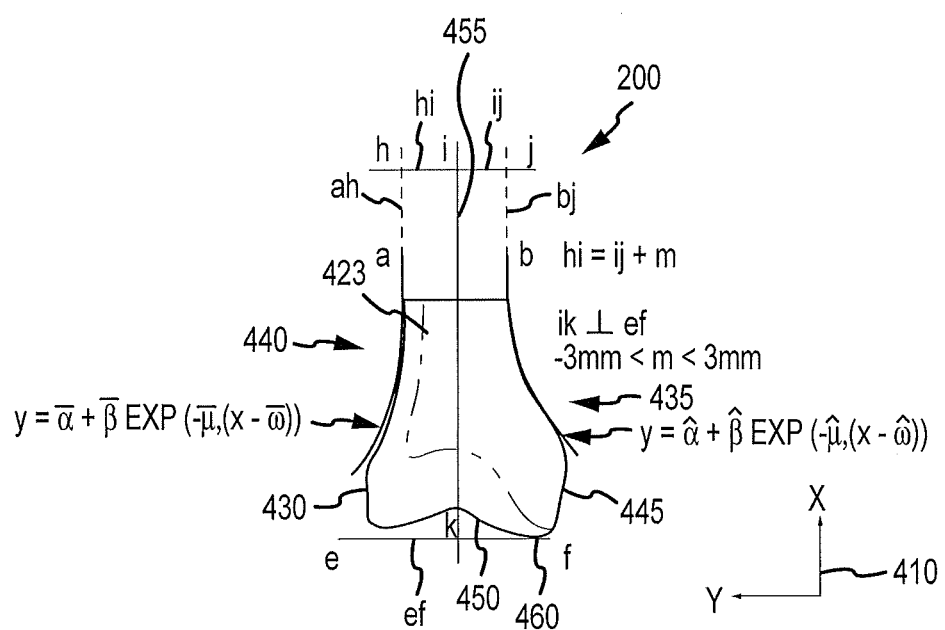
FIG. 5B is an anterior or coronal view of FIG. 5A illustrating how to determine landmark reference lines for the medial and lateral sides of the femur restored bone model.

FIGS. 5A-5C illustrate a process in the POP wherein the system 4 determines landmark reference planes via asymptotic lines for the femur restored bone model 28' (see FIG. 1J [block 175]) relative to a coordinate system axis 410. FIG. 5C is a flow chart illustrating the process for determining the landmark references. FIG. 5A is a view of the lateral side of the lower or distal portion of the femur restored bone model 28' illustrating how to determine landmark reference planes for the posterior and anterior sides 415, 420 of the femur planning model, which is also known as the femur restored bone model 28'. As indicated in FIGS. 5A and 5C, an asymptotic line-cd can be obtained by the exponential function, $y = \alpha + \beta \operatorname{EXP}(-\mu(x-\omega))$, from the anterior-distal femur along the anterior side 420 of the femoral shaft 423 [block 1050]. To obtain the tangent contact spot 425 representing the posterior extremity of lateral femoral condyle 430, the line-ab along the curvature of femoral condyle can be identified by using the asymptotic line-cd, where lines-cd, ab are parallel to each other, or where line-ab is substantially parallel to line-cd such that the acute angle between lines-cd, ab is less than approximately five degrees [block 1055]. In some embodiments, line-ab may represent a plane-ab that includes line-ab and is generally perpendicular to the sagittal image slice planes 16 used to form the restored bone model, as discussed with respect to FIGS. 1B-1C.

FIG. 5B is an anterior or coronal view of FIG. 5A illustrating how to determine landmark reference planes for the medial and lateral sides 435, 440 of the femur planning model 28'. As indicated in FIGS. 5B and 5C, the asymptotic line-ah can be obtained by the asymptotic distribution, $y = \overline{\alpha} + \overline{\beta} \operatorname{EXP}(-\overline{\mu}(x-\overline{\omega}))$, along the curvature of the lateral epicondyle 430 up to the lateral edge of femoral shaft 423 [block 1060]. Similarly, the asymptotic line-bj can be obtained by the asymptotic distribution, $y = \overline{\alpha} + \overline{\beta} \operatorname{EXP}(-\overline{\mu}(x-\overline{\omega}))$, along the curvature of the medial epicondyle 445 up to the medial edge of femoral shaft 423 [block 1065].

As indicated in FIG. 5B, the point-k represents the center of the distal femur shaft 423, the lowermost point in the patellofemoral surface 450. The point-i is located approximately at the midpoint between point-h and point-j. The lines-ik, ah are parallel, and line-ik defines the femoral anatomical axis (FAA) 455 [block 1070]. The lowest extremity of the medial epicondyle 445 is a tangent contact spot 460 that can be obtained in FIG. 5B by a line-ef extending across tangent contact spot 460, as line-ef is perpendicular to line-ik [block 1075]. In FIG. 5B, line-hi is related to line-ij by the equation: hi=ij+m, where −3 mm<m<3 mm [block 1080]. In some embodiments, line-ef may represent a plane-ef that includes line-ef and is generally perpendicular to the sagittal image slice planes 16 used to form the restored bone model, as discussed with respect to FIGS. 1B-1C.

ii. Landmark Reference Lines Identified Via Trochlear Groove Plane.

Figure 5D:
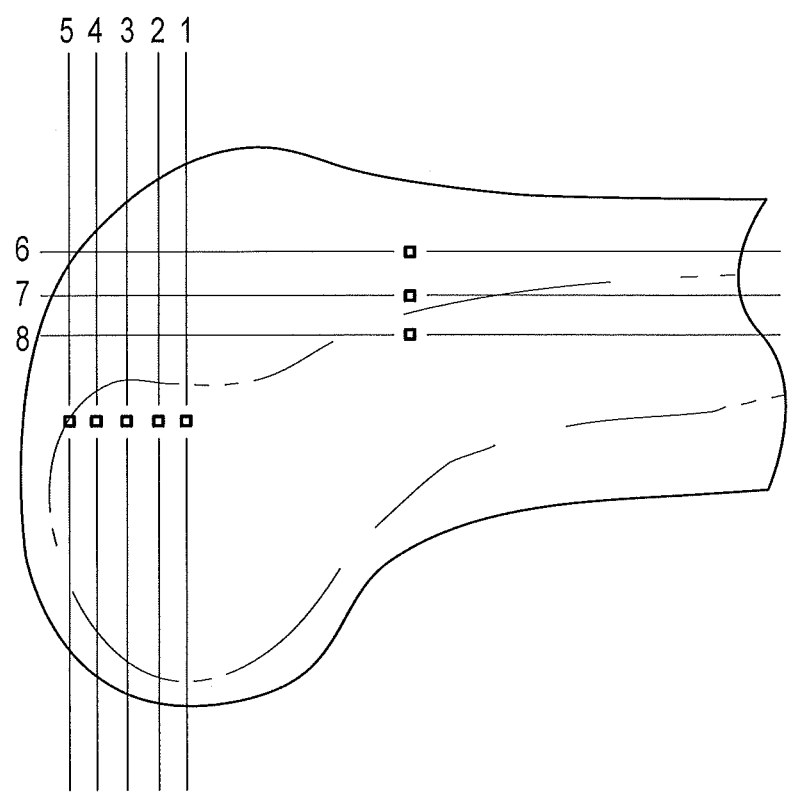
FIG. 5D is a sagittal view of a femur restored bone model illustrating the orders and orientations of imaging slices forming the femur restored bone model.
Figures 5E, 5F:
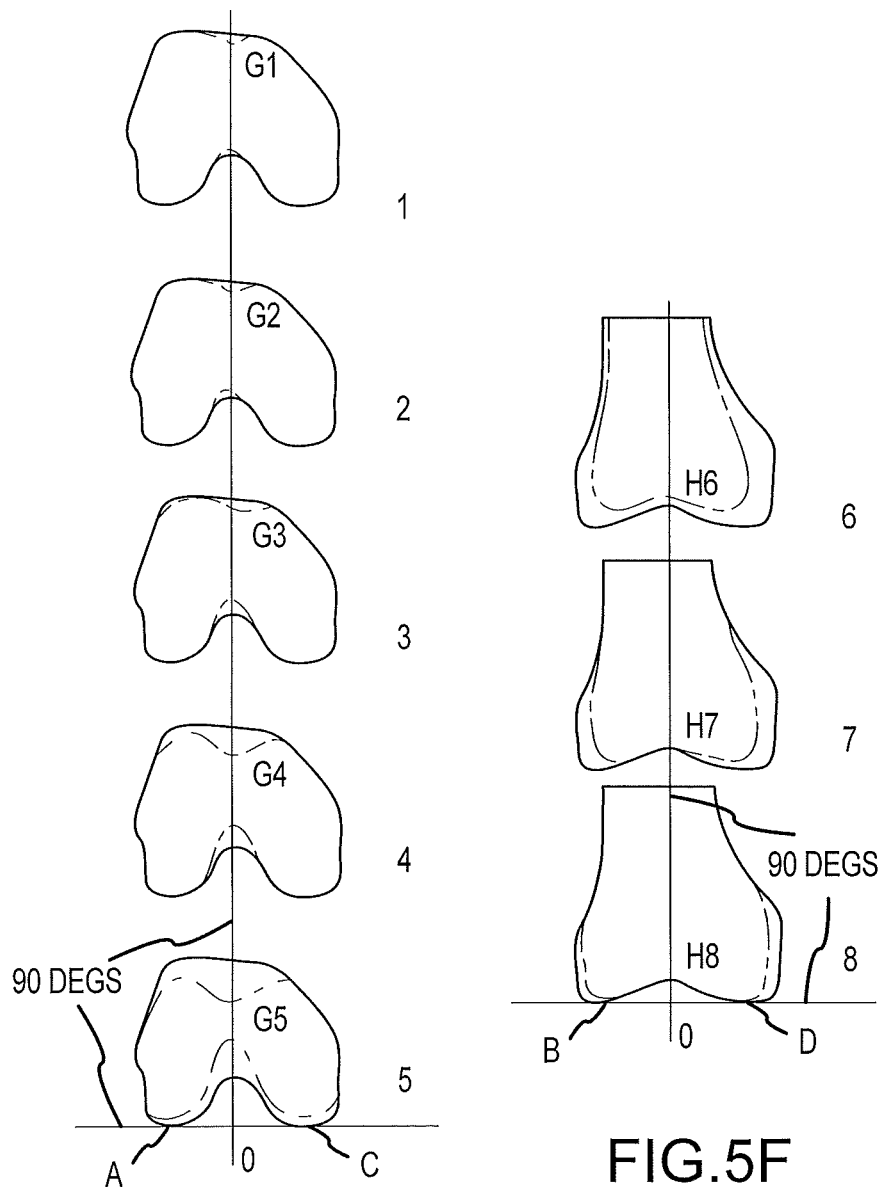
FIG. 5E is the distal images slices taken along section lines of the femur restored bone model in FIG. 5D.
FIG. 5F is the coronal images slices taken along section lines of the femur restored bone model in FIG. 5D.
Figure 5G:
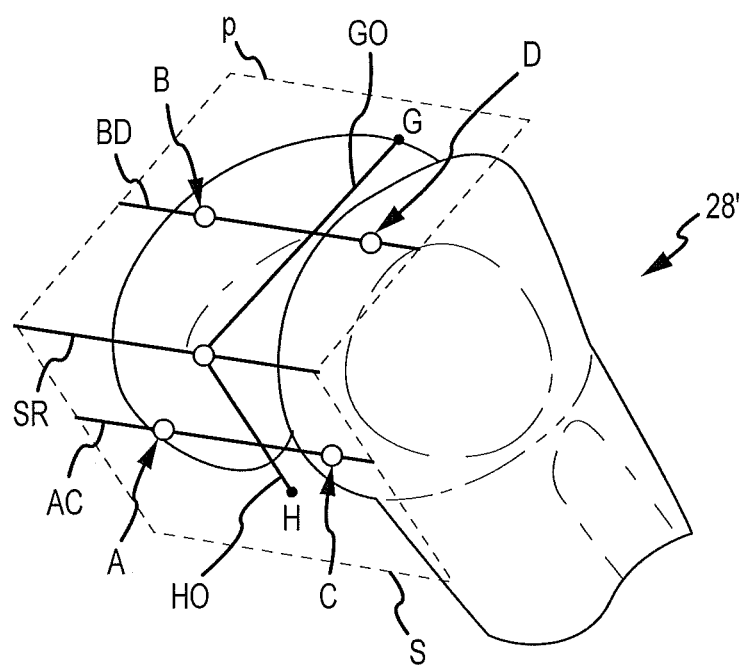
FIG. 5G is a perspective view of the distal end of the femur restored bone model.

FIGS. 5D-5G illustrate a process in the POP wherein the system 4 determines landmark reference planes via their relationship to the trochlear groove plane-GHO of the femur restored bone model 28' (see FIG. 1J [block 175]). FIG. 5D is a sagittal view of a femur restored bone model 28' illustrating the orders and orientations of imaging slices 16 (e.g., MRI slices, CT slices, etc.) forming the femur restored bone model 28'. FIG. 5E is the distal images slices 1-5 taken along section lines 1-5 of the femur restored bone model 28' in FIG. 5D. FIG. 5F is the coronal images slices 6-8 taken along section lines 6-8 of the femur restored bone model 28' in FIG. 5D. FIG. 5G is a perspective view of the distal end of the femur restored bone model 28'.

In one embodiment, the identification of the trochlear groove plane-GHO may be made during the verification of the accuracy of the bone restoration process as disclosed in U.S. patent application Ser. No. 12/111,924 to Park, which is entitled Generation of a Computerized Bone Model Representative of a Pre-Degenerated State and Usable in the Design and Manufacture of Arthroplasty Devices, was filed Apr. 29, 2008 and is incorporated by reference in its entirety into this Detailed Description.

As shown in FIG. 5D, a multitude of image slices are compiled into the femur restored bone model 28' from the image slices originally forming the femur bone model 22' (see FIG. 1C [block 110]) and those restored image slices as modified via the methods disclosed in U.S. patent application Ser. No. 12/111,924. Image slices may extend medial-lateral in planes that would be normal to the longitudinal axis of the femur, such as image slices 1-5. Image slices may extend medial-lateral in planes that would be parallel to the longitudinal axis of the femur, such as image slices 6-8. The number of image slices may vary from 1-50 and may be spaced apart in a 2 mm spacing.

As shown in FIG. 5E, each of the slices 1-5 can be aligned vertically along the trochlear groove, wherein points-G1, G2, G3, G4, G5 respectively represent the lowest extremity of trochlear groove for each slice 1-5. By connecting the various points G1, G2, G3, G4, G5, a point-O can be obtained. As can be understood from FIG. 5G, resulting line-G0, is perpendicular or nearly perpendicular to tangent line-AC. In a 90° knee extension, line-GO is perpendicular or nearly perpendicular to the joint line of the knee and line-AC. As can be understood from FIGS. 6A and 6B, points-A and C represent the most posterior contact points on the femoral condylar surfaces.

As shown in FIG. 5F, each of the slices 6-8 can be aligned vertically along the trochlear groove, wherein points-H6, H7, H8 respectively represent the lowest extremity of the trochlear groove for each slice 6-8. By connecting the various points-H6, H7, H8, the point-O can again be obtained. As can be understood from 5G, resulting line HO is perpendicular or nearly perpendicular to tangent line-BD. In a 0° knee extension, line HO is perpendicular or nearly perpendicular to the joint line of the knee and line BD. As can be understood from FIGS. 6A and 6B, points-B and D represent the most distal contact points on the femoral condylar surfaces.

As illustrated in FIG. 5G, the trochlear grove plane-GHO, as the reference across the most distal extremity of the trochlear groove of the femur and in a 90° knee extension, should be perpendicular to tangent line AC. The line-HO, as the reference across the most posterior extremity of trochlear groove of the femur and in a 0° knee extension, should be perpendicular to tangent line AC.

Line HO and line AC may form a plane S, and lines GO and line BD may form a plane P that is perpendicular to plane S and forms line SR therewith. Line HO and line G0 are parallel or nearly parallel to each other. Lines AC, BD and SR are parallel or nearly parallel to each other. Lines AC, BD and SR are perpendicular or nearly perpendicular to lines HO and G0 and the trochlear plane GHO.

2. Determine Elliptical Contours for Condyles of Femur Restored Bone Model.

Figures 6A, 6B:
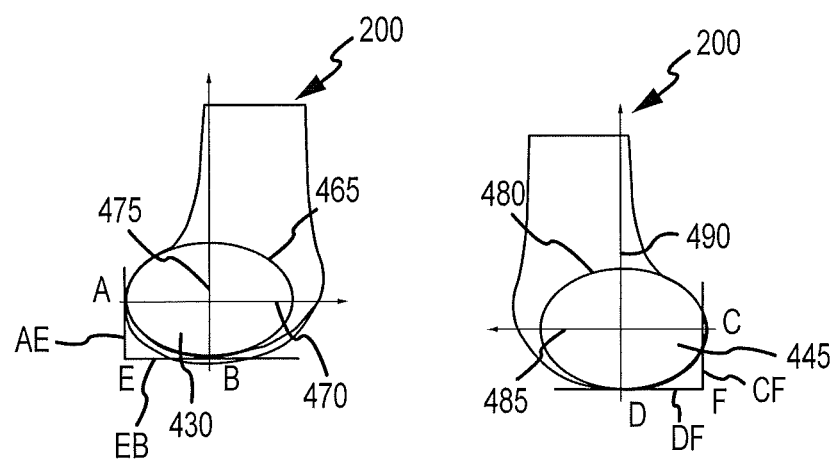
FIGS. 6A and 6B are respective sagittal views of the lateral and medial condyles of the femur restored bone model depicted in FIG. 5B, wherein elliptical contours of the condyles have been determined from the landmark reference lines depicted in FIG. 5B.

FIGS. 6A and 6B are respective sagittal views of the lateral and medial condyles 430, 445 of the distal femur restored bone model 28' depicted in FIGS. 5B and 5G, wherein elliptical contours of the condyles 430, 445 have been determined from the landmark reference lines depicted in FIG. 5B or FIG. 5G (see FIG. 1J [block 176]). FIG. 6C is a flow chart illustrating the process of determining the elliptical contours of the condyles 430, 445 from the landmark reference lines depicted in FIG. 5B or FIG. 5G.

Based on plane-ef from FIG. 5B and plane-ab from FIG. 5A, or, alternatively, from plane-p from FIG. 5G and plane-s from FIG. 5G, the related reference landmarks can be obtained on the sagittal views of lateral condyle 430 and medial condyle 445 in FIGS. 6A and 6B. As can be understood from a comparison of FIGS. 5A and 5G to FIGS. 6A and 6B, reference lines or planes-AE, CF are parallel to plane-ab and plane-s and respectively intersect the posterior extremity of the lateral femoral condyle 430 and the medial femoral condyle 445 at respective tangent spots A, C [block 1085]. As can be understood from a comparison of FIGS. 5B and 5G to FIGS. 6A and 6B, reference planes-EB, DF are parallel to plane-ef and plane-p and respectively intersect the distal or bottom most extremity of the lateral femoral condyle 430 and the medial femoral condyle 445 at respective tangent spots B, D [block 1090]. In one embodiment, in addition to being employed to identify the most distal extremities B, D and most posterior extremities A, C of the elliptical shape of the condyles, the planes-EB, DF, AE, CF may be used to define the major elliptical axes 470, 485 and minor elliptical axes 475, 490 of the elliptical shape of the condyle surfaces. These axes and points may be corresponded to similar axes and points of the implant models 34', as described below.

As indicated in FIG. 6A, plane-AE represents the tangent of the lateral condylar curve at the most proximal point-A, and plane-EB represents the tangent of the lateral condylar curve at the most distal point-B. The respective tangent contact spots A, B of the planes-AE, EB define the major axis 470 and minor axis 475 of the lateral ellipse contour 465 [block 1095].

As indicated in FIG. 6B, plane-CF represents the tangent of the medial condylar curve at the most proximal point-C, and plane-DF represents the tangent of the medial condylar curve at the most distal point-D. The respective tangent contact spots C, D of the planes-CF, DF define the major axis 485 and minor axis 490 of the medial ellipse contour 480 [block 1100].

3. Determine Elliptical Contours for Condyles of Femur Implant and Align in an Approximate Manner Implant Condyles to Femur Model Condyles.

Figure 7A:
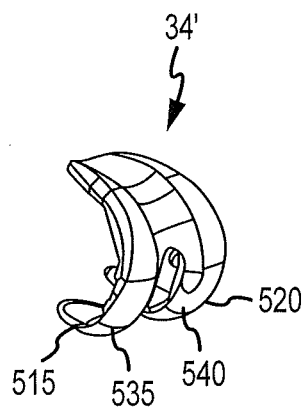
FIG. 7A shows an isometric bottom view of the conventional femoral implant model depicted in FIG. 2B.

FIG. 7A shows an isometric bottom view of the conventional femoral implant model 34' depicted in FIG. 2B. As can be understood from the following discussion, the elliptical contours 505, 510 for the lateral and medial condyles 515, 520 of the femur implant model 34' are determined (see FIG. 1K [block 177]). The lateral and medial condyles 515, 520 of the femur implant model 34' are then aligned in an approximate or rough manner with the lateral and medial condyles 430, 445 of the femur restored bone model 28' (see FIG. 1K [block 178]).

Figure 7B:
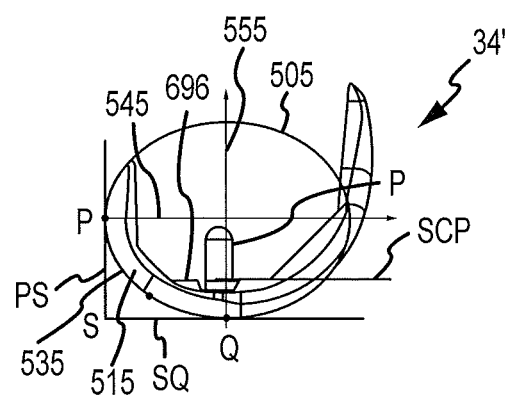
FIGS. 7B and 7C are, respectively, side views of the lateral and medial sides of the femur implant model depicted in FIG. 7A.
Figure 7C:
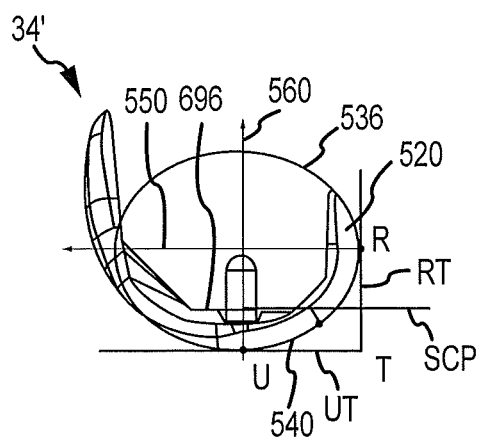

FIGS. 7B and 7C are, respectively, side views of the lateral and medial sides 525, 530 of the femur implant model 34' depicted in FIG. 7A. FIG. 7D is a flow chart illustrating the method of determining elliptical contours 505, 510 and approximately or roughly aligning the respective condyles 430, 445, 515, 520 of the restored bone model 28' with the implant model 34'.

As indicated in FIG. 7B, the lateral femur implant condyle 515 includes an elliptical contour 505 corresponding with the outer condyle surface 535. Plane-PS is tangential to the most posterior point P on the lateral outer condyle surface 535, and plane-SQ is tangential to the most distal or bottom point Q on the lateral outer condyle surface 535 [block 1105]. Planes-PS, SQ, which may also be considered vectors or lines, intersect each other at point-S and are perpendicular to each other.

As indicated in FIG. 7C, the medial femur implant condyle 520 includes an elliptical contour 510 corresponding with the outer condyle surface 540. Plane-RT is tangential to the most posterior point R on the medial outer condyle surface 540, and plane-UT is tangential to the most distal or bottom point U on the medial outer condyle surface 540 [block 1110]. Planes-RT, UT, which may also be considered lines or vectors, intersect each other at point T and are perpendicular to each other.

As indicated in FIGS. 7B and 7C, points-P, R define the major axes 545, 550 of the respective elliptical contours 505, 510 and minor axes 555, 560 of the respective elliptical contours 505, 510 [block 1115]. Thus, planes-PS, SQ identify respectively the most posterior and distal points on the lateral outer surface 535, and planes-RT, UT identify respectively the most posterior and distal points on the medial outer surface 540. Because the major and minor axes and the most distal and posterior points on the elliptical contour of the condylar surfaces can be determined, the elliptical shape of the condylar surfaces can be measured and obtained.

In case of a femoral implant model 34' with symmetric condyles 515, 520, both ellipse 505, 510 on the medial side 520 and lateral side 515 are the same where plane-PS equals plane-RT and plane-SQ equals plane-UT. By the application of these planes-PS, RT, SQ, UT of the femoral implant model 34', the femoral model condyles 430, 445 can be aligned to the proximity of the corresponding femoral implant condyles 515, 520 where plane-AE is parallel to plane-PS, plane-EB is parallel to plane-SQ, plane-CF is parallel to plane-RT, and plane-DF is parallel to plane-UT [block 1120].

In one embodiment, where the trochlear groove plane is determined with respect to the restored bone model 28', as discussed above with respect to FIGS. 5D-5G, a similar process may be employed to find the trochlear groove plane for the femoral implant model 34'. Thus, each of the bone model planes-EB and DF will be perpendicular to the bone model trochlear groove plane, and each of the implant model planes-SQ and UT will be perpendicular to the implant model trochlear groove plane. In such an embodiment, plane-AE is parallel to plane-PS, plane-EB is parallel to plane-SQ, plane-CF is parallel to plane-RT, and plane-DF is parallel to plane-UT.

The relationships between the planes-AE, EB, CF and DF of the restored bone model 28' can be positionally correlated with the respective corresponding planes-PS, SQ, RT and UT of the femur implant model 34' to refine the initial superimposing of the femur restored bone model 28' over the implant model 34' such that the condylar surfaces 465, 480 of the bone model 28' are approximately aligned with the respective condylar surfaces 535, 540 of the implant model 34' prior to the shape matching process described below in this Detailed Description.

G. Shape Matching Condylar Surfaces of Restored Bone Model to Condylar Surfaces Of Femoral Implant Model.

In one embodiment, the POP system and method, once the position of the bone model and implant model is refined as described immediately above, then employs a shape match technique to match a model 34' of an available femoral implant to the femoral planning or restored bone model 28'. Before employing the shape match technique, it is determined if an asymmetrically modified femoral implant is selected for the POP process, or is a symmetric femoral implant is selected for the POP process (see FIG. 1K [block 179]).

1. Asymmetrically Modified Femoral Implant Model

For a discussion regarding a POP design employing an asymmetrically modified femoral implant model 34', reference is made to FIGS. 8A-10. FIG. 8B shows a coronal view of a distal femur restored bone model 28' having symmetrical femoral condyles 430', 445'. The FAA 455' extends through the center of the femur restored bone model 28'. A rotation reference line 600' connects the lowest extremities of the two femoral condyles 430', 445'.

Figures 8A, 8B:
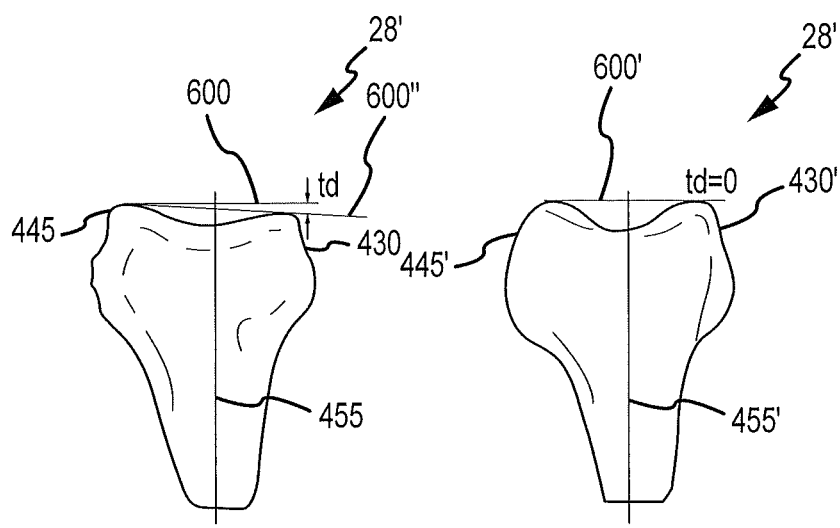
FIG. 8A shows a coronal view of a distal femur restored bone model having an asymmetrical relationship between its condyles.
FIG. 8B shows a coronal view of a distal femur restored model having symmetrical femoral condyles.

FIG. 8B depicts a joint where the size of lateral condyle 430' is substantially equal to the size of medial condyle 445'. In this situation, the FAA 455' is perpendicular or substantially perpendicular to the reference line 600', where the offset distance td' between the reference line 600' and the lateral condyle 430' is zero (i.e., td'=0) or nearly so. The offset distance td' is the difference between the medial condyle 445' and the lateral condyle 430' of distal femur restored bone model 28'.

FIG. 8A shows a coronal view of a distal femur restored bone model 28' having an asymmetrical relationship between its condyles 430, 445. The asymmetrical relationship can be the result of the femur naturally having one condyle larger than the other condyle, and depending on which condyle is larger, the knee will be varus or valgus. For example, it is common for the medial condyle 445 to be larger than the lateral condyle 430. As a result, the alignment of the rotation reference line 600" relative to the FAA 455 tilts from the medial condyle 445 towards the lateral condyle 430, when the rotation reference line 600" is not held perpendicular to the FAA 455. Where the rotation reference line 600 is held perpendicular to the FAA 455, an offset distance td is indicated, wherein the offset distance is the difference between the sizes of the medial and lateral condyles 445, 430.

As shown in FIG. 8A, with respect to FAA 455, the lateral condyle 430 is smaller than the medial condyle 445, leaving an offset distance td when reference line 600 is maintained perpendicular to the FAA 455, as opposed to tilting against the surfaces of both condyles 430, 445, as depicted by reference line 600". The offset distance td is the difference between the medial condyle 445 and lateral condyle 430 of the distal femur model 28'. Depending on the direction of the tilt and which condyle 430, 445 is smaller, the result is a varus deformity or a valgus deformity. The femoral condyle or offset difference td in FIG. 8A varies depending on the amount natural difference between the medial and lateral condyles 445, 430.

Figures 9A, 9B:
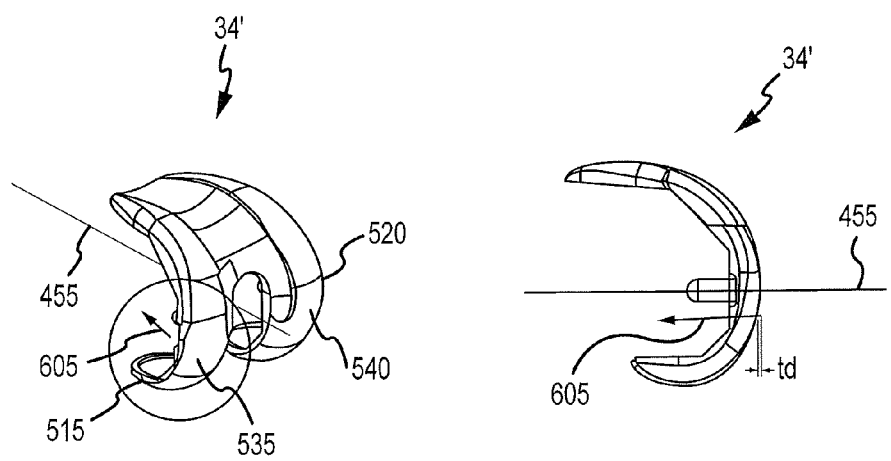
FIGS. 9A and 9B are, respectively, an isometric view of a symmetric femur implant model and a lateral side view of the femur implant model after being asymmetrically modified.
Figure 9C:
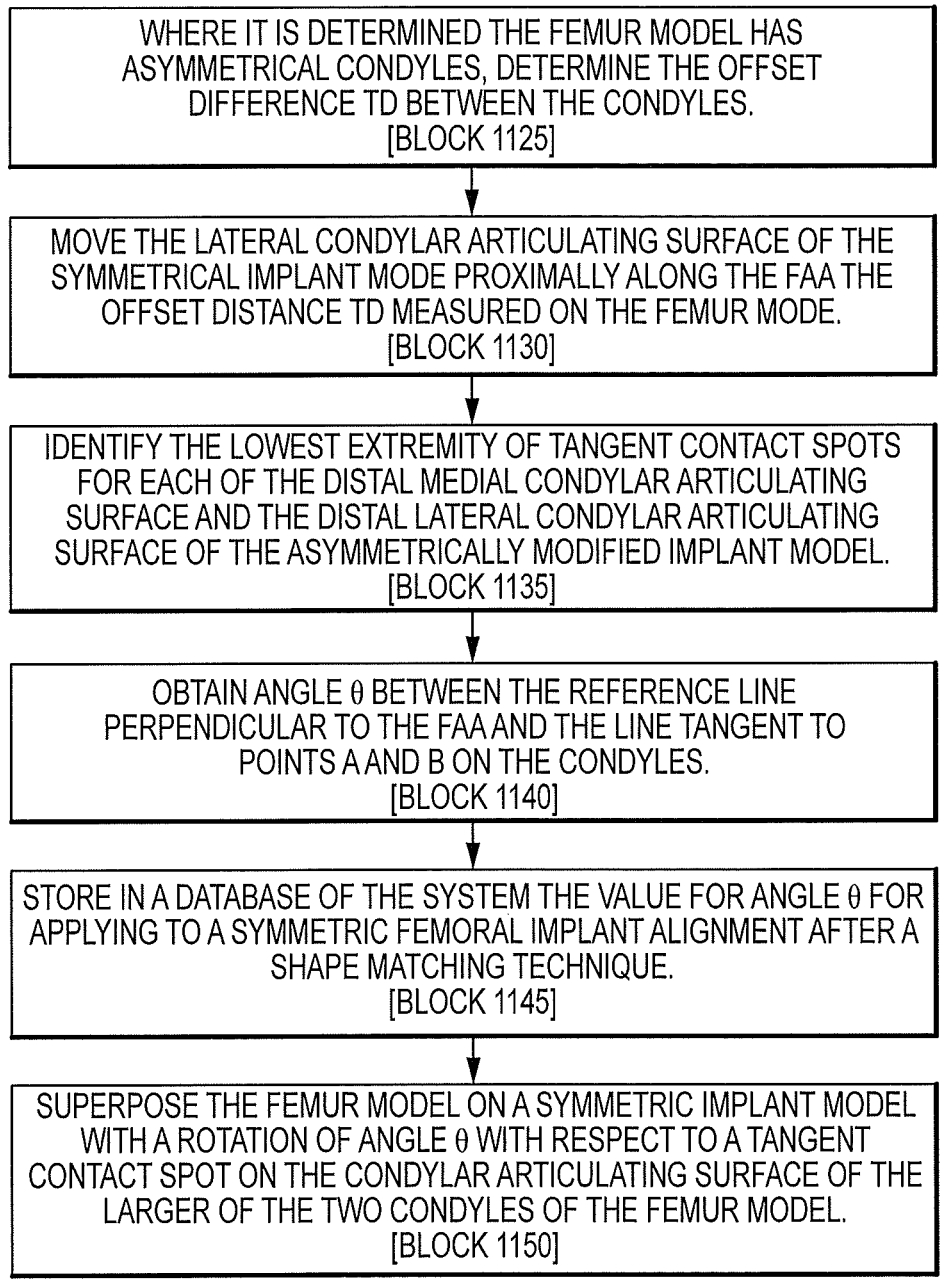
FIG. 9C is a flow chart depicting the method of shape fitting with an asymmetrically modified femur implant model.

As can be understood from FIG. 8A and FIG. 9C, which is a flow chart depicting the method of shape fitting with an asymmetrically modified implant model 34', where the system 4 determines the femur model 28' has asymmetrical condyles 430, 445, the system 4 will determine the offset difference td between the condyles 430, 445 [block 1125].

FIGS. 9A and 9B are, respectively, an isometric view of a symmetric implant model 34' and a lateral side view of the implant model 34' after being asymmetrically modified. As indicated in FIG. 9A, prior to being asymmetrically modified, the symmetric implant model 34' has symmetrical lateral and medial condyles 515, 520 with articulating surfaces 535, 540 that are nearly the same size. In order to modify the symmetric implant model 34' to fit the asymmetrical nature of bone model 28', the lateral condylar articulating surface 535 of the symmetrical implant model 34' is moved proximally, as indicated by arrow 605, along the FAA 455 the offset distance td measured on the femur model 34' in FIG. 8A [block 1130].

Figure 10:
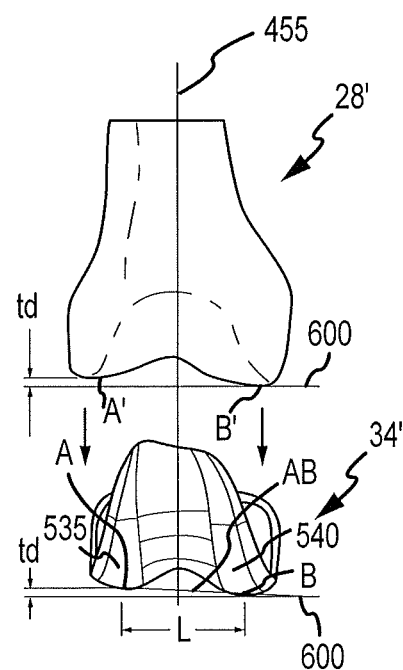
FIG. 10 is a coronal view of the femur restored bone model and the asymmetrical implant model aligned along the FAA, which serves as the reference axis for rotational and translation alignment between the femur and implant models.

FIG. 10 is a coronal view of the femur model 28' and the asymmetrical implant model 34' aligned along the FAA 455, which serves as the reference axis for rotational and translation alignment between the femur and implant models 28', 34'. As shown in FIG. 10, due to the asymmetric condyle configuration depicted in FIG. 8A, the femoral condyle difference td in FIGS. 8A and 9B is shown in each of the femur model 28' and the correspondingly asymmetrically modified implant model 34'. The lowest extremity of tangent contact spots A' and B' are know from the tangent plane procedures described above in this Detailed Description. Also, the information pertaining to FAA and td are known from the above described procedures.

As can be understood from FIG. 10, the lowest extremity of tangent contact spots A and B for the implant model 34' can be identified in each of the distal medial condylar articulating surface 540 and the distal lateral condylar articulating surface 535, respectively [block 1135]. The FAA and td for the implant model 34' are determined from the bone model 28', and the lowest extremities A and B of the implant model condylar surfaces may be measured.

Because the line-AB connecting point-A and point-B is titled relative to the reference line 600, an angle θ can be obtained where $\theta=\tan^{-1}(td/L)$ and L is the distance along the reference line 600 between points A and B [block 1140]. The value for angle θ can be stored in a database 15 of the system 4 and further applied to a symmetric femoral implant alignment after the shape matching technique described below with respect to FIGS. 16-19 in this Detailed Description [block 1145]. After the shape matching technique, in order to achieve accurate alignment and rotation between the femur model 28' and a symmetric implant model 34' representative of an actual implant provided by an implant manufacturer, the femur model 28' of FIG. 10 will be superposed to the symmetric implant model 34' with a rotation of angle θ with respect to point B in FIG. 10 [block 1150].

2. Symmetrical Femoral Implant

Figure 11A:
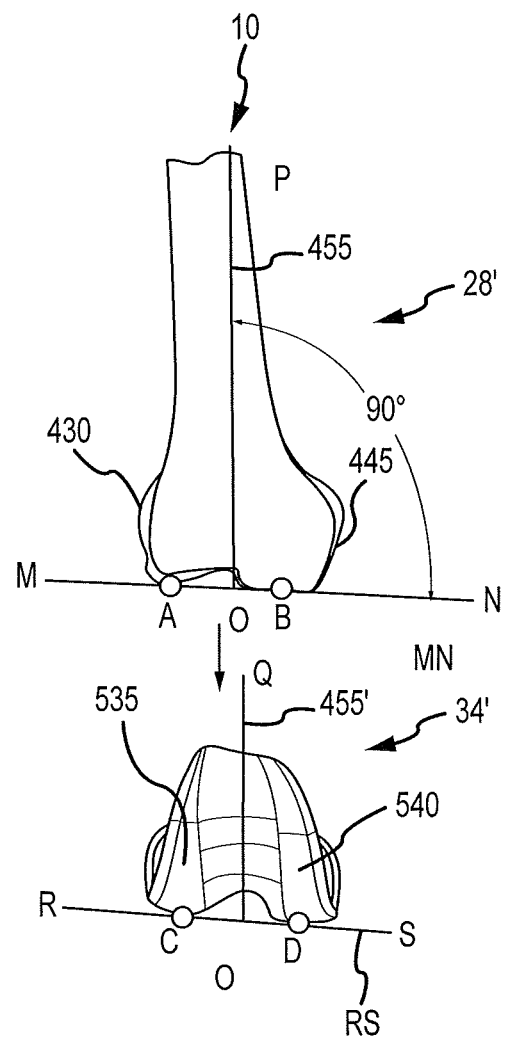
FIG. 11A is a coronal view of the asymmetrical femur restored bone model and the symmetrical implant model.
Figure 11B:
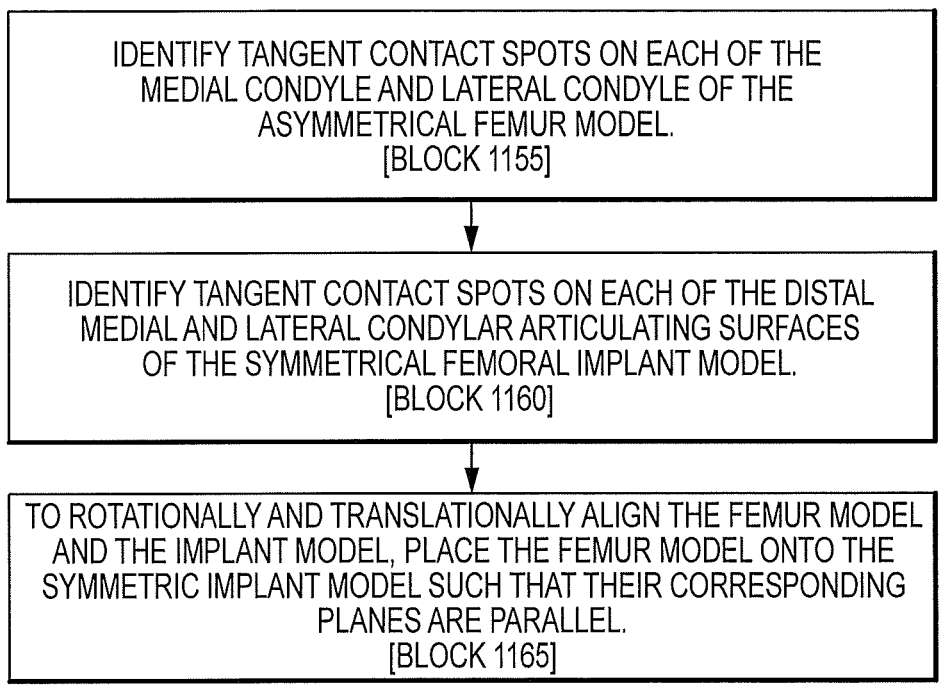
FIG. 11B is a flow chart illustrating the method of shape fitting with the symmetrical implant model.

For a discussion regarding a POP design employing an symmetrical femoral implant model 34', reference is made to FIGS. 11A and 11B. FIG. 11A is a coronal view of the asymmetrical femur model 28' and the symmetrical implant model 34'. FIG. 11B is a flow chart illustrating the method of shape fitting with the symmetrical implant model 34'.

As indicated in FIGS. 11A and 11B, the lowest extremity of tangent contact spots B and A are identified on each of the medial condyle 445 and lateral condyle 430, respectively [block 1155]. The line-MN extends across the two lowest extremity points-A, B and is presumed to be parallel to the joint line of the knee in a knee kinetics study. In one embodiment, the line 455 may represent the trochlear groove axis (plane, line or vector direction OP) reference. The line-MN may be perpendicular or generally perpendicular to the trochlear groove axis-455. Similarly, in the symmetrical femoral implant model 34', the lowest extremity of tangent contact spots D and C can be identified in each of the distal medial condylar articulating surface 540 and the distal lateral condylar articulating surface 535, respectively [block 1160]. With reference to the trochlear groove axis 455 (i.e., plane, line or vector direction OQ), the line across points-C, D and perpendicular to reference line 455 is defined as line or plane RS. To rotationally and translationally align the femur model 28' and the symmetric implant model 34', place the femur model 28' onto the symmetric implant model 34' such that plane MN is parallel to plane RS and plane OP is parallel to plane OQ [block 1165].

3. Determining Joint Line and Adjustment to Surface Matching that Allows Surface Matching of Implant Model Condylar Surfaces to Restored Bone Model Condylar Surfaces to Restore Joint to Natural Configuration.

In order to allow an actual physical arthroplasty implant to restore the patient's knee to the knee's pre-degenerated or natural configuration with the its natural alignment and natural tensioning in the ligaments, the condylar surfaces of the actual physical implant generally replicate the condylar surfaces of the pre-degenerated joint bone. In one embodiment of the systems and methods disclosed herein, condylar surfaces of the restored bone model 28' are surface matched to the condylar surfaces of the implant model 34'. However, because the restored bone model 28' may be bone only and not reflect the presence of the cartilage that actually extends over the pre-degenerated condylar surfaces, the surface matching of the modeled condylar surfaces may be adjusted to account for cartilage or proper spacing between the condylar surfaces of the cooperating actual physical implants (e.g., an actual physical femoral implant and an actual physical tibia implant) used to restore the joint such that the actual physical condylar surfaces of the actual physical cooperating implants will generally contact and interact in a manner substantially similar to the way the cartilage covered condylar surfaces of the pre-degenerated femur and tibia contacted and interacted.

Thus, in one embodiment, the implant model is modified or positionally adjusted to achieve the proper spacing between the femur and tibia implants. To achieve the correct adjustment, an adjustment value tr may be determined (see FIG. 1K [block 180]). In one embodiment, the adjustment value tr that is used to adjust the surface matching may be based off of an analysis associated with cartilage thickness. In another embodiment, the adjustment value tr used to adjust the surface matching may be based off of an analysis of proper joint gap spacing. Both of the methods are discussed below in turn.

i. Determining Cartilage Thickness and Joint Line

Figure 12:
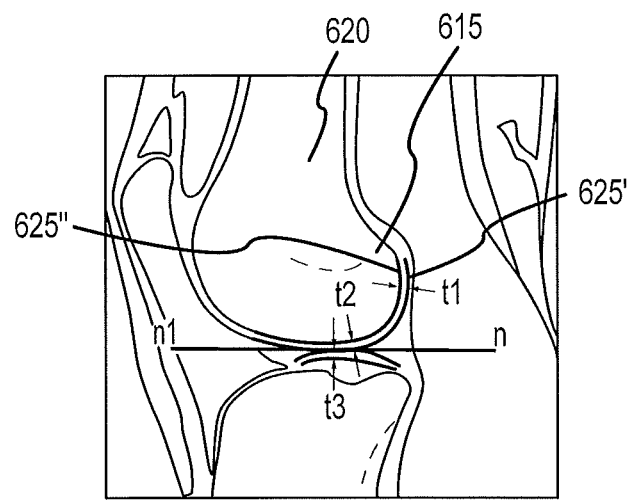
FIG. 12 shows the sagittal view MRI slice of the femoral condyle and the proximal tibia of the knee in a MRI image slice.

FIG. 12 shows the sagittal view MRI slice of the femoral condyle 615 and the proximal tibia of the knee in a MRI image slice. The distal femur 620 is surrounded by the thin black rim of cortical bone. Due to the nature of irregular bone and cartilage loss in OA patients, it can be difficult to find the proper joint line reference for the models used during the POP.

The space between the elliptical outlining 625', 625" along the cortical bone represents the cartilage thickness of the femoral condyle 615. The ellipse contour of the femoral condyle 615 can be seen on the MRI slice shown in FIG. 12 and obtained by a three-point tangent contact spot (i.e., point t1, t2, t3) method. This three-point contact spot method is illustrated with respect to FIGS. 14A-14D, and its purpose is to "restore" the joint line reference. In a normal, healthy knee, the bone joint surface is surrounded by a layer of cartilage. Because the cartilage is generally worn-out in OA and the level of cartilage loss varies from patient to patient, it may be difficult to accurately account for the cartilage loss in OA patients when trying to restore the joint via TKA surgery. Therefore, in one embodiment of the methodology and system disclosed herein, a minimum thickness of cartilage is obtained based on medical imaging scans (e.g., MRI, etc.) of the undamaged condyle. Based on the cartilage information, the joint line reference can be restored. For example, the joint line MN identified above may be line 630 in FIG. 13.

The system and method disclosed herein provides a POP method to substantially restore the joint line back to a "normal or natural knee" status (i.e., the joint line of the knee before OA occurred) and preserves ligaments in TKA surgery (e.g., for a total knee arthroplasty implant) or partial knee arthroplasty surgery (e.g., for a uni-knee implant).

Figure 13:
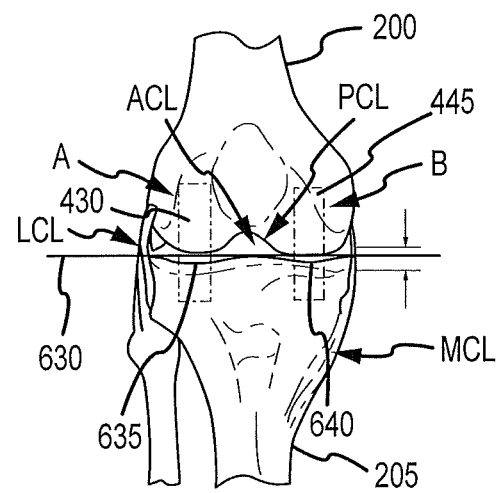
FIG. 13 is a coronal view of a knee model in extension.

FIG. 13 is a coronal view of a knee model in extension. As depicted in FIG. 13, there are essentially four separate ligaments that stabilize the knee joint, which are the medial collateral ligament (MCL), anterior cruciate ligament (ACL), lateral collateral ligament (LCL), and posterior cruciate ligament (PCL). The MCL and LCL lie on the sides of the joint lie and serve as stabilizers for the side-to-side stability of the knee joint. The MCL is a broader ligament, whereas the LCL is a distinct cord-like structure.

The ACL is located in the front part of the center of the joint. The ACL is a very important stabilizer of the femur on the tibia and serves to prevent the tibia from rotating and sliding forward during agility, jumping, and deceleration activities. The PCL is located directly behind the ACL and the tibia from sliding to the rear. The system and method disclosed herein provides POP that allows the preservation of the existing ligaments without ligament release during TKA surgery. Also, the POP method provides ligament balance, simplifying TKA surgery procedures and reducing pain and trauma for OA patients.

As indicated in FIG. 13, the joint line reference 630 is defined between the two femoral condyles 430, 445 and their corresponding tibia plateau regions 635, 640. Area A illustrates a portion of the lateral femoral condyle 430 and a portion of the corresponding lateral plateau 635 of tibia 205. Area 13 illustrates the area of interest showing a portion of the medial femoral condyle 445 and a portion of the corresponding medial plateau 640 of tibia 205.

Figure 14A:
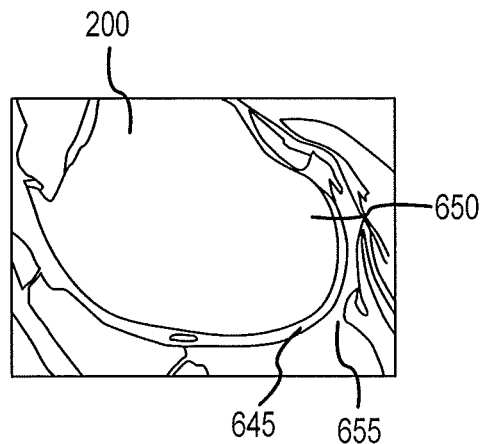
FIGS. 14A and 14B illustrate MRI segmentation slices for joint line assessment.
Figure 14B:
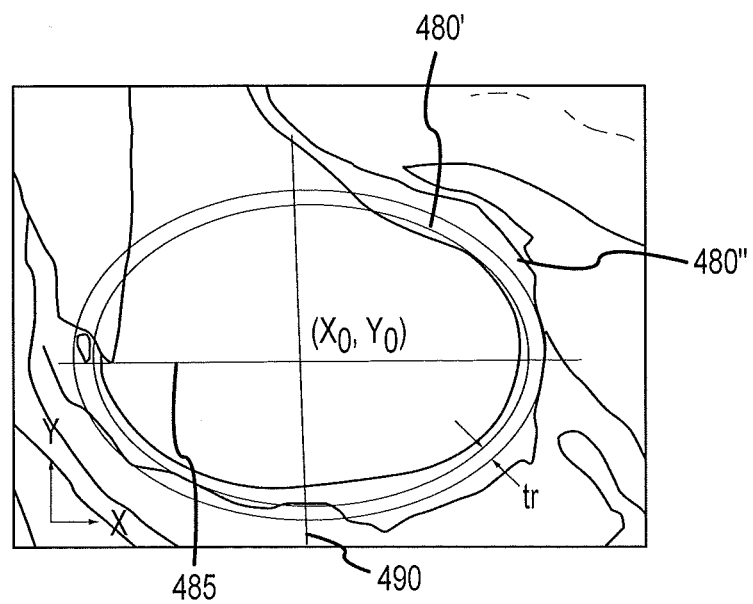
Figure 14D:
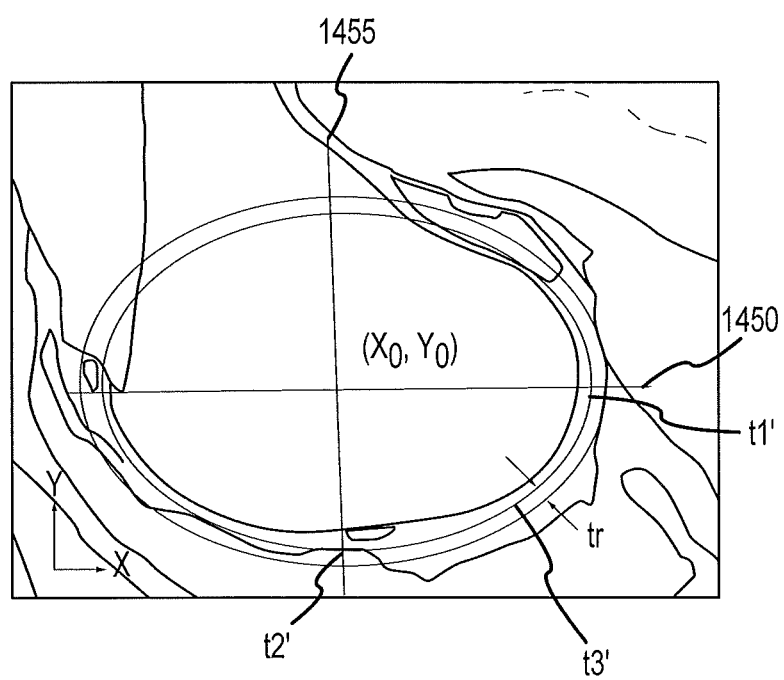
FIG. 14D illustrates a MRI segmentation slice for joint line assessment.

FIGS. 14A, 14B and 14D illustrate MRI segmentation slices for joint line assessment. FIG. 14C is a flow chart illustrating the method for determining cartilage thickness used to determine proper joint line. The distal femur 200 is surrounded by the thin blank rim of cortical bone 645. The cancellous bone (also called trabecular bone) 650 is an inner spongy structure. An area of cartilage loss 655 can be seen at the posterior distal femur. For OA patients, the degenerative cartilage process typically leads to an asymmetric wear pattern that results one femoral condyle with significantly less articulating cartilage than the other femoral condyle. This occurs when one femoral condyle is overloaded as compared to the other femoral condyle.

As can be understood from FIGS. 14A and 14C, the minimum cartilage thickness is observed and measured for the undamaged and damaged femoral condyle 430, 445 [block 1170]. If the greatest cartilage loss is identified on the surface of medial condyle 445, for example, then the lateral condyle 430 can be used as the cartilage thickness reference for purposes of POP. Similarly, if the greatest cartilage loss is identified on the lateral condyle 430, then the medial condyle 445 can be used as the cartilage thickness reference for purposes of POP. In other words, use the cartilage thickness measured for the least damaged condyle cartilage as the cartilage thickness reference for POP [block 1175]

As indicated in FIG. 14B, the thickness of cartilage can be analyzed in order to restore the damaged knee compartment back to its pre-OA status. In each of the MRI slices taken in regions A and 13 in FIG. 13, the reference lines as well as the major and minor axes 485, 490 of ellipse contours 480', 480" in one femoral condyle 445 can be obtained.

As shown in FIG. 14D, for the three-point method, the tangents are drawn on the condylar curve at zero degrees and 90 degrees articular contact points. The corresponding tangent contact spots t1' and t2' are obtained from the tangents. The line 1450 perpendicular to the line 1455 determines the center of the ellipse curve, giving the origin of (0, 0). A third tangent contact spot t3' can be obtained at any point along the ellipse contour between the 90 degree, t1 point and the zero degree, t2' point. This third spot t3' can be defined as k, where k=1 to n points.

The three-point tangent contact spot analysis may be employed to configure the size and radius of the condyle 445 of the femur restored bone model 28'. This provides the "x" coordinate and "y" coordinate, as the (x, y) origin (0, 0) shown in FIG. 14B. The inner ellipse model 480' of femoral condyle shows the femoral condyle surrounded by cortical bone without the cartilage attached. The minimum cartilage thickness $tm_{min}$ outside the inner ellipse contour 480' is measured. Based on the analysis of the inner ellipse contour 480' (i.e., the bone surface) and outer ellipse contour 480" (i.e., the cartilage surface) of the one non-damaged condyle of the femur restored bone model 28', the inner ellipse contour 480' (i.e., the bone surface) and the outer ellipse contour 480" (i.e., the cartilage surface) of the other condyle (i.e., the damage or deteriorated condyle) may be determined.

As can be understood from FIGS. 13 and 14B, ellipse contours 480', 480" are determined in areas A and B for the condyles 430, 445 of the femur restored bone model 28'. The inner ellipse contour 480', representing the bone-only surface, and the outer ellipse contour 480", representing the bone-and-cartilage surface, can be obtained. The minimum cartilage thickness $tm_{min}$ is measured based on the cartilage thickness tr between the inner ellipse 480' and outer ellipse 480". MRI slices of the two condyles 430, 445 of the femur restored bone model 28' in areas A and B are taken to compare the respective ellipse contours in areas A and B. If the cartilage loss is greatest for at the medial condyle 445 in the MRI slices, the minimum thickness $tm_{min}$ for the cartilage can be obtained from the lateral condyle 430. Similarly, if the lateral condyle 430 has the greatest cartilage loss, the cartilage thickness $tm_{min}$ can be obtained from undamaged medial condyle 445 of the femur restored bone model 28'. The minimum cartilage can be illustrated in the formula, $tm_{min}$=MIN (ti), where i=1 to k.

ii. Determining Joint Gap

As mentioned above, in one embodiment, the adjustment value tr may be determined via a joint line gap assessment. The gap assessment may serve as a primary estimation of the gap between the distal femur and proximal tibia of the restored bone model. The gap assessment may help achieve proper ligament balancing.

Figure 14E:
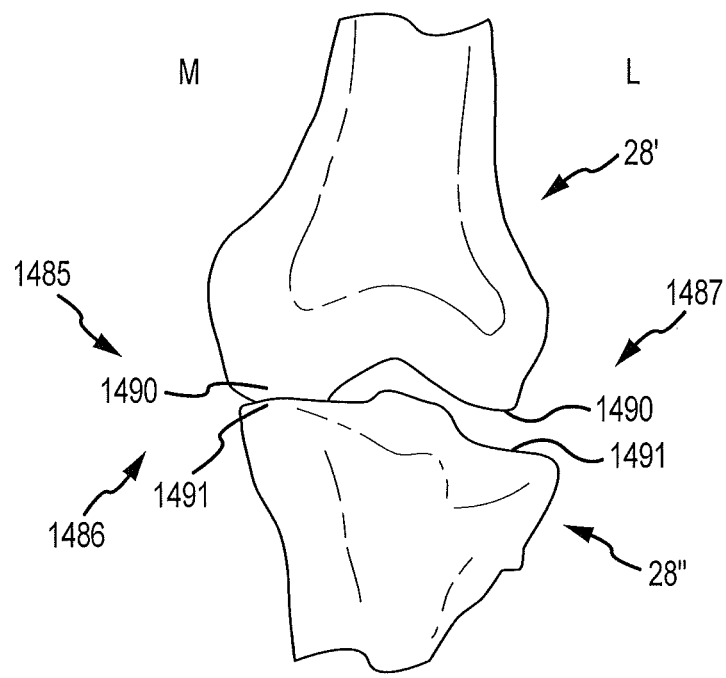
FIGS. 14E and 14F illustrate coronal views of the restored bone models in their alignment relative to each as a result of OA.

In one embodiment, an appropriate ligament length and joint gap may not be known from the restored bone models 28', 28" (see FIG. 2A) as the restored bone models may be oriented relative to each other in a fashion that reflects their deteriorated state. For example, as depicted in FIG. 14H, which is a coronal view of restored bone models 28', 28" oriented (e.g., tilted) relative to each other in a deteriorated state orientation, the lateral side 1487 was the side of the deterioration and, as a result, has a greater joint gap between the distal femur and the proximal tibia than the medial side 1485, which was the non-deteriorated side of the joint in this example.

In one embodiment, ligament balancing may also be considered as a factor for selecting the appropriate implant size. As can be understood from FIG. 14H, because of the big joint gap in the lateral side 1487, the presumed lateral ligament length (L1+L2+L3) may not be reliable to determine proper ligament balancing. However, the undamaged side, which in FIG. 14H is the medial side 1485, may be used in some embodiments as the data reference for a ligament balancing approach. For example, the medial ligament length (M1+M2+M3) of the undamaged medial side 1485 may be the reference ligament length used for the ligament balancing approach for implant size selection.

In one embodiment of the implant size selection process, it may be assumed that the non-deteriorated side (i.e., the medial side 1485 in FIG. 14H in this example) may have the correct ligament length for proper ligament balancing, which may be the ligament length of (M1+M2+M3). When the associated ligament length ("ALL") associated with a selected implant size equals the correct ligament length of (M1+M2+M3), then the correct ligament balance is achieved, and the appropriate implant size has been selected. However, when the ALL ends up being greater than the correct ligament length (M1+M2+M3), the implant size associated with the ALL may be incorrect and the next larger implant size may need to be selected for the design of the arthroplasty jig 2.

Figure 14F:
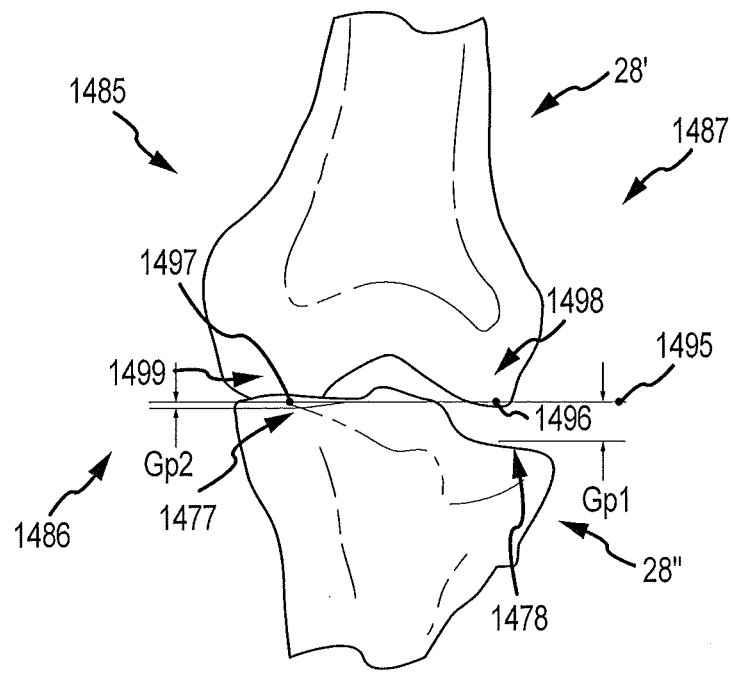

For a discussion regarding the gap assessment, which may also be based on ligament balance off of a non-deteriorated side of the joint, reference is made to FIGS. 14D and 14F. FIGS. 14E and 14F illustrate coronal views of the restored bone models 28', 28" in their post-degeneration alignment relative to each as a result of OA or injury. As shown in FIG. 14E, the restored tibia model 28" is titled away from the lateral side 1487 of the knee 1486 such that the joint gap between the femoral condylar surfaces 1490 and the tibia condylar surfaces 1491 on the lateral side 1487 is greater than the joint gap on the medial side 1485.

As indicated in FIG. 14F, which illustrates the tibia in a coronal cross section, the line 1495 may be employed to restore the joint line of the knee 1486. The line 1495 may be caused to extend across each of lowest extremity points 1496, 1497 of the respective femoral lateral and medial condyles 1498, 1499. In this femur restored bone model 28', line 1495 may be presumed to be parallel or nearly parallel to the joint line of the knee 1486.

Figure 14G:
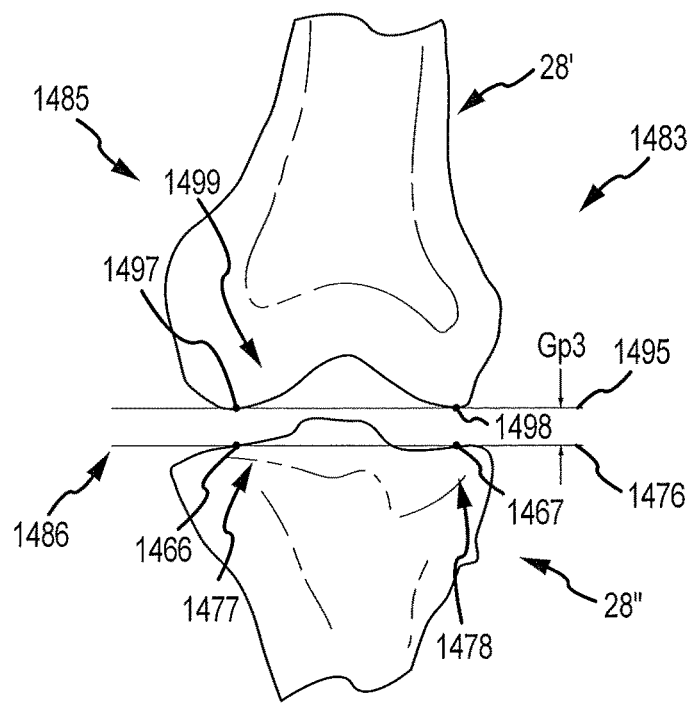
FIG. 14G illustrates a coronal view of the restored bone models with a restored gap Gp3.
Figure 14H:
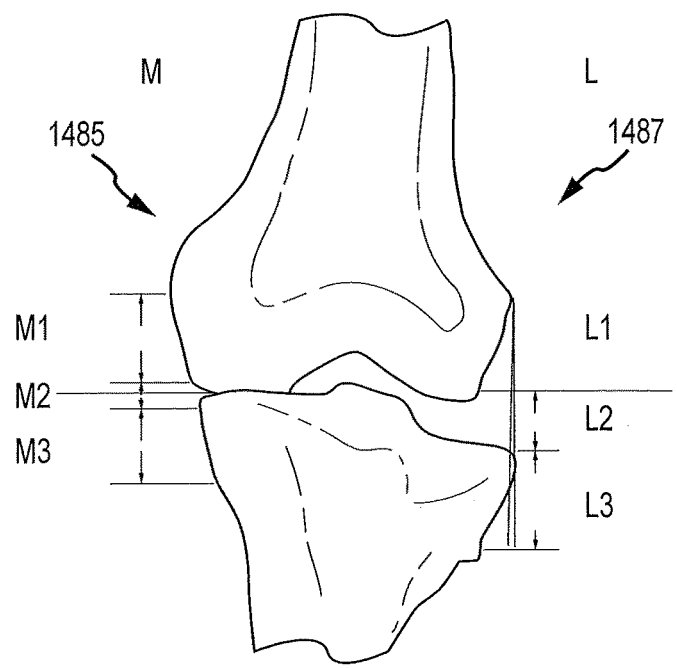
FIG. 14H is a coronal view of restored bone models oriented relative to each other in a deteriorated state orientation.

As illustrated in FIG. 14F, the medial gap Gp2 represents the distance between the distal femoral medial condyle 1499 and the proximal tibia medial plateau 1477. The lateral gap Gp1 represents the distance between the distal femoral lateral condyle 1498 and the proximal tibia lateral plateau 1478. In this example illustrated in FIG. 14F, the lateral gap Gp1 is significantly larger than the medial gap Gp2 due to degeneration caused by injury, OA, or etc. that occurred in the lateral side 1487 of the knee 1486. It should be noted that while the bone models 28', 28" have surface configurations that have been restored such that the bone models 28', 28" are restored bone models 28', 28", the alignment of the bone models 28', 28" relative to each other for the example illustrated in FIGS. 14E and 14F depict the alignment the actual bones have relative to each other in a deteriorated state. To restore the joint line reference and maintain ligament balancing for the medial collateral ligament (MCL) and lateral collateral ligament (LCL), the joint line gap Gp3 that is depicted in FIG. 14G, which is the same view as FIG. 14E, except with the joint line gap Gp3 in a restored state, may be used for the shape matching adjustment as described below. As illustrated in FIG. 14G, the lines 1495 and 1476 respectively extend across the most distal contact points 1496, 1497 of the femur condyles 1498, 1499 and the most proximal contact points 1466, 1467 of the tibia plateau condyles 1477, 1478.

For calculation purposes, the restored joint line gap Gp3 may be which ever of Gp1 and Gp2 has the minimum value. In other words, the restored joint line gap Gp3 may be as follows: Gp3=MIN (Gp1, Gp2). For purposes of the adjustment to the shape matching, the adjustment value tr may be calculated as being half of the value for Gp3, or in other words, tr=Gp3/2. As can be understood from FIGS. 14E-14F and 14H, in this example, the non-deteriorated side 1485 has Gp2, which is the smallest joint line gap and, therefore, Gp3=Gp2 in the example depicted in FIG. 14E-14H, and tr=Gp2/2.

In one embodiment, the joint line gap assessment may be at least a part of a primary assessment of the geometry relationship between the distal femur and proximal tibia. In such an embodiment, the joint gap assessment step may occur between [block 173] and [block 174] of FIG. 1J. However, in other embodiments, the joint line gap assessment may occur at other points along the overall POP process.

4. Adjust Femoral Implant to Account for Joint Gap or Cartilage Thickness.

Figure 15A:
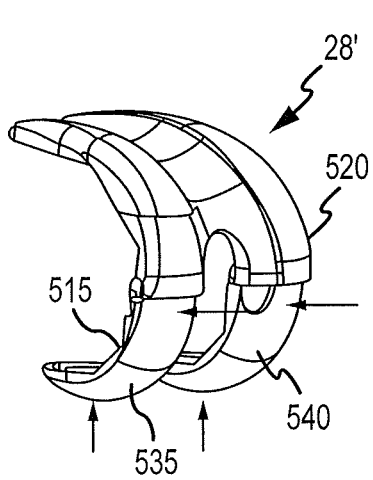
FIGS. 15A and 15B are, respectively, an isometric view and a lateral side view of the modified femoral implant model.
Figure 15B:
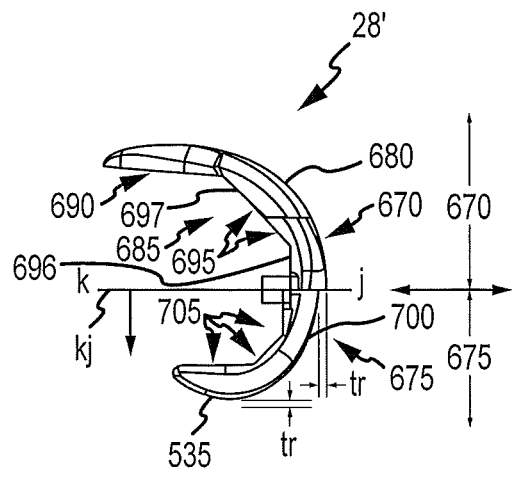

Once the adjustment value tr is determined based off of cartilage thickness or joint line gap Gp3, the femoral implant model 34' can be modified or adjusted to account for cartilage thickness to restore the joint line (see FIG. 1K [block 181]. FIGS. 15A and 15B are, respectively, an isometric view and a lateral side view of the modified femoral implant model 34'.

As can be understood from FIGS. 15A and 15B, the modification of femoral implant model 34' occurs below line KJ in FIG. 15B. The inner elliptical bone surface model 480' and the outer elliptical cartilage surface model 480" in FIG. 14B can be illustrated in the each of formula (1) and formula (2), respectively:

$$\frac{(x-x)^2}{p^2} + \frac{(y-y)^2}{q^2} = 1 \qquad \text{Formula (1)}$$

$$\frac{(x-x)^2}{r^2} + \frac{(y-y)^2}{s^2} = 1 \qquad \text{Formula (2)}$$

where P=wr, q=ws, and 0<w<1, wherein when p=q the result is a circle curve and when p≠q the result is an ellipse curve. Via the adjustment value tr, a restored condylar shape may be obtained by using the ellipse model and the mathematical information described above. The outer ellipse 480" may be attached with the adjustment value tr, which may be representative of cartilage thickness or half of the restored joint gap Gp3, and the inner ellipse 480' may be the bone contour without cartilage extending about the bone contour. The inner and outer ellipse 480', 480" may differ in a ratio of w factor, where 0<w<1. Based on the w factor, the p radius is smaller than radius r in a ratio of w. A similar analogy applies for radius q, where q is smaller than s in a ratio of w.

As best illustrated in FIG. 15B, the femoral implant model 34' includes an upper or distal-anterior part 670 and a lower or distal-posterior part 675 separated by the line KJ. The upper or distal-anterior part 670 of femoral implant model 34' comprises an external anterior-distal articular surface 680 and a multi-faced interior anterior-distal non-articular surface 685. The interior anterior-distal non-articular surface 685 includes an anterior non-articular surface 690 and a distal-anterior non-articular surface 695.

A distal portion 696 of the distal-anterior non-articular surface 695 may be a plane generally perpendicular to a natural alignment vertically extending axis when the actual physical implant is mounted on the distal femur end as part of an arthroplasty procedure. An anterior chamfered portion 697 of the distal-anterior non-articular surface 695 may be a plane having a generally chamfered relationship to the distal portion 696.

The distal portion 696 of the distal-anterior non-articular surface 695 may abut against the first distal planar resection formed in the distal femur end during the arthroplasty procedure. The first distal planar resection may act as a guide from which other resections (e.g., the posterior and anterior chamfer resections) are referenced. The anterior chamfered portion 697 of the distal-anterior non-articular surface 695 may abut against the anterior planar resection formed in the distal femur end during the arthroplasty procedure. Thus, the interior anterior-distal non-articular surface 685 is adapted to receive the anterior flange of a resected distal femur.

The lower or distal-posterior part 675 of femoral implant model 34' includes an external posterior-distal articular surface 700 and a multi-faced interior posterior-distal non-articular surface 705. The external posterior-distal articular surface 700 includes the medial distal-posterior condylar articulating surface 540 and the lateral distal-posterior condylar articulating surface 535. The lower or distal-posterior part 675 of femoral implant model 34' is modified to account for the adjustment value tr, which may be based on the cartilage thickness or half of the restored joint gap Gp3. In one embodiment, the adjustment value tr is applied in both a posterior-anterior direction and a distal-proximal direction to the lower or distal-posterior portion 675 of the implant model 34'

As can be understood from FIGS. 15A and 15B, the condyle surface 535 modified to account for the damaged bone and cartilage loss is dimensioned smaller than the condyle surface 540 for the non-damaged bone by a factor w in both the distal and posterior portions, wherein w equals the adjustment thickness tr. With the study of the cartilage thickness or restored joint gap Gp3, the system 4 can provide the restoration of cartilage and therefore assess the joint line for the distal femur model 28'.

5. Shape Matching of Condyle Surfaces of Restored Femoral Bone Model to Condyle Surfaces of Femoral Implant Model.

Figure 16:
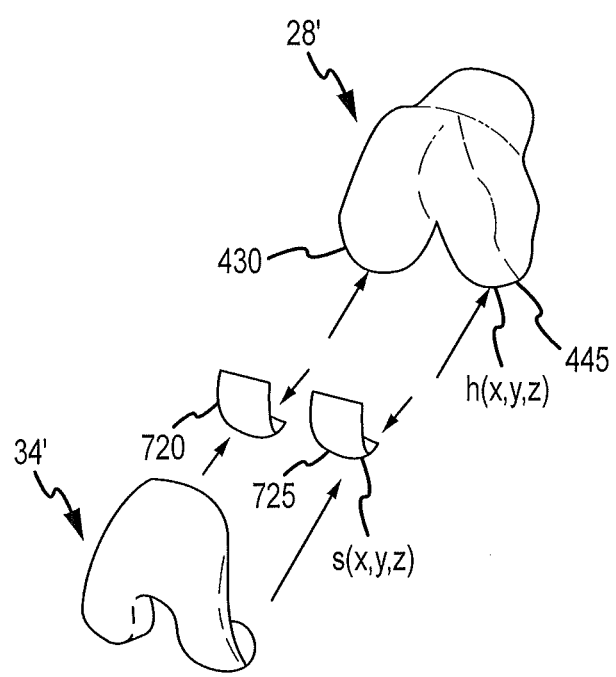
FIG. 16 is an isometric view of a femoral implant model being shape matched to a femur restored bone model.

FIG. 16 is an isometric view of a femoral implant model 34' being shape matched to a femur planning model 28' (see FIG. 1K [block 182]). As shown in FIG. 16, the femur implant model 34' is direct surface matched onto the surface of the restored femur bone model 28' such that the articular surface profile of the femoral implant model 34' is matched to the articular surface profile of the femoral condyles 430, 445 of the femur restored bone model 28'. The function s (x, y, z) represents the surface profiles 720, 725 for each of the exterior distal-posterior articular surfaces 700 of the lower or distal-posterior part 675 of the implant model 34' in FIG. 15B. The function h (x, y, z) represents the articular surface profile of a femoral condyle 430, 445 of the lower or distal-posterior part of a femur restored bone model 28' as it would be if line KJ of FIG. 15B were applied to a femur restored bone model 28' situated similar to the implant model 34' in FIG. 15B.

In one embodiment, the surface models 720, 725 may displace medial-lateral relative to each other, but are constrained to move with each other in all other directions. For example the surface models 720, 725 may displace closer or further apart to each other along the x-axis, but are matched to displace along the y-axis and z-axis as a set and fixed relative to each other.

The function $\bar{e}(x,y,z)$ represents a true vector assuming that template noise is independent of the implant surface profile noise. The problem is estimating the parameters of a 3D transformation that satisfies the least squares fit surface matching of the implant condyle articular surface profile s (x, y, z) to the femoral condyle articular surface profile h (x, y, z). This can be achieved by minimizing a goal function, which measures the sum of squares of the Euclidean distances between these two surface profiles, represented by $\bar{e}(x,y,z)=h(x,y,z)-s(x,y,z)$. For greater detail regarding this operation, see the following publications, which are incorporated by reference in their entireties into this Detailed Description: D. Akca, *Matching of 3D Surfaces and Their Intensities*, ISPRS Journal Of Photogrammetry & Remote Sensing, 62 (2007), 112-121; and Gruen A. et al., *Least Squares 3D surface and Curve Matching*, ISPRS Journal of Photogrammetry & Remote Sensing 59 (2005), 151-174.

Figure 17A:
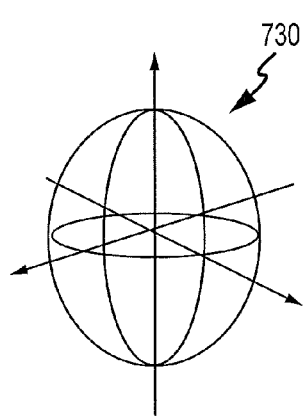
FIGS. 17A and 17B are isometric views of an ellipsoid model of a femoral condyle obtained through a plurality of MRI slices taken in a manner similar to the MRI slice depicted in FIG. 12 and from areas A and B in FIG. 13.
Figure 17B:
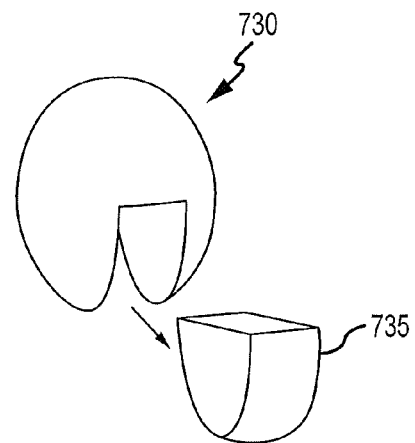

As an option to the process discussed with respect to FIGS. 15A 16, the femur implant model 34' can be directly shape matched onto the femur restored bone model 28' as described in the following discussion. FIGS. 17A and 17B are isometric views of an ellipsoid model 730 of a femoral condyle 430, 445 obtained through a plurality of MRI slices taken in a manner similar to the MRI slice depicted in FIG. 12 and from areas A and B in FIG. 13. Each of the femoral condyles 430, 445 in FIG. 13 consists of a series of ellipses in areas A and B. Therefore, the 3D ellipsoid model 730 of the condyles 430, 445 can be reconstructed by repetitive image analysis through a plurality of MRI slices taken through areas A and B in FIG. 13 in a manner similar to the MRI slice depicted in FIG. 12. As shown in FIG. 17B, a portion 735 of the femoral condyle model 730 can be segmented and removed from the rest of the model 730.

Figure 18:
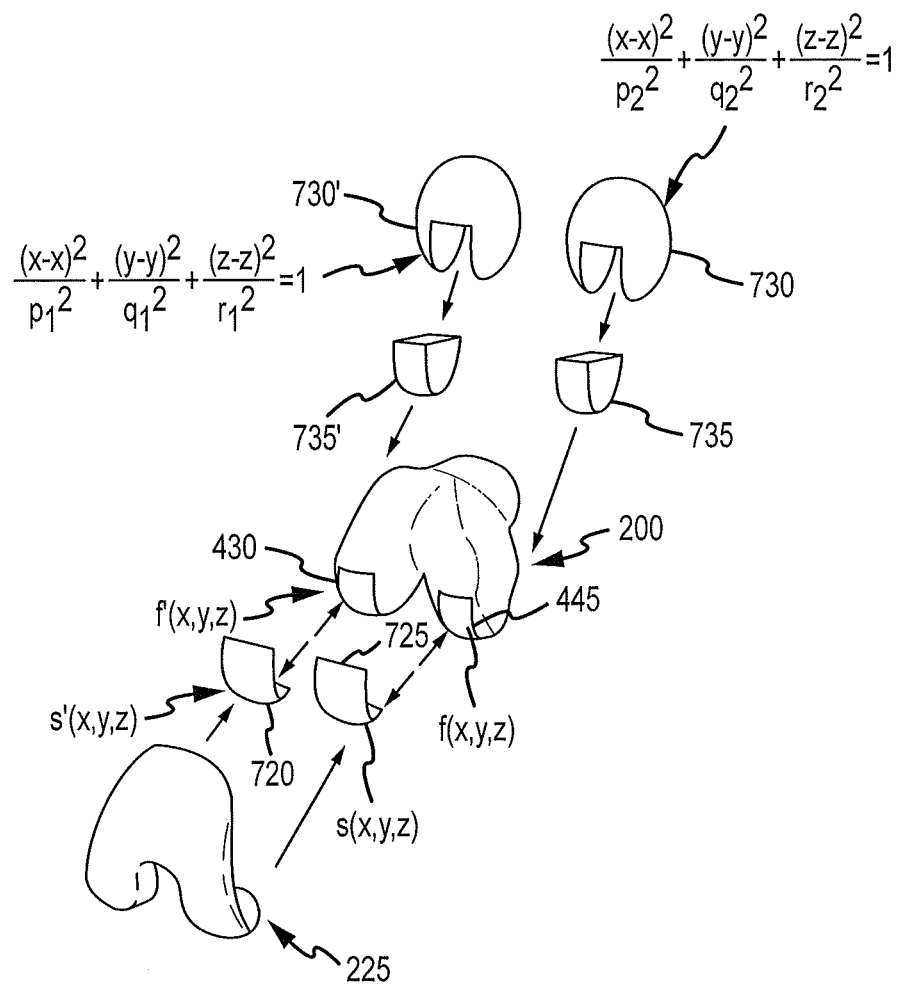
FIG. 18 is an isometric view depicting the 3D surface matching using the condyle models of FIGS. 17A and 17B.

FIG. 18 is an isometric view depicting the 3D surface matching using the condyle models 730 of FIGS. 17A and 17B. The surface matching technique provides varus/valgus and information for the femoral implant planning design. The drilling hole of the femur implant model 34' and the surgical cut plane SCP of the femur implant model 34' provide the information for the IR/ER rotation. In FIG. 18, each of the ellipsoid model 735, 735' represents the femoral condyles 430, 445 of the distal femur restored bone model 28'. The ellipsoid condylar portions 735, 735' are each taken out from the 3D models 730, 730'. The ellipsoid equation in model 730' can be illustrated as $$\frac{(x-x)^2}{p_2^2} + \frac{(y-y)^2}{q_2^2} + \frac{(z-z)^2}{r_2^2} = 1.$$

The ellipsoid equation in model in 730 can be illustrated as $$\frac{(x-x)^2}{p_1^2} + \frac{(y-y)^2}{q_1^2} + \frac{(z-z)^2}{r_1^2} = 1.$$

The surface models of ellipsoid condylar portions 735, 735' can be obtained from these two ellipsoid equations. These two portions 735, 735' correspond to the distal-posterior portions of each condyle 430, 445 of the distal femur surface model 28'. In the femur model 28', the function f (x, y, z) represents a portion of ellipsoid surface of model portion 735, approximately describing the distal-posterior bone surface of the medial condyle 445. Similarly, the function f' (x, y, z) represents a portion of ellipsoid surface of model portion 735', approximately describing the distal-posterior bone surface of the lateral condyle 430.

The function s (x, y, z) represents the surface model 725 of the medial distal-posterior exterior articular surface 700 of the lower or distal-posterior part 675 of femoral implant model 34' in FIG. 15B. The s' (x, y, z) represents the surface model 720 of lateral distal-posterior exterior articular surface 700 of the lower or distal-posterior part 675 of femoral implant model 34' in FIG. 15B.

In one embodiment, the surface models 720, 725 may displace medial-lateral relative to each other, but are constrained to move with each other in all other directions. For example the surface models 720, 725 may displace closer or further apart to each other along the x-axis, but are matched to displace along the y-axis and z-axis as a set and fixed relative to each other.

The function e(x, y, z) represents a true vector assuming that template noise is independent of the implant surface profile noise. The parameters of a 3D transformation satisfy the least squares matching of the interior surface profile (x, y, z) of the implant to the ellipsoid potions surface profile f (x, y, z) of the femoral condyle. Similarly, the e(x, y, z) represents the least squares matching of the interior surface profile s' (x, y, z) of the implant to the ellipsoid potions surface profile f'(x, y, z) of the femoral condyle. This can be achieved by minimizing a goal function, which measures the sum of squares of the Euclidean distances between the two surface profiles, represented by e(x,y,z)=f(x,y,z)−s(x,y,z), and e'(x,y,z)=f'(x,y,z)−s'(x,y,z), where J=MIN (e(x,y,z)), and J'=MIN (e'(x,y,z)). See D. Akca (supra). The valgus/varus and IR/ER of the original joint line has now been restored.

Figures 19A, 19B:
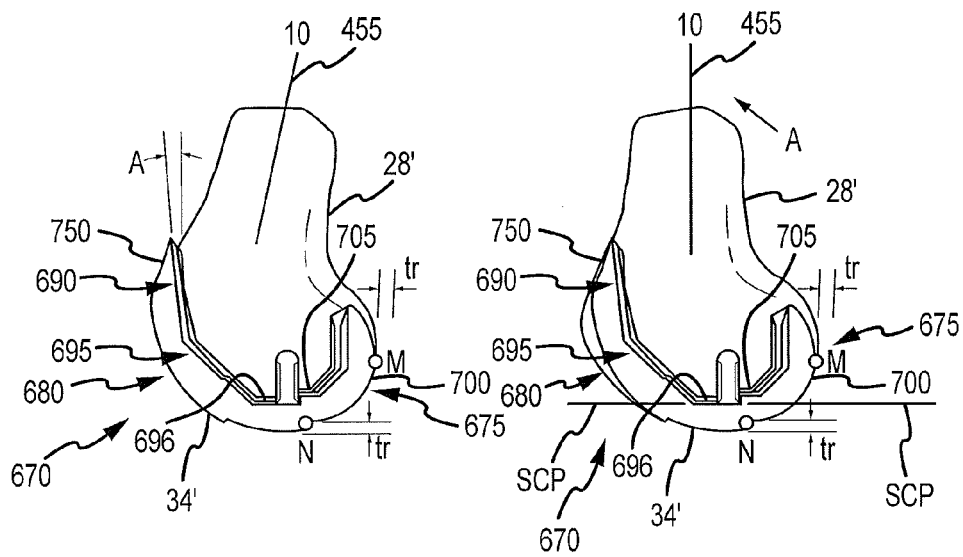
FIG. 19A shows the sagittal view of inaccurate rotation alignment between the anterior flange of femoral implant model and the anterior portion of the femur restored bone model.
FIG. 19B shows the sagittal view of correct rotation alignment between the anterior flange of the femoral implant model and the anterior portion of the femur restored bone model.

6. Aligning with Respect to Rotation and Translation the Modified Femoral Implant Model to the Femur Model FIG. 19A shows the sagittal view of inaccurate rotation alignment between the anterior flange 750 of a modified femoral implant model 34' and the anterior distal femur restored bone model 28'. FIG. 19B shows the sagittal view of correct rotation alignment between the anterior flange 750 of the modified femoral implant model 34' and the anterior distal femur restored bone model 28'.

As previously discussed with respect to FIGS. 15A and 15B, the distal-anterior part 670 of the modified femoral implant model 34' includes an external anterior-distal articular surface 680 and an interior anterior-distal non-articular surface 685. The interior anterior-distal non-articular surface 685 includes the anterior non-articular surface 690 and the distal anterior non-articular surface 695. The sizes of distal-anterior part 670 of the modified femoral implant model 34' are selected from the femoral implants currently available from implant manufactures and according to the method discussed with respect to the bAP and bML extents of femur planning model 28' in FIGS. 3A-3C.

As can be understood from a comparison of FIG. 19A to FIG. 19B, the distal femur restored bone model 28' is rotated a certain number of degrees so the interior anterior-distal non-articular surface 685 can be adapted to meet the anterior cortex of distal femur restored bone model 28', while points M and N are preserved as much as possible to minimize error. The extent to which the femur model restored bone model 28' is rotated relative to the implant model 34' can be understood from a comparison of the FAA 455 in FIGS. 19A and 19B.

By employing the three-point tangent contact spot method (i.e., points M, N, and any points between M and N), the minimum degree of error A° is achieved. The degree of error A° is based on the limitation of available sizes of commercial implants, where 0<A°<20°. For example, some implant manufacturers only make available eight sizes of femoral implants. If the patient's femur bAP extent is greater than the iAP extent of the selected implant size, while the bML is approximately equal to iML, then applying the model 34' of the selected implant to align with the patient's femur restored bone model 28' will cause an error of degree A° that is larger than a 20° rotation alignment range. In this case it is suggested to choose the next bigger size of implant to minimize the degree of error.

As can be understood from FIGS. 7A, 7B, 15B and 19B, once the distal-posterior articular surfaces 700 of the implant model 34' are shape matched to the corresponding distal-posterior articular surfaces of the restored femur bone model 28', the distal portion 696 of the distal-anterior non-articular surface 695 will be superposed in the femur restored bone model 28' to indicate a location of a distal surgical cut plane or distal resection plane SCP that will correspond to a saw cut slot 123 (see FIGS. 1F and 1G) in the femur arthroplasty jig 2A that can be used to create the first distal planar resection formed in the distal femur end during the arthroplasty procedure. As the posterior-distal articular surface 700 is adjusted for the adjustment value tr for the shape matching process, the SCP ends up being located distally further by the amount of the adjustment value tr than it would otherwise be, resulting in the actual physical implant when mounted on the actual distal femur end providing articular surfaces that are positioned and oriented so as to allow the patient's knee to assume a natural or non-degenerated configuration.

The orientation and location of the implant's mounting post P (see FIG. 7B) may also be determined once the implant model 34' and restored bone model 28' are superposed. Also, the locations and orientations of the drill holes 124 (see FIGS. 1F and 1G) of the arthroplasty jig 2A may be determined from the implant model 34' and restored bone model 28' being superposed.

Once the shape match process (see FIG. 1K [block 182] and FIG. 1C [block 120]) is complete, the information regarding the locations and orientations for the saw cut slot 123 and drill holes 124 may be packaged as saw cut and drill hole data 44 (see FIG. 1E [block 125]) and the process goes forward as outlined in FIG. 1E.

Figure 20:
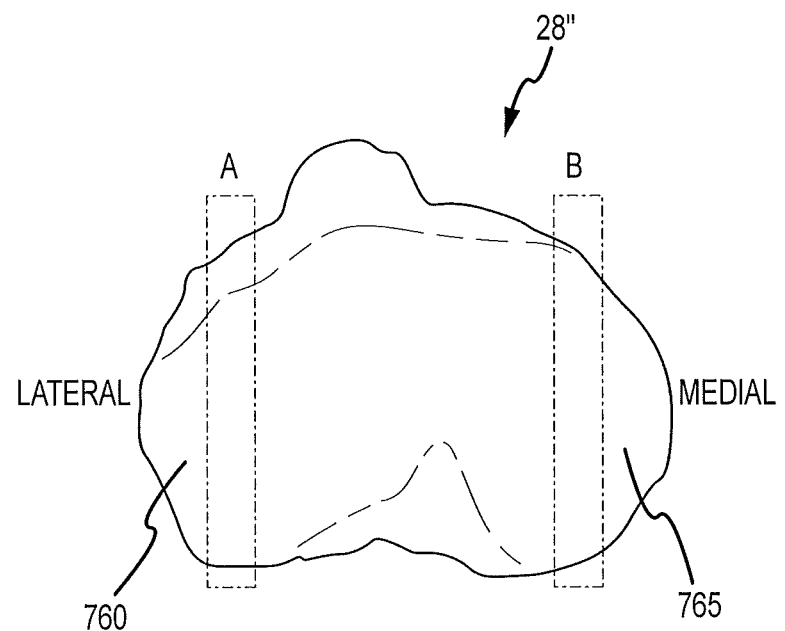
FIG. 20 is a plan or top view of the plateau of the tibia restored bone model.

H. Determining Areas of Interest A, B for Tibia Plateau Corresponding to Areas of Interest A, B for the Femoral Condyles FIG. 20 is a plan or top view of the plateau of the tibia restored bone model 28". As shown in FIG. 20, areas of interest A and B, which are similar to those depicted on the femur condyles 430, 445 in FIG. 13, are identified on the surface of lateral plateau 760 and medial plateau 765 of tibia restored bone model 28" (see FIG. 1J [block 183]). The surface shape of the medial plateau 765 is incongruent with the lateral plateau 760. The lateral plateau 760 shows a roughly flat surface. The medial plateau 765 shows a roughly concaved recess. The areas A and B of focus on portions of the medial and lateral plateau surfaces 765, 760. The areas A and B represent the contact areas around the joint line for articulatingly receiving the corresponding respective distal surfaces of the femoral medial and lateral condyles 445, 430 identified in FIG. 13.

I. Determining Reference Points for Tibia Plateau

As with the identification of the distal reference points at the most distal points of the femoral condyle articular surfaces, as discussed above, corresponding reference points are identified on the tibia plateaus (see FIG. 1J [block 184]). As may be understood from the following discussion, the reference points for the tibia plateaus may be located at the lowest or most distally recessed points in each respective plateau.

Figure 21A:
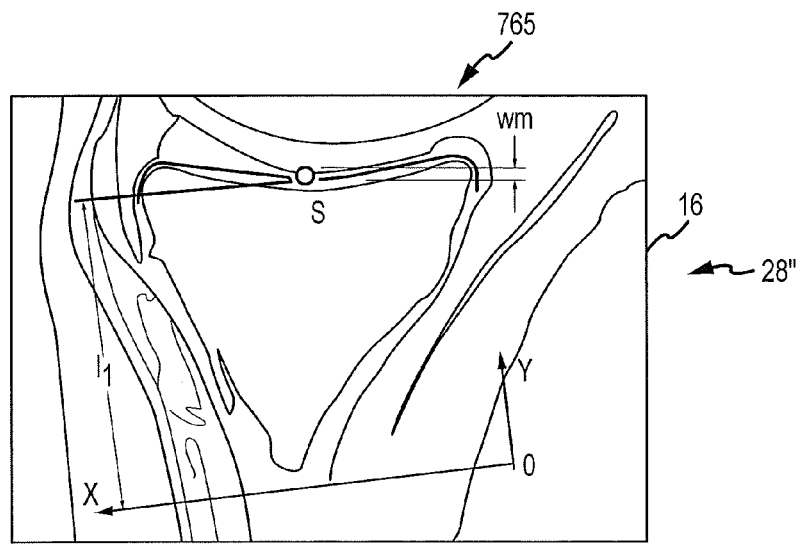
FIG. 21A is a MRI image slice of the medial portion of the proximal tibia and indicates the establishment of landmarks for the tibia POP design.
Figure 21B:
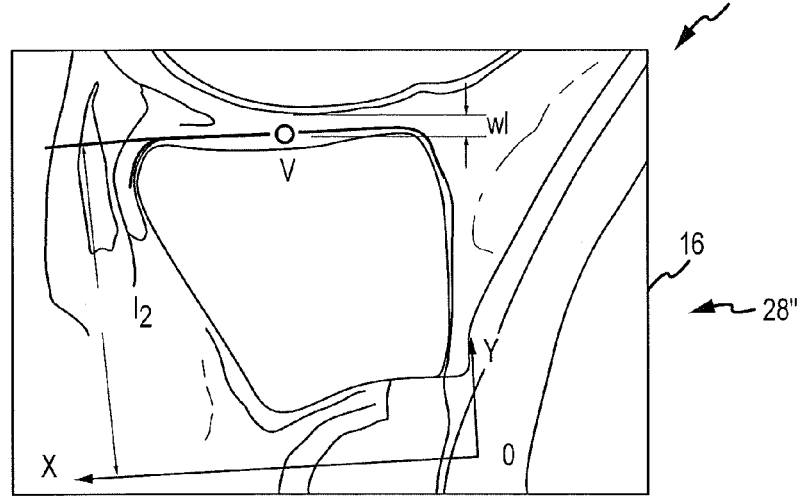
FIG. 21B is a MRI image slice of the lateral portion of the proximal tibia.
Figure 21C:
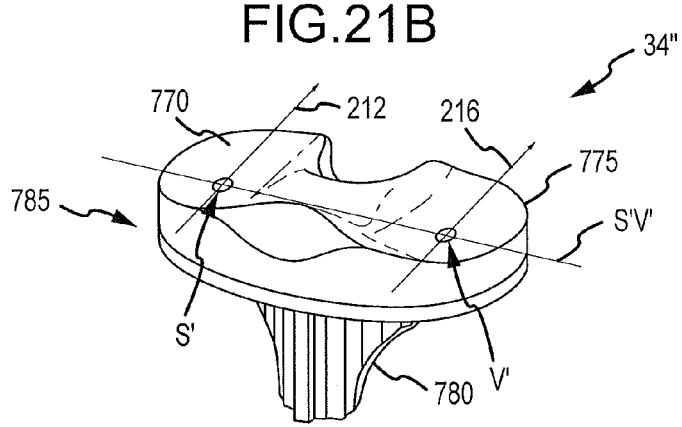
FIG. 21C as an isometric view of the tibia implant model.

FIGS. 21A-C illustrate the initial varus/valgus position of the tibia restored bone model 28" and the tibia implant model 34". FIG. 21A is a MRI image slice 16 of the medial portion 765 of the proximal tibia used to form the tibia restored bone model 28" and indicates the establishment of landmarks for the tibia POP design. The joint line may be assessed as described above with respect to FIGS. 12-14F. The surface contour of the medial plateau 765 is outlined along the tibia meniscus starting from a portion of the anterior medial surface to a posterior medial surface as shown in FIG. 21A. The reference spot S is selected and located approximately in the midpoint of the surface contour of the tibia medial plateau 765. The reference spot S is located within the area of interest B in FIG. 20 and may be the most distally recessed point within area B.

FIG. 21B is a MRI image slice 16 of the lateral portion 760 of the proximal tibia used to form the tibia restored bone model 28". The surface contour of lateral plateau 760 is outlined along the tibia meniscus starting from a portion of the anterior lateral surface to the posterior lateral surface. The reference spot V is selected and located approximately in the midpoint of the surface contour of the tibia lateral plateau 760. The reference spot V is located within the area of interest A in FIG. 20 and may be the most distally recessed point within area A.

In each of the MRI slices 16, the landmarks as well as the origin O of the medial and lateral tibia plateaus 765, 760 for IR/ER rotation and alignment of the tibia implant model 34" can be obtained. A medial-lateral extending line connecting both spots S, V can be made which is parallel to the joint line or parallel to a reference Z-axis of the X-Y axis indicated in FIGS. 21A and 21B. In the slices 16 depicted in FIGS. 21A and 21B, the length of line I1 equals the length of line I2. In other words, the respective distances of each point S and V from the origin O along the y-axis are equal. This provides an "x" coordinate and a "y" coordinate, as the (x, y) origin O has a coordinate of (0, 0), as shown in FIGS. 21A and 21B. The plane formed by the x-axis and z-axis (i.e., the plane perpendicular to the x-y plane) is parallel to the joint line. Corresponding reference points S', V' are indicated on the lateral and medial plateaus 770, 775 of the implant model 34", which is depicted in FIG. 21C as an isometric view.

In FIG. 21C, the tangent or reference points S', V' represent the midpoints of the respective surfaces of the medial tibia plateau 775 and the lateral tibia plateau 770. These two points S', V' are located in the respective areas of interest described in FIG. 20. Also, each point S', V' may represent the most distally recessed point in the respective tibia plateau 775, 770. A vector direction line-212 extends across point-S' in medial tibia plateau 775. A vector direction line-216 extends across point-V' in the lateral tibia plateau 770. The vector-212 is parallel or generally parallel to vector-216, and is about the same height with vector-216. The line-S'V' extends across points-S' and V' and can be obtained. This line-S'V' is parallel or generally parallel to the joint line of the knee.

As can be understood from FIGS. 21A-21C, the midpoints S, V in the medial plateau 765 and lateral plateau 760 of tibia 205 coincide with the points S', V' located approximately at the centre of the medial and lateral bearing surfaces 775, 770 of the tibia implant model 34". As indicated in FIG. 21C, the tibia implant 34" includes a base member 780 for being secured to the proximal tibia 28". The line across the points S', V' of tibia implant 34" is parallel to the joint line and, parallel to the X-axis of the MRI slices of FIGS. 21A and 21B.

J. Determining Joint Line and Adjustment to Surface Matching That Allows Surface Matching of Implant Model Condylar Surfaces to Restored Bone Model Condylar Surfaces to Restore Joint to Natural Configuration.

In order to allow an actual physical arthroplasty implant to restore the patient's knee to the knee's pre-degenerated or natural configuration with its natural alignment and natural tensioning in the ligaments, the condylar surfaces of the actual physical implant generally replicate the condylar surfaces of the pre-degenerated joint bone. In one embodiment of the systems and methods disclosed herein, condylar surfaces of the restored bone model 28" are surface matched to the condylar surfaces of the implant model 34". However, because the restored bone model 28" may be bone only and not reflect the presence of the cartilage that actually extends over the pre-degenerated condylar surfaces, the surface matching of the modeled condylar surfaces may be adjusted to account for cartilage or proper spacing between the condylar surfaces of the cooperating actual physical implants (e.g., an actual physical femoral implant and an actual physical tibia implant) used to restore the joint such that the actual physical condylar surfaces of the actual physical cooperating implants will generally contact and interact in a manner substantially similar to the way the cartilage covered condylar surfaces of the pre-degenerated femur and tibia contacted and interacted.

Thus, in one embodiment, the implant model is modified or positionally adjusted to achieve the proper spacing between the femur and tibia implants. To achieve the correct adjustment, an adjustment value tr may be determined (see FIG. 1J [block 185]). In one embodiment, the adjustment value tr that is used to adjust the surface matching may be based off of an analysis associated with cartilage thickness. In another embodiment, the adjustment value tr used to adjust the surface matching may be based off of an analysis of proper joint gap spacing, as described above with respect to FIGS. 14E and 14F. Both of the methods are discussed below in turn.

i. Determining Cartilage Thickness

The wm in FIG. 21A represents the cartilage thickness of the medial tibia meniscus, and the wl in FIG. 21B represents the cartilage thickness of the lateral tibia meniscus. In one embodiment, the cartilage thicknesses wl and wm are measured for tibia meniscus for both the lateral and medial plateaus 760, 765 via the MRI slices depicted in FIGS. 21A and 21B. The measured thicknesses may be compared. If the cartilage loss is observed for the medial plateau 765, then the $wl_{min}$ of lateral plateau 760 is selected as the minimum cartilage thickness. Similarly, if the lateral plateau 760 is damaged due to cartilage loss, then the $wm_{min}$ of medial plateau 765 is selected as the minimum cartilage thickness. The minimum cartilage wr may be illustrated in the formula, wr=min (wm, wl). In one embodiment, for purposes of the adjustment to the tibia shape matching, the adjustment value tr may be may be equal to the minimum cartilage value wr.

ii. Determining Joint Gap

In one embodiment, the joint gap is analyzed as discussed above with respect to FIGS. 14E and 14F to determine the restored joint line gap Gp3. In one embodiment, for purposes of the adjustment to the tibia shape matching, the adjustment value tr may be calculated as being half of the value for Gp3, or in other words, tr=Gp3/2.

K. Determine Slope Vectors for Tibia Plateau

The slope vectors for the plateau of the tibia restored bone model 28" are determined (see FIG. 1J [block 186]), as will be discussed with respect to FIGS. 22A and 22B. The sagittal view of FIGS. 22A and 22B are, respectively, lateral and medial sagittal MRI views of the plateau of the tibia restored bone model 28".

Figure 22A:
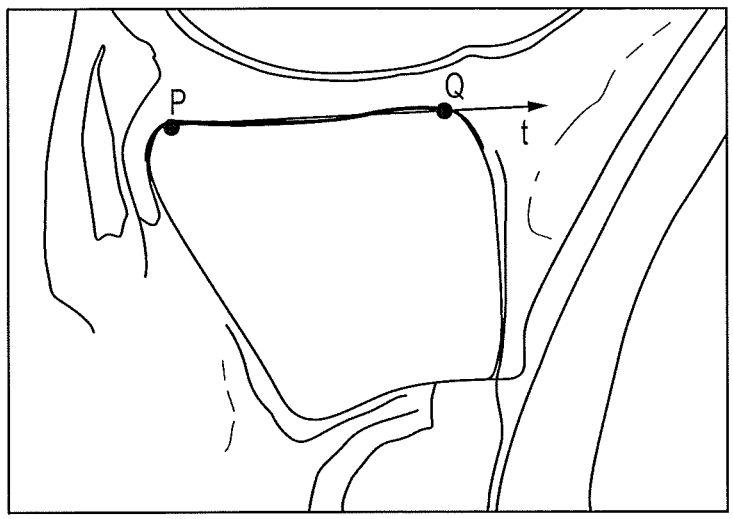
FIGS. 22A and 22B are, respectively, lateral and medial sagittal MRI views of the plateau of the tibia.

FIG. 22A shows the lateral tibial plateau 760 for establishing the anterior-posterior landmark references in the tibia plateau. FIG. 22B shows the medial tibial plateau 765 for establishing the anterior-posterior landmark references in the tibia plateau. The anterior-posterior references can apply to both the tibia restored bone model 28", as can be understood from the MRI slices of FIGS. 22A and 22B and the tibial implant model 34" of FIGS. 23A-23C.

As indicated in FIG. 22A, points P, Q represent the highest of the anterior and posterior portions of lateral plateau surface 760. The direction vector PQ in FIG. 22A represents the anterior-posterior slope of the lateral plateau 760 of tibia restored bone model 28".

Figure 22B:
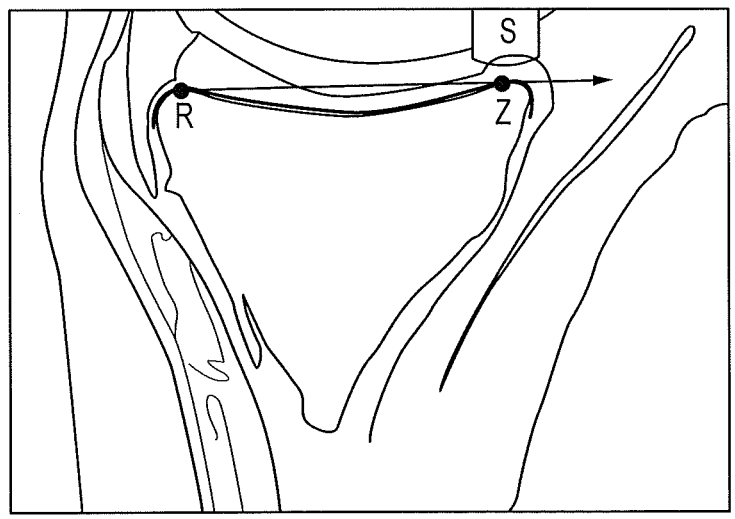

As indicated in FIG. 22B, points R, S represent the highest of the anterior and posterior portions of medial plateau surface 765. The direction vector RS in FIG. 22B represents the anterior-posterior slope of the medial plateau 765 of tibia restored bone model 28". For these vectors, it can be said that vector PQ is equal to vector t, vector RS is equal to vector z, and vector t is parallel to vector z or substantially parallel such that the acute angle between vectors z and t is less than five degrees.

L. Determine Slope Vectors for Tibia Implant

Figure 23A:
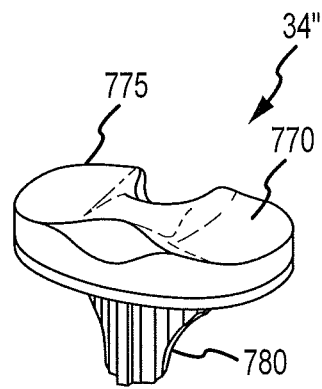
FIGS. 23A-23C are, respectively, two isometric views and a side view of the tibia implant model.
Figure 23B:
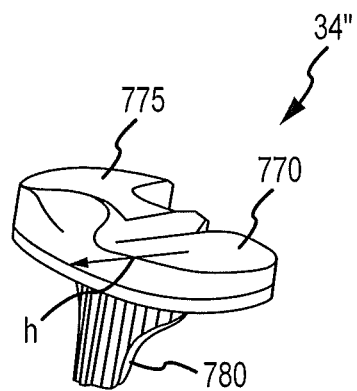
Figure 23C:
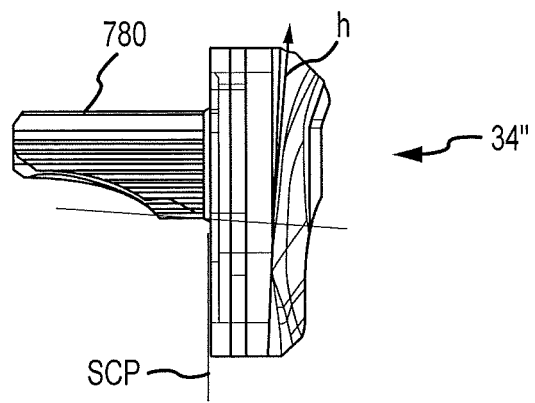

The of slope vectors for the plateau of the tibia implant model 34" are determined (see FIG. 1J [block 187]), as will be discussed with respect to FIGS. 23A-23C. The same analogy described with respect to finding the slope vectors for the tibia plateaus of the tibia restored bone model 28" applies to the tibia implant model 34" of FIGS. 23A-23C. FIGS. 23A-23C are, respectively, two isometric views and a side view of the tibia implant model 34". Because the tibia implant model 34" is a symmetric design, the anterior-posterior slope in both the medial and lateral plateaus 775, 770 of the implant model 34" are parallel to each other. The information regarding direction vector t in the lateral side and direction vector z in the medial side of tibia restored bone model 28" applies to the anterior-posterior slopes of tibia implant model 34". In the case when vectors t and z are within a five degree difference, an average value is provided by α, where $$\alpha = \frac{\vec{PQ} + \vec{RS}}{\left\| \vec{PQ} + \vec{RS} \right\|}.$$

FIGS. 23A-23C depict a left knee tibia implant model 34". As can be understood from FIG. 23A, the plateaus 770, 775 of the tibia implant model 34" are symmetrical as viewed normal to the plateaus. As indicated in FIG. 23B, the lateral bearing surface 770 is quite close to being a flat surface as compared to the medial surface 775.

As shown in FIGS. 23B and 23C, the direction vector h represents the anterior-posterior slope of tibia implant model 34". A process similar to that employed to determine the anterior-posterior slope for the tibia restored bone model 28" in FIGS. 22A and 22B, wherein the tibia plateau MRI slices were used to determine direction vectors t and z, can be applied to the tibia implant model 34" where vector h is parallel to vector z, which is parallel to vector t. Therefore, the anterior-posterior slope information for the lateral plateau can be obtained in tibia implant model 34" in FIG. 23C.

The same analogy applies to the tibia implant model 34" of the right knee, where the implant is a symmetric design. The lateral surface profile of a right knee tibia implant is close to a flat surface. The anterior-posterior slope information for the lateral plateau of the planning model of the right knee can apply to the lateral surface profile of the tibial implant of the right knee.

M. Addressing Possible IR/ER Misalignment for the Tibial Implant

Figure 24A:
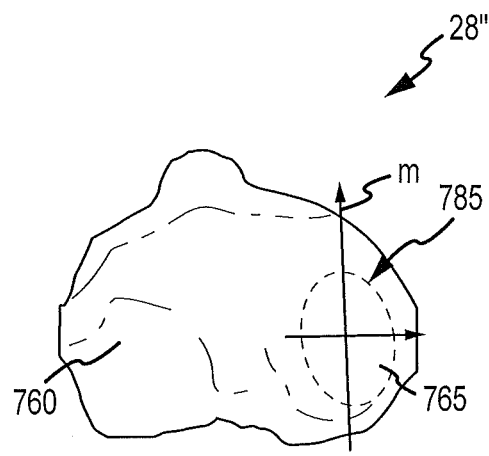
FIGS. 24A and 24B, which are, respectively, a plan or top view of the tibia plateau and a side medial side view of the tibia restored bone model.
Figure 24B:
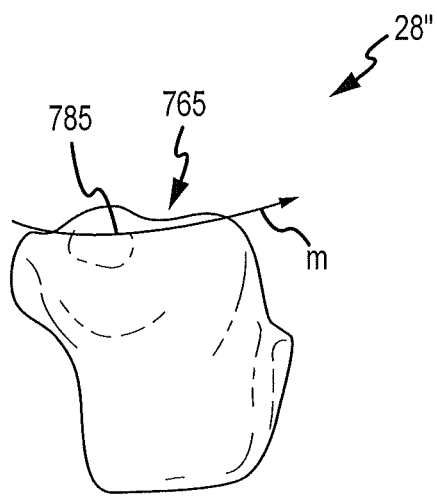

The possible IR/ER misalignment issue for the design of tibial implant model 34" can be assessed (see FIG. 1J [block 188]), as depicted in FIGS. 24A and 24B, which are, respectively, a plan or top view of the tibia plateau and a side medial side view of the tibia restored bone model 28". The medial plateau 765 of tibia restored bone model 28" in FIGS. 24A and 24B shows the elliptical concavity 786. The direction vector m in FIG. 24B shows a rolling or sliding movement of the medial condyle 445 of the femur restored bone model 28'. In FIG. 24A, the tangential line m along the medial plateau 765 of the tibia restored bone model 28" can be obtained. The elliptical shape 786 (shown in dashed lines) in the medial plateau 765 is identified, as indicated in FIG. 24A. The major axis (i.e., vector m) of the ellipse 786 provides the IR/ER alignment information to the location of tibial implant model 34".

The above described landmark references and the IR/ER alignment of the tibial restored bone model 28" provides the proximity information of the landmarks and IR/ER alignment to the tibial implant model 34".

N. Modifying the Tibial Implant Model to Account for the Adjustment Value tr

Figure 25:
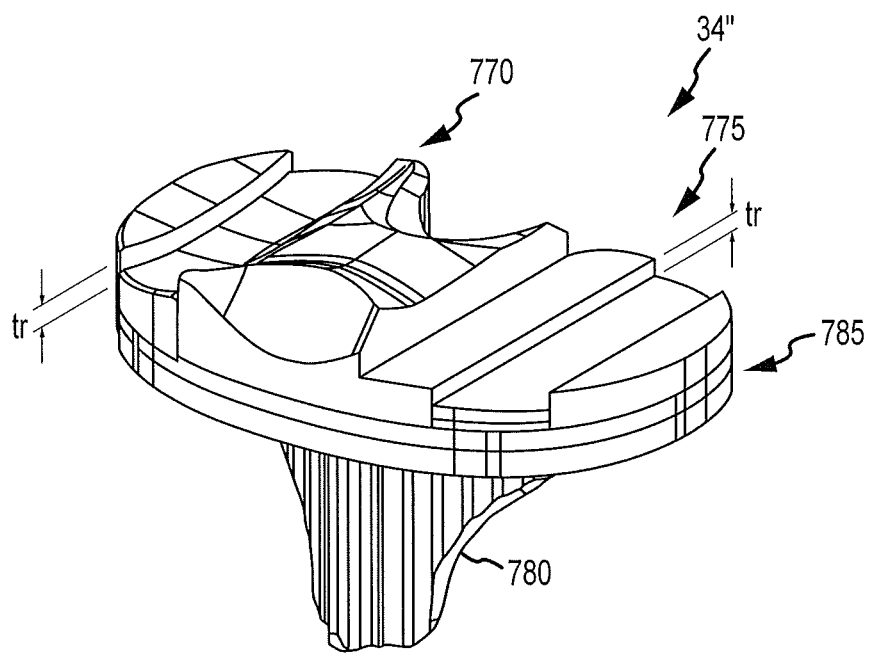
FIG. 25 is an isometric view of the tibia implant model as it is compensated to account for the adjustment value tr.

FIG. 25 is an isometric view of the tibia implant model 34" as it is compensated to account for the adjustment value tr, which depending on the embodiment, may be a function of cartilage thickness or restored joint gap. As shown in FIG. 25, the tibia implant model 34" can be compensated with respect to the adjustment value tr in the medial and lateral sides 775, 770 of the articular bearing member 785 of tibial implant model 34" (see FIG. 1J [block 189]).

The adjustment value tr may be determined via any of the above-described embodiments. Having determined the adjustment value tr, the compensation of the tibial implant model 34" for the adjustment value tr can be achieved by lowering the mid-portions of each tibial plateau 770, 775 a fir distance. For example, the mid-portions of the medial side 775 will be lowered to achieve the adjustment value tr. Similarly, the mid-portions of the lateral side 770 of the articular bearing member 785 will be lowered to achieve the adjustment value tr.

O. Surface Matching for Tibia Implant

Figure 26:
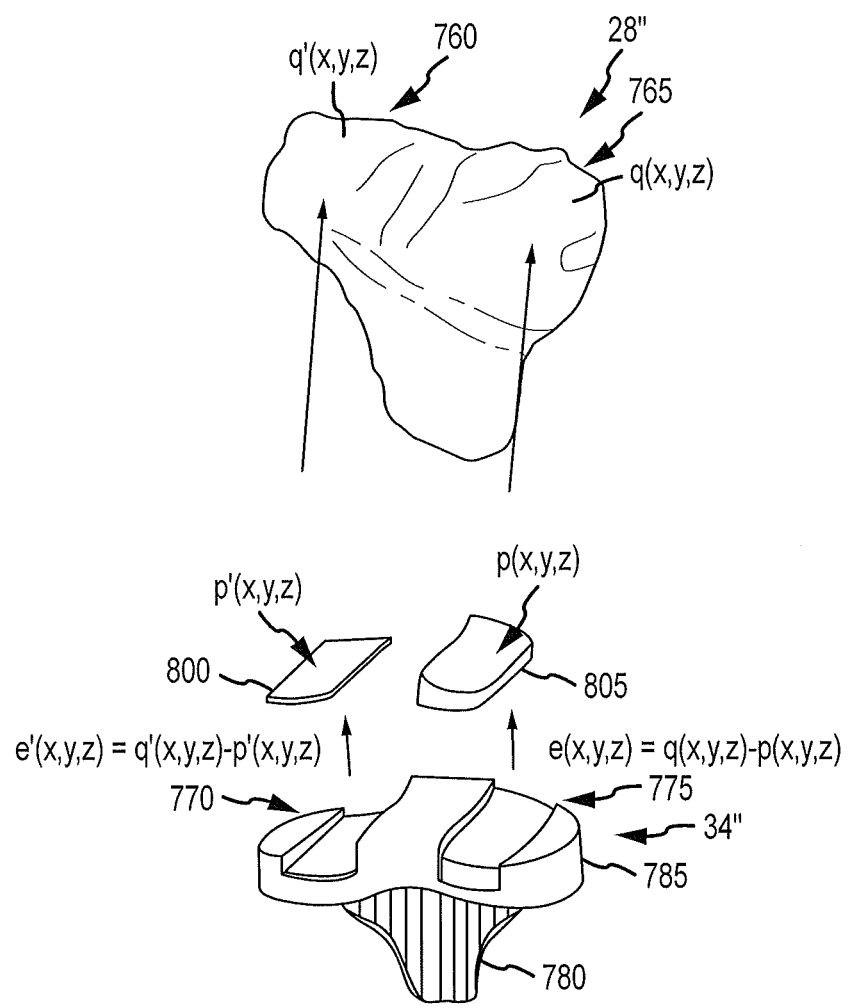
FIG. 26 is an isometric view of the tibia implant model being surface matched relative to the tibia restored bone model.

FIG. 26 is an isometric view of the tibia implant model 34" being surface matched relative to the tibia restored bone model 28" (see FIG. 1J [block 190]). As shown in FIG. 26, direct surface matching occurs from the plateau surfaces 760, 765 of tibia bone restored bone model 28". The modeling of surface profiles 800, 805 of the lateral and medial plateau 770, 775 of the tibial implant model 34" are based from each of the portions of lateral and medial plateau 760, 765 of tibia restored bone model 28", respectively.

For example, based on the surface profile q (x, y, z) of the medial plateau 765 of the restored bone model 28", the surface profile 805 (i.e., p (x, y, z)) of medial portion 775 of the implant model 34" can be obtained. The function e(x, y, z) represents a true vector assuming that template noise is independent of the implant medial surface profile noise. The problem is estimating the parameters of a 3D transformation which satisfies the least squares fit 3D surface matching of the tibial medial surface profile 805 (i.e., p (x, y, z)) of the tibial implant model 34" to the medial plateau surface profile q (x, y, z) of restored bone model 28". This can be achieved by minimizing a goal function, which measures the sum of squares of the Euclidean distances between these two surface profiles, represented by e(x,y,z)=q(x,y,z)−p(x,y,z).

The same rationale applies to the surface profile modeling of the lateral compartment 800 of implant model 34". Based on the surface profile q' (x, y, z) of lateral plateau 760 in restored bone model 28", the surface profile 800 (i.e., p' (x, y, z) of the lateral compartment 770 of the implant model 34" can be obtained. The e'(x, y, z) represents a true vector assuming that template noise is independent of the implant medial surface profile noise. Again, the problem is estimating the parameters of a 3D transformation which satisfies the least squares fit 3D surface matching the lateral surface profile 800 (i.e., p' (x, y, z)) of the tibial implant model 34" to the lateral plateau surface profile q (x, y, z) of the tibial restored bone model 28". This can be achieved by minimizing a goal function, which measures the sum of squares of the Euclidean distances between these two surface profiles, represented by e'(x,y,z)=q'(x,y,z)−p'(x,y,z). See D. Akca (supra).

Figure 27A:
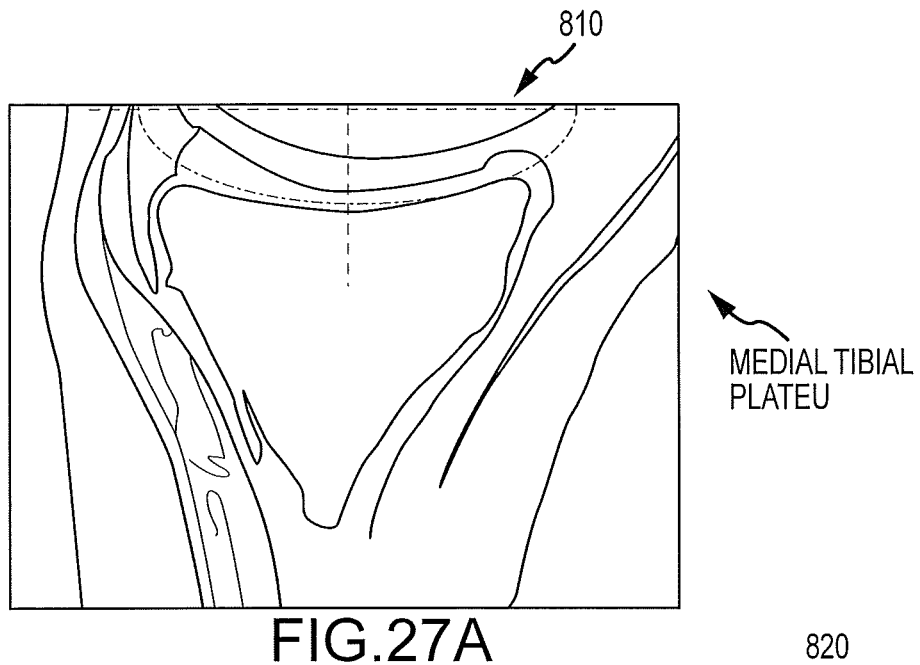
FIGS. 27A and 27B are, respectively, medial and lateral sagittal MRI views of the tibia.
Figure 27B:
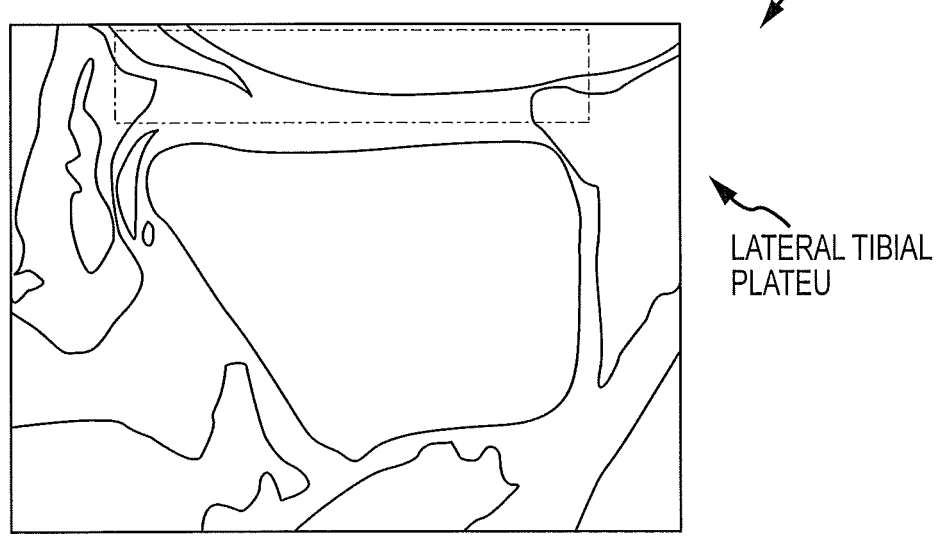
Figure 28:
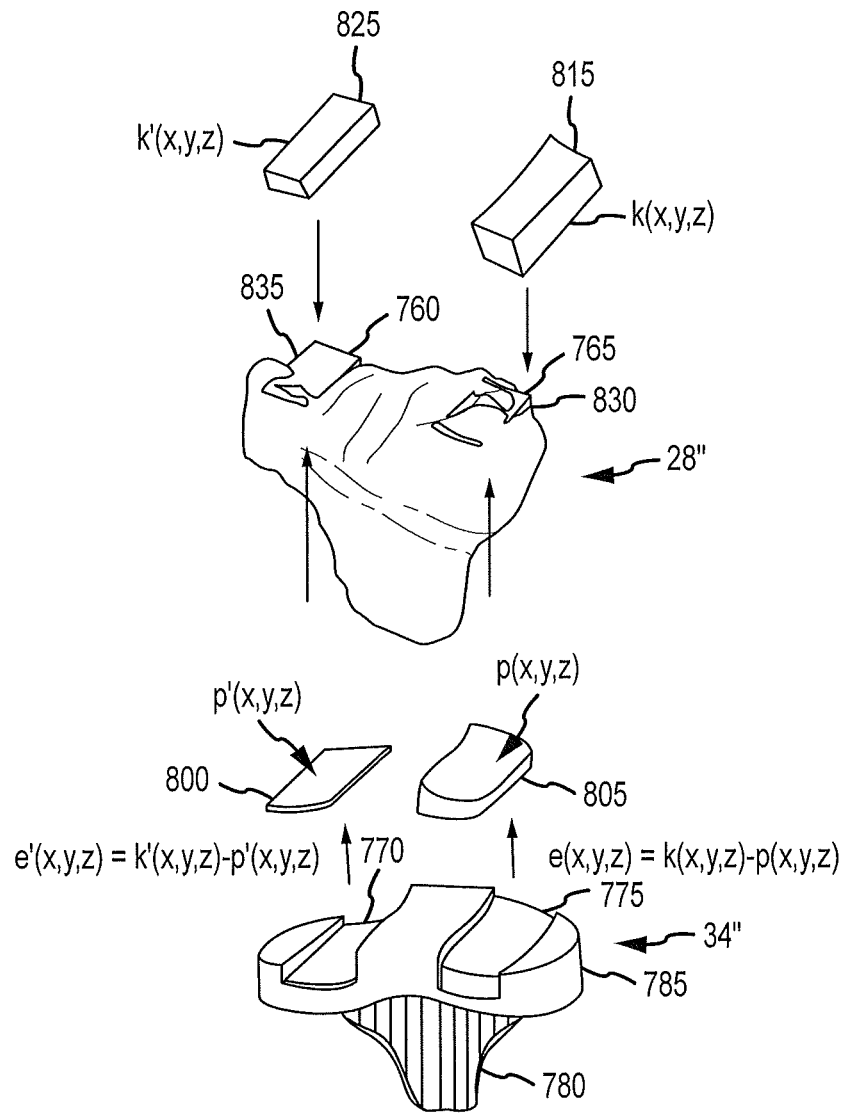
FIG. 28 is an isometric view of the tibia restored bone model and tibia implant model being used in the surface matching process.

Surface modeling, as described in the following discussion, can be utilized as an option to the surface matching process discussed with respect to FIG. 26. FIGS. 27A and 27B are, respectively, medial and lateral sagittal MRI views of the tibia. FIG. 28 is an isometric view of the tibia restored bone model 28" and tibia implant model 34" being used in the surface matching process.

FIG. 27A shows the elliptical concavity outline 810 in as viewed via a medial MRI slice. Each of the medial plateau MRI slices shows an ellipse shape in Area A of FIG. 20. The major axis and radius of the ellipse can be obtained in FIGS. 24A and 24B. A 3D ellipsoid model 815 from medial tibia plateau 765 in FIG. 28 can then be reconstructed by computer software through a plurality of MRI slices similar to the MRI slice depicted in FIG. 27A.

FIG. 27B shows the rectangle shape outline 820 in a lateral MRI slice. Each of the lateral plateau MRI slices shows a rectangle shape 820 in Area B of FIG. 20. The 3D rectangle block model 825 from the lateral tibia plateau 760 in FIG. 28 can then be reconstructed by computer software through a plurality of MRI slices similar to the MRI slice depicted in FIG. 27B.

FIG. 28 shows a representation of 3D surface matching that can be employed with the process discussed with respect to FIGS. 27A and 27B. As described above, the ellipsoid model 815 is reconstructed from the medial plateau MRI slices. The surface profile of this ellipsoid model 815 can be represented as k(x,y,z). The medial concavity 830 matches the ellipsoid model 815.

The surface profile 805 (i.e., p(x,y,z)), representing the medial compartment 775 of the articular bearing member 785, can be obtained either through the surface profile of the ellipsoid model 815 or the medial concavity 830 of the tibial restored bone model 28", as shown in FIG. 28. The function e(x, y, z) represents a true vector assuming that template noise is independent of the implant surface profile noise. The pathmeters of a 3D transformation satisfy the least squares fit 3D surface matching so as to match the surface profile 805 (i.e., p (x, y, z)) of the medial compartment 775 to the surface profile k (x, y, z) of ellipsoid model 815. This can be achieved by minimizing a goal function, which measures the sum of squares of the Euclidean distances between these two surface profiles, represented by e(x,y,z)=k(x,y,z)−p(x,y,z). See D. Akca (supra).

The rectangle block model 825 is reconstructed from the lateral plateau MRI slices. The surface profile of this rectangle block model 825 can be represented as k'(x,y,z). The lateral concavity 835 matches the rectangle block model 825. In one embodiment, the surface profile 800 (i.e., p'(x,y,z)), representing the lateral compartment 760 of the articular bearing member 785, can be obtained either through the surface profile of the rectangle block model 825 or the lateral concavity 835 of the tibial restored bone model 28" as shown in FIG. 28. The function e'(x, y, z) represents a true vector assuming that template noise is independent of the implant surface profile noise. The parameters of a 3D transformation satisfy the least squares fit 3D surface matching the surface profile 800 (i.e., p' (x, y, z)) of the lateral compartment 760 to the surface profile k' (x, y, z) of rectangle block model 825. This can be achieved by minimizing a goal function, which measures the sum of squares of the Euclidean distances between these two surface profiles, represented by e'(x,y,z)=k'(x,y,z)−p'(x,y,z). See D. Akca (supra).

P. Determining Surgical Cut Plane for Tibia

Figure 29A:
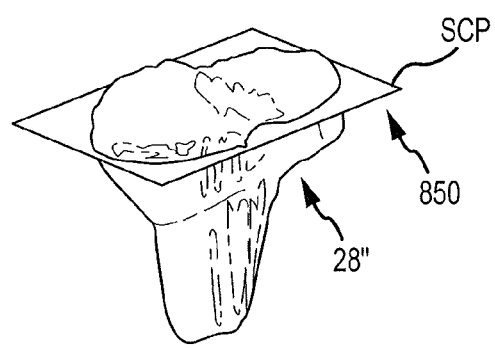
FIG. 29A is an isometric view of the tibia restored bone model showing the surgical cut plane design.
Figures 29B, 29C:
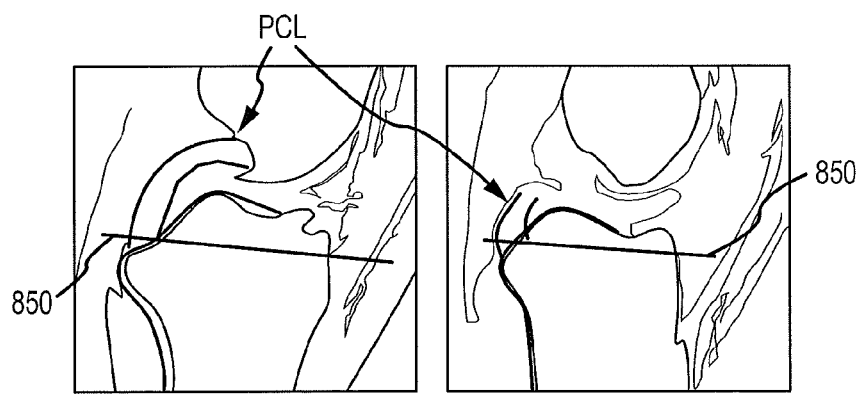
FIGS. 29B and 29C are sagittal MRI views of the surgical tibia cut plane design with the PCL.

FIG. 29A is an isometric view of the tibia restored bone model 28" showing the surgical cut plane SCP design. FIGS. 29B and 29C are sagittal MRI views of the surgical tibia cut plane SCP design with the PCL.

As can be understood from FIGS. 29A-29C, the surgical cut plane SCP 850 is designed in the tibial planning model of the POP procedure. During the TKA surgery, the damaged bone surface portions of the proximal tibia will be resected from the cut plane level 850 and be removed by the surgeon. As shown in FIGS. 29B and 29C, the surgical tibial cut plane 850 may be positioned above the surface where PCL is attached. Therefore, the system disclosed herein provides the maintenance of the PCL ligament during TKA surgery.

In the POP planning, if the cut plane is below the surface plane of PCL, the revaluation of the tibial implant size is conducted. In such a case, a one-size smaller implant is selected for the implant model design.

In a manner similar to that depicted in FIG. 19B, when the tibia implant model 34", which was modified according to the adjustment value tr as indicated in FIG. 25, is shape fit to the tibia restored bone model 28", the surgical cut plane SCP (see FIG. 23C) ends up being located proximally further by the amount of the adjustment value tr than it would otherwise be, resulting in the actual physical implant when mounted on the actual proximal tibia end providing articular surfaces that are positioned and oriented so as to allow the patient's knee to assume a natural or non-degenerated configuration.

The orientation and location of the implant's mounting post 780 may also be determined once the implant model 34" and restored bone model 28" are superposed. Also, the locations and orientations of the drill holes 124 (see FIGS. 1H and 1I) of the arthroplasty jig 2A may be determined from the implant model 34" and restored bone model 28" being superposed.

Once the shape match process (see FIG. 1J [block 195] and FIG. 1C [block 120]) is complete, the information regarding the locations and orientations for the saw cut slot 123 and drill holes 124 may be packaged as saw cut and drill hole data 44 (see FIG. 1E [block 125]) and the process goes forward as outlined in FIG. 1E.

Figures 30A, 30B, 30C:
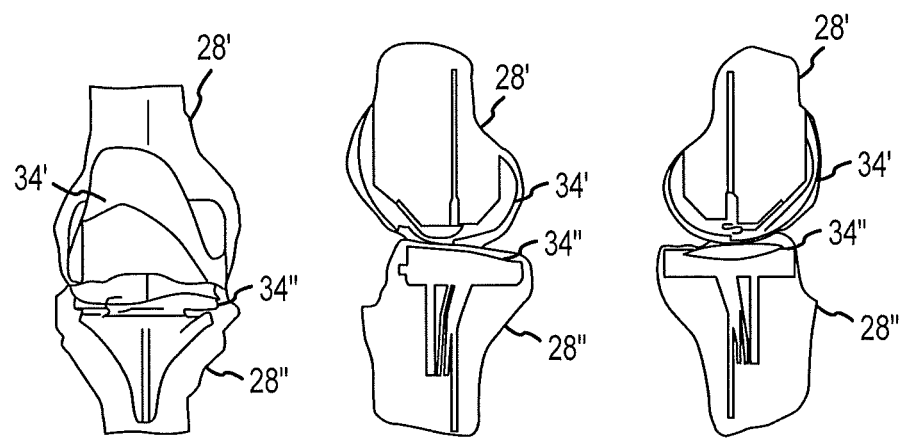
FIGS. 30A-30C are various views of the implant models superimposed on the restored bone models.
Figure 30D:
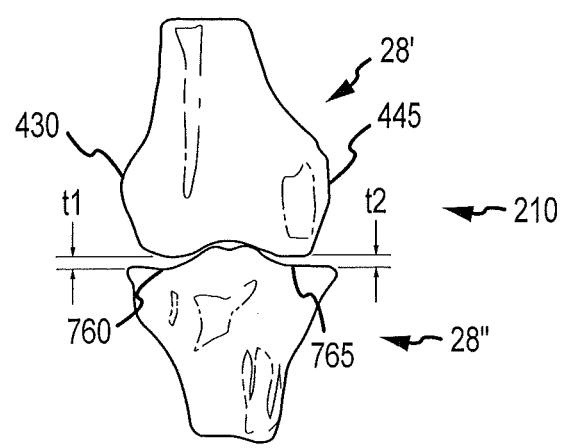
FIG. 30D is a coronal view of the restored bone models.
Figure 31A:
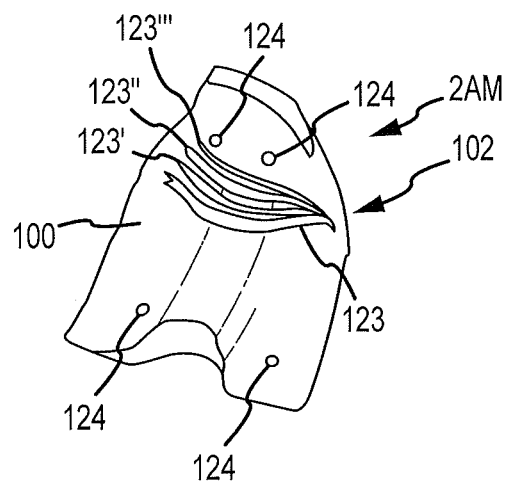
FIGS. 31A-32B illustrate isometric views of embodiments of the arthroplasty jigs configured to provide natural alignment resections, zero degree mechanical axis alignment resections, and resections resulting in alignments between zero degree mechanical axis alignment and natural alignment.
Figure 31B:
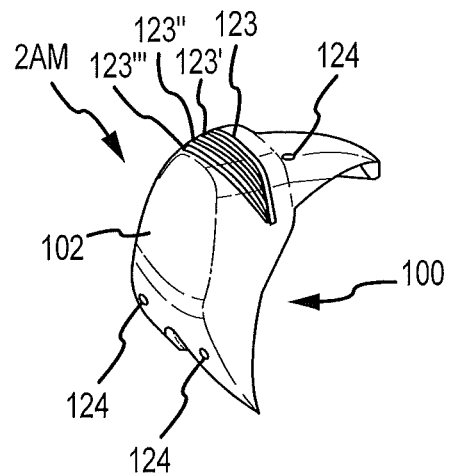
Figure 32A:
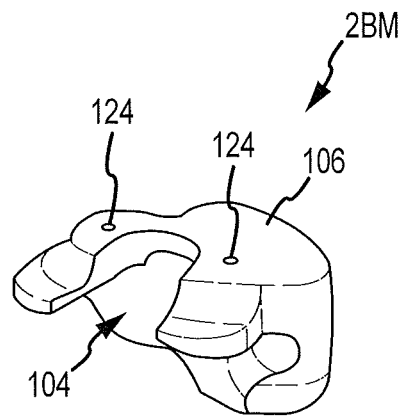
Figure 32B:
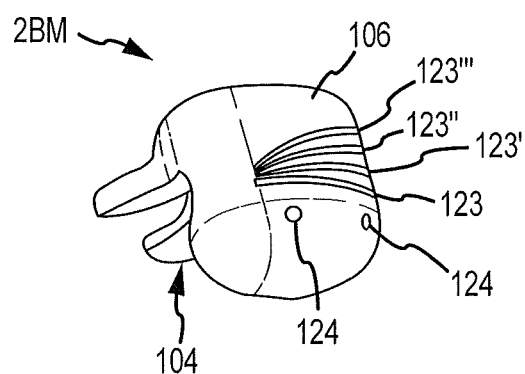

R. Verification of Implant Planning Models and Generation of Surgical Jigs Based of Planning Model Information FIGS. 30A-30C are various views of the implant models 34', 34" superimposed on the bone models 28', 28". FIG. 30D is a coronal view of the restored bone models 28', 28".

FIGS. 30A-30C show an embodiment of the POP system disclosed herein. The alignment of the implants models 34', 34" with the restored bone models 28', 28" is checked in both the anterior view (FIG. 30A) and the posterior view (not shown) and the lateral view (FIG. 30B) and the medial view (FIG. 30C).

The IR/ER rotation between the implants 34', 34" and the femur and tibia restored bone models 28', 28" is examined in both the medial view and the lateral view. For example, FIG. 30B shows the lateral view showing the IR/ER rotation between no flexion and high flexion, and FIG. 30C shows the medial view showing the IR/ER rotation between no flexion and high flexion. The stem of the tibia implant model 34" and the surgical cut plane SCP of the tibia implant model 34" provide the information for the IR/ER rotation.

FIG. 30D shows the varus/valgus alignment of the knee model 28', 28" with the absence of the implants 34', 34". The gaps g1, g2 between the lowermost portions of distal femoral condyles 430, 445 and the lowermost portions of the tibia plateau 760, 765 will be measured in the femoral and tibia restored bone models 28', 28". Gap g1 represents the distance between the distal lateral femoral condyle 430 and the lateral tibial plateau 760. Gap g2 represents distance between the distal medial femoral condyle 445 and the medial tibial plateau 765. In the varus/valgus rotation and alignment, g1 is substantially equal to g2, or |g1−g2|<<1 mm.

FIG. 30D shows the knee model 28', 28" that is intended to restore the patient's knee back to his pre-OA stage. The knee model 28', 28" and associated implant models 34', 34" developed through the above-discussed processes include dimensions, features and orientations that the system 4 depicted in FIG. 1A can utilize to generate 3D models of femur and tibia cutting jigs 2. The 3D model information regarding the cutting jigs can the be provided to a CNC machine 10 to machine the jigs 2 from a polymer or other material.

S. Mechanical Axis Alignment

While much of the preceding disclosure is provided in the context of achieving natural alignment for the patient's knee post implantation of the actual physical femur and tibia implants, it should be noted that the systems and methods disclosed herein can be readily modified to produce an arthroplasty jig 2 that would achieve a zero degree mechanical axis alignment for the patient's knee post implantation.

For example, in one embodiment, the surgeon utilizes a natural alignment femoral arthroplasty jig 2A as depicted in FIGS. 1F and 1G to complete the first distal resection in the patient's femoral condylar region. Instead of utilizing a natural alignment tibia arthroplasty jig 2B as depicted in FIGS. 1H and 1I, the surgeon instead completes the first proximal resection in the patient's tibia plateau region via free hand or a mechanical axis guide to cause the patient's tibia implant to result in a mechanical axis alignment or an alignment based off of the mechanical axis (e.g., an alignment that is approximately one to approximately three degrees varus or valgus relative to zero degree mechanical axis).

In one embodiment, as indicated in FIGS. 31A-32B, the arthroplasty jigs 2AM and 2BM may be configured to provide bone resections that lead to natural alignment, mechanical axis alignment or alignments in between the two. For example, the jigs 2AM and 2BM may have a natural alignment saw slot 123 and one or more non-natural alignment saw slots 123', 123" and 123' that may, for example, be one degree, two degrees, three degrees or some other incremental measurement away from natural alignment and towards zero degree mechanical axis alignment. The surgeon may select a two degree deviation slot 123" based on a physical inspection and surgical experience.

In one embodiment of the POP systems and methods disclosed herein, instead of superposing and shape matching the restored bone models 28', 28" to the implant models 34', 34" in a manner that results in the saw cut and drill hole data 44 that leads to the production of natural alignment arthroplasty jigs 2A, 2B, the superposing and shape matching of the bone and implant models 28, 34 may be conducted such that the resulting saw cut and drill hole data 44 leads to the production of zero degree mechanical axis alignment arthroplasty jigs or some other type of arthroplasty jig deviating in a desired manner from zero degree mechanical axis.

Thus, depending on the type of arthroplasty jig desired, the systems and methods disclosed herein may be applied to both the production of natural alignment arthroplasty jigs, zero degree mechanical axis alignment jigs, or arthroplasty jigs configured to provide a result that is somewhere between natural alignment and zero degree mechanical axis alignment.

Although the present invention has been described with reference to preferred embodiments, persons skilled in the art will recognize that changes may be made in form and detail without departing from the spirit and scope of the invention.

What is claimed is:

1. A method of pre-operatively planning an arthroplasty procedure on a joint surface of a bone of a patient joint, the method comprising:

a.) using at least one computer to generate a restored bone model, wherein the bone model includes a three dimensional computer model of at least a portion of the joint surface of the bone of the patient joint to undergo the arthroplasty procedure, wherein the restored bone model is representative of the bone in a pre-degenerated state;

b.) using the at least one computer to receive an implant model, wherein the implant model includes a three dimensional computer model of at least a portion of a joint surface of an arthroplasty implant to be used in the arthroplasty procedure;

c.) using the at least one computer to shape match an articular joint surface of the restored bone model and a corresponding articular joint surface of the implant model; and d.) using the at least one computer to define at least one of a location and orientation of a surgical cut plane relative to the implant model and based on the shape match of step c.).

2. The method of claim 1, wherein the surgical cut plane corresponds to a proximal resection to be made in the bone of the patient, wherein the bone is a tibia.

3. The method of claim 1, wherein the arthroplasty implant is at least one of a TKR or partial knee implant.

4. The method of claim 1, wherein the patient joint is at least one of an ankle, knee, hip, wrist, elbow, shoulder, vertebra-vertebra interface, vertebra-sacrum interface, and vertebra-skull interface.

5. The method of claim 1, wherein the bone is at least one of a femur and tibia.

6. A method of generating automated manufacturing instructions for an automated manufacturing machine to manufacture an arthroplasty jig from a jig blank, the method comprising:

a.) using at least one computer to obtain two-dimensional images of a joint surface of a patient bone, the two-dimensional images generated by a medical imaging system;

b.) using the at least one computer to generate first data from the two-dimensional images, wherein the first data is representative of the joint surface in a deteriorated state;

c.) using the at least one computer to generate second data from the two-dimensional images, wherein the second data is representative of the joint surface in a non-deteriorated state;

d.) using the at least one computer to obtain third data and fourth data positionally referenced to the third data, wherein the third data is representative of a joint surface of an arthroplasty implant and the fourth data is representative of a surgical cut plane associated with the arthroplasty implant;

e.) using the at least one computer to generate fifth data from the first data, wherein the fifth data is representative of a surface of the arthroplasty jig that will matingly receive the joint surface;

f.) using the at least one computer to generate sixth data by matching the second data and the third data, the resulting sixth data including a position of the fourth data when the second and third data are matched;

g.) using the at least one computer to generate seventh data by merging the fifth data and the sixth data relative to a common origin in a coordinate system; and h.) using the at least one computer to generate the automated manufacturing instructions using the seventh data, the automated manufacturing instructions cause the automated manufacturing machine to manufacture the arthroplasty jig from the jig blank.

7. The method of claim 6, wherein the two-dimensional images are at least one of MRI and CT.

8. The method of claim 6, wherein the first data includes a three-dimensional computer generated arthritic bone model.

9. The method of claim 6, wherein the first data includes a three-dimensional computer generate surface model.

10. The method of claim 6, wherein the second data includes a three-dimensional computer generated restored bone model.

11. The method of claim 6, wherein the second data includes a three-dimensional computer generated volume model.

12. The method of claim 6, wherein the third and fourth data are associated with a three-dimensional computer generated model of the arthroplasty implant.

13. The method of claim 6, wherein the second data includes a three-dimensional computer generated volume model, the third includes a joint surface of a three-dimensional computer generated model of the arthroplasty implant, and the sixth data is generated by surface matching a joint surface of the volume model and the joint surface of the model of the arthroplasty implant.

14. The method of claim 6, wherein the second data is positionally referenced to the first data and at least some of the data respectively resulting from the first and second data is similarly positionally referenced.

15. The method of claim 14, wherein the fifth and sixth data are positionally referenced to each other to facilitate their merging.

16. The method of claim 6, wherein the automated manufacturing machine is at least one of a CNC machine and a SLA machine.

17. The method of claim 6, wherein the surgical cut plane corresponds to a distal resection to be made in the patient bone, wherein the patient bone is a femur.

18. The method of claim 6, wherein the surgical cut plane corresponds to a proximal resection to be made in the patient bone, wherein the patient bone is a tibia.

19. The method of claim 6, wherein the arthroplasty implant is at least one of a TKR or partial knee implant.

20. The method of claim 6, wherein the patient bone is at least one of a femur and tibia.

21. The method of claim 6, wherein the joint surface of the patient bone includes a condyle articular surface.

22. The method of claim 21, wherein the joint surface of the arthroplasty implant includes a condyle articular surface.

23. A method of generating design data associated with a patient bone to undergo an arthroplasty procedure, the method comprising:

a.) receive two-dimensional medical images from a medical imaging system by a computer in communication with the medical imaging system;

b.) using the computer to generate a restored bone model from the two-dimensional images, the bone model includes a three-dimensional computer model of at least a portion of a joint surface of the patient bone to undergo the arthroplasty procedure, wherein the restored bone model is representative of the bone in a pre-degenerated state;

c.) using the computer to obtain an implant model including a three-dimensional computer model of at least a portion of a joint surface of an arthroplasty implant to be used in the arthroplasty procedure;

d.) using the computer to shape match an articular joint surface of the restored bone model and a corresponding articular joint surface of the implant model; and e.) using the computer to generate the design data based on the shape match in step d.), the design data comprising at least one of a location and orientation of a surgical cut plane relative to the implant model, wherein the surgical cut plane is associated with the implant model.

24. The method of claim 23, further comprising generate automated manufacturing instructions using the design data for an automated manufacturing machine to use in manufacturing an arthroplasty jig.

25. The method of claim 23, wherein the surgical cut plane corresponds to a proximal resection to be made in the bone of the patient, wherein the bone is a tibia.

26. The method of claim 23, wherein the arthroplasty implant is at least one of a TKR or partial knee implant.

27. The method of claim 23, wherein the patient bone is part of a patient joint comprising at least one of an ankle, knee, hip, wrist, elbow, shoulder, vertebra-vertebra interface, vertebra-sacrum interface, and vertebra-skull interface.

28. The method of claim 1, wherein the patient bone is at least one of a femur and tibia.

29. The method of claim 1, further comprising e.) cutting the bone of the patient joint according to the surgical cut plane defined in step d.).

\* \* \* \* \*